(12) United States Patent
Volkar et al.

(10) Patent No.: US 12,233,027 B2
(45) Date of Patent: Feb. 25, 2025

(54) METHODS, STORAGE DEVICES, AND INFUSION SYSTEMS FOR THERAPEUTIC OR DIAGNOSTIC AGENTS

(71) Applicant: Bayer Healthcare LLC, Whippany, NJ (US)

(72) Inventors: John Volkar, Valencia, PA (US); Joana Oliveira Rego Brilhante, Jersey City, NJ (US); Anne Berit Eid, Oslo (NO); Ellia Hu, Eastwood (AU); Hamsini Sundararaman, Monroeville, PA (US); Ashley Cockerham, Tulsa, OK (US); Winston Ge, Cambridge, MA (US); Andrew Jones, Roslindale, MA (US); Richard Miller, Needham, MA (US); Joe Ting, Acton, MA (US); Brian Yoo, Arlington, MA (US); Ryan Bayne, Ithaca, NY (US)

(73) Assignee: BAYER HEALTHCARE LLC, Whippany, NJ (US)

(*) Notice: Subject to any disclaimer, the term of this patent is extended or adjusted under 35 U.S.C. 154(b) by 0 days.

(21) Appl. No.: 18/436,633

(22) Filed: Feb. 8, 2024

(65) Prior Publication Data
US 2024/0245582 A1 Jul. 25, 2024

Related U.S. Application Data

(63) Continuation of application No. PCT/US2023/062890, filed on Feb. 20, 2023.
(Continued)

(51) Int. Cl.
*A61J 1/16* (2023.01)
*A61J 1/05* (2006.01)
(Continued)

(52) U.S. Cl.
CPC ............... *A61J 1/16* (2013.01); *A61J 1/1406* (2013.01); *A61J 1/1437* (2013.01); *A61J 1/1475* (2013.01);
(Continued)

(58) Field of Classification Search
CPC .......... A61J 1/16; A61J 1/1406; A61J 1/1437; A61J 1/1475; A61J 1/05; A61J 1/2096;
(Continued)

(56) References Cited

U.S. PATENT DOCUMENTS

| 3,673,411 A | 6/1972 | Glasser |
| 3,971,955 A | 7/1976 | Heyer et al. |

(Continued)

FOREIGN PATENT DOCUMENTS

| EP | 2934630 A2 | 10/2015 |
| EP | 3067037 B1 | 10/2017 |

(Continued)

OTHER PUBLICATIONS

Hioki, T., et al., "Overlooked potential of positrons in cancer therapy", Scientific Reports, 2021, vol. 11, No. 2475.

*Primary Examiner* — Ariana Zimbouski
(74) *Attorney, Agent, or Firm* — Joseph L. Kent; James R. Stevenson; David Schramm

(57) ABSTRACT

Systems and methods for distribution, storage, transport, administration and/or disposal of one or more therapeutic or diagnostic agents are disclosed. A storage device configured to connect to a delivery system for delivering the therapeutic or diagnostic agent has a housing with a chamber, a vessel having an access port positioned within the chamber. The door is movable relative to the housing between a closed position and an open position. In the closed position, the door covers an opening in the housing to enclose the chamber, and, in the open position, the door reveals the (Continued)

opening for accessing the access port of the vessel. The door is moveable between the closed position and the open position in response to actuation by an access mechanism of the delivery system.

30 Claims, 32 Drawing Sheets

Related U.S. Application Data

(60) Provisional application No. 63/312,145, filed on Feb. 21, 2022, provisional application No. 63/312,148, filed on Feb. 21, 2022.

(51) Int. Cl.
*A61J 1/14* (2023.01)
*G21F 5/04* (2006.01)

(52) U.S. Cl.
CPC . *G21F 5/04* (2013.01); *A61J 1/05* (2013.01); *A61J 2205/10* (2013.01)

(58) Field of Classification Search
CPC ....... A61J 1/201; A61J 2205/10; G21F 5/015; G21F 5/04; G21F 5/06; G21F 5/018; A61N 2005/1021; A61N 2005/1094; A61M 5/007; A61M 5/1785
See application file for complete search history.

(56) References Cited

U.S. PATENT DOCUMENTS

| | | | |
|---|---|---|---|
| 4,092,546 A | 5/1978 | Larrabee |
| 4,382,512 A | 5/1983 | Furminger |
| 4,497,349 A | 2/1985 | Farley |
| H152 H | 11/1986 | Lampe |
| 4,673,813 A | 6/1987 | Sanchez |
| 4,775,074 A | 10/1988 | Ershig |
| 4,869,299 A | 9/1989 | Handke |
| 4,893,022 A | 1/1990 | Hall et al. |
| 4,975,591 A | 12/1990 | Hardt et al. |
| 5,397,902 A | 3/1995 | Castner et al. |
| 5,552,612 A | 9/1996 | Katayama et al. |
| 5,569,181 A | 10/1996 | Heilman et al. |
| 5,806,519 A | 9/1998 | Evans, III et al. |
| 5,828,073 A | 10/1998 | Zhu et al. |
| 5,831,271 A | 11/1998 | Okano et al. |
| 5,843,037 A | 12/1998 | Uber, III |
| 5,919,421 A | 7/1999 | Monz et al. |
| 5,920,054 A | 7/1999 | Uber, III |
| 5,944,190 A | 8/1999 | Edelen |
| 5,947,890 A | 9/1999 | Spencer et al. |
| 6,030,578 A | 2/2000 | McDonald |
| 6,155,420 A | 12/2000 | Phillips |
| 6,162,198 A | 12/2000 | Coffey et al. |
| 6,385,483 B1 | 5/2002 | Uber, III et al. |
| 6,472,675 B2 | 10/2002 | White et al. |
| 6,576,918 B1 | 6/2003 | Fu et al. |
| 6,586,758 B2 | 7/2003 | Martin |
| 6,635,234 B1 | 10/2003 | Larsen et al. |
| 6,695,363 B1 | 2/2004 | Ma |
| 6,731,971 B2 | 5/2004 | Evans, III et al. |
| 6,963,073 B2 | 11/2005 | Martin et al. |
| 7,019,317 B1 | 3/2006 | Martin et al. |
| 7,028,837 B2 | 4/2006 | Yanke et al. |
| 7,097,609 B2 | 8/2006 | Kindlein et al. |
| 7,170,072 B2 | 1/2007 | Schwarz et al. |
| 7,204,797 B2 | 4/2007 | Reilly et al. |
| 7,414,254 B2 | 8/2008 | Polsinelli et al. |
| 7,703,486 B2 | 4/2010 | Costanzo |
| 7,713,232 B2 | 5/2010 | Uber, III et al. |
| 7,753,835 B2 | 7/2010 | Van Der Lee et al. |
| 7,813,841 B2 | 10/2010 | Dekemp et al. |
| 8,071,959 B2 | 12/2011 | Dekemp |
| 8,269,201 B2 | 9/2012 | Fago et al. |
| 8,292,869 B2 | 10/2012 | Paganelli et al. |
| 8,512,306 B2 | 8/2013 | Knapp et al. |
| 8,517,905 B2 | 8/2013 | Buck et al. |
| 8,852,071 B2 | 10/2014 | Buck et al. |
| 8,926,569 B2 | 1/2015 | Bisegna et al. |
| 9,002,438 B2 | 4/2015 | Knowland et al. |
| 9,005,166 B2 | 4/2015 | Uber, III et al. |
| 9,056,200 B2 | 6/2015 | Uber, III et al. |
| 9,108,047 B2 | 8/2015 | Agamaite et al. |
| 9,153,350 B2 | 10/2015 | Mayfield |
| 9,173,995 B1 | 11/2015 | Tucker et al. |
| 9,242,119 B2 | 1/2016 | Agamaite et al. |
| 9,375,504 B2 | 6/2016 | Gowda et al. |
| 9,463,335 B2 | 10/2016 | Griffith et al. |
| 9,480,797 B1 | 11/2016 | Swantner et al. |
| 9,627,097 B2 | 4/2017 | Jackson et al. |
| 9,700,670 B2 | 7/2017 | Tucker et al. |
| 9,717,928 B2 | 8/2017 | Buck et al. |
| 9,855,390 B2 | 1/2018 | Bisegna et al. |
| 10,016,618 B2 | 7/2018 | Hirschman et al. |
| 10,039,889 B2 | 8/2018 | Cowan et al. |
| 10,052,499 B2 | 8/2018 | Kim |
| 10,512,721 B2 | 12/2019 | Swantner et al. |
| 10,668,221 B2 | 6/2020 | Bisegna et al. |
| 10,751,432 B2 | 8/2020 | Schimmoeller et al. |
| 10,842,896 B1 | 11/2020 | Mehra et al. |
| 10,881,848 B2 | 1/2021 | Ueda |
| 10,993,186 B2 | 4/2021 | Nagarajan et al. |
| 11,077,255 B2 | 8/2021 | Dahmani et al. |
| 11,081,250 B2 | 8/2021 | Harmon et al. |
| 11,179,518 B2 | 11/2021 | Gertsenchtein |
| 11,373,775 B2 | 6/2022 | Singh |
| 11,406,565 B2 | 8/2022 | Arnott et al. |
| 2003/0226981 A1 | 12/2003 | Schmidt |
| 2005/0234424 A1 | 10/2005 | Besing et al. |
| 2005/0277833 A1 | 12/2005 | Williams |
| 2007/0039156 A1 | 2/2007 | Reich |
| 2008/0161634 A1 | 7/2008 | Nemoto et al. |
| 2008/0200747 A1 | 8/2008 | Wagner et al. |
| 2008/0210892 A1 | 9/2008 | Wagner |
| 2008/0242915 A1 | 10/2008 | Jackson et al. |
| 2008/0265183 A1 | 10/2008 | Sirach |
| 2008/0277603 A1 | 11/2008 | Yanke et al. |
| 2008/0294096 A1 | 11/2008 | Uber, III et al. |
| 2009/0152477 A1 | 6/2009 | Powers et al. |
| 2009/0166370 A1 | 7/2009 | De Turk et al. |
| 2009/0275829 A1 | 11/2009 | Agarwal et al. |
| 2009/0292157 A1 | 11/2009 | Bruce et al. |
| 2009/0294700 A1 | 12/2009 | Fu et al. |
| 2011/0178359 A1 | 7/2011 | Hirschman et al. |
| 2011/0201867 A1 | 8/2011 | Wagner |
| 2011/0209764 A1* | 9/2011 | Uber ............... A61M 5/007 220/501 |
| 2013/0131422 A1 | 5/2013 | Vosniak et al. |
| 2015/0238918 A1 | 8/2015 | Khachaturian et al. |
| 2015/0335821 A1 | 11/2015 | Griffith et al. |
| 2017/0021193 A1 | 1/2017 | Griffith et al. |
| 2018/0296751 A1 | 10/2018 | Lefort et al. |
| 2019/0002363 A1 | 1/2019 | Frenvik et al. |
| 2019/0307949 A1 | 10/2019 | Hidem et al. |
| 2019/0348187 A1 | 11/2019 | Kamen |
| 2020/0262496 A1 | 8/2020 | Wilson et al. |
| 2021/0005337 A1 | 1/2021 | Kamen |
| 2021/0012917 A1 | 1/2021 | Nunn |
| 2021/0055431 A1 | 2/2021 | Knowland et al. |
| 2021/0077709 A1 | 3/2021 | Ben-David et al. |
| 2021/0138147 A1 | 5/2021 | Falkovich |
| 2021/0187186 A1 | 6/2021 | Uber, III |
| 2021/0299348 A1 | 9/2021 | Quirico et al. |
| 2021/0338922 A1 | 11/2021 | Uber, III et al. |
| 2022/0096733 A1 | 3/2022 | Holmqvist |
| 2022/0096751 A1 | 3/2022 | Byerly et al. |

FOREIGN PATENT DOCUMENTS

| | | |
|---|---|---|
| EP | 3003431 B1 | 3/2022 |
| KR | 20030087129 A | 11/2003 |
| WO | 02073628 A3 | 2/2003 |

(56) References Cited

FOREIGN PATENT DOCUMENTS

| WO | 2007032787 A3 | 5/2007 | |
|---|---|---|---|
| WO | 2009052048 A1 | 4/2009 | |
| WO | 2010039573 A2 | 4/2010 | |
| WO | 2013059563 A1 | 4/2013 | |
| WO | 2013184640 A2 | 12/2013 | |
| WO | 2014004978 A1 | 1/2014 | |
| WO | WO-2014188401 A1 * | 11/2014 | ............ A61M 5/007 |
| WO | 2014201358 A2 | 12/2014 | |
| WO | 2014210418 A1 | 12/2014 | |
| WO | 2015126526 A1 | 8/2015 | |
| WO | 2021222771 A1 | 11/2021 | |
| WO | 2021255045 A1 | 12/2021 | |
| WO | 2023212186 A1 | 11/2023 | |

\* cited by examiner

METHODS, STORAGE DEVICES, AND INFUSION SYSTEMS FOR THERAPEUTIC OR DIAGNOSTIC AGENTS

CROSS-REFERENCE TO RELATED APPLICATIONS

The present application is a Continuation Application of PCT International Application No. PCT/US2023/62890, filed Feb. 20, 2023, and claims priority to U.S. Provisional Application No. 63/312,145, filed on Feb. 21, 2022; and U.S. Provisional Application No. 63/312,148, filed on Feb. 21, 2022, the disclosures of which are incorporated by reference herein in their entirety.

BACKGROUND OF THE DISCLOSURE

Field of the Disclosure

The present disclosure relates to systems and methods for packaging, distribution, storage, administration and/or disposal of a radiopharmaceutical (e.g., a radioactive drug used for therapy or imaging). The present disclosure further relates to systems and methods for packaging, distribution, storage, administration and/or disposal of therapeutic or diagnostic agents requiring precise volumetric delivery from a controlled source.

Description of the Related Art

Radiopharmaceuticals can be utilized for targeted radionuclide therapy (TRT) or for diagnostic imaging. A radiopharmaceutical commonly includes a radioisotope (e.g., Ac-255, Lu-177, etc.), a targeting moiety or biovector (e.g., an antibody, a peptide, an antigen, small molecule, etc.), and optionally a chelator (e.g. DOTA, NOTA, DTPA, etc.) linked together into a single structure. In some cases, the TRT can be solely the radioisotope without a biovector or chelator when the radioisotope is one which the human body naturally takes up into tissues or organs. The radiopharmaceutical is configured to interact with a target protein on a cell, such as a cancer cell. The radiopharmaceutical can be mixed in a liquid form or a fluid form. In some examples or aspects, the radiopharmaceutical may be a solid particulate that is entrained in a fluid (e.g., a slurry that is suitable for injection into a patient). Administration is generally via intravenous administration into the systemic circulation.

Examples of TRTs can include targeted alpha therapies (TAT) or targeted beta therapies (TBT). Such therapies can be administered as mono therapies or in combination, such as via simultaneous or sequential administration. The radioactive therapeutic agent for TAT predominantly emits alpha radiation. The remainder of the emitted radiation from the radioactive therapeutic agent for TAT can include gamma radiation and/or beta radiation. A radioactive therapeutic agent for TBT predominantly emits beta radiation. The remainder of the emitted radiation for the radioactive therapeutic agent for TBT can include gamma radiation and/or alpha radiation. Examples of targeted alpha therapies include, without limitation, therapies based on thorium (Th-227) actinium (Ac-225), and lead (Pb-212). Examples of targeted beta therapies include therapies based on lutetium (Lu-177), copper (Cu-67), or iodine (I-131). Other examples of radioactive therapeutic agents can include an alpha therapeutic agent that utilizes radium (Ra) (e.g. the Ra-223 isotope, such as the XOFIGO® treatment provided by Bayer Health Care). Processes for the preparation, prepared solutions, and use of XOFIGO® are described in U.S. Pat. No. 6,635,234, the disclosure of which is incorporated by reference herein in its entirety.

Radiopharmaceuticals used in TRT can pose significant production, storage, distribution, administration, handling, and disposal challenges. Because the therapeutic agent is radioactive, it can pose a radiation exposure to human health. Moreover, given the decaying nature of radioactive agents, the longer it takes to make, process, and deliver a radiopharmaceutical to a patient, the less activity is present in the administered dose. There are substantial regulations that must be followed to keep the radioactive material safely stored and utilized that can affect how the agent can be stored and transported as well as who may use or administer the radioactive therapeutic agent. For example, such regulations may require a care provider to have hundreds of hours of training in order to be able to administer any TRT.

FIG. 1 illustrates a conventional supply chain for a TRT. Initially, the radiopharmaceutical is manufactured in bulk at a manufacturing facility and is loaded into bulk containers. A shipment of such containers is delivered to a nuclear pharmacy, where a nuclear pharmacist draws a dose, for example, into a syringe based on prescribed activity for a specific patient. That patient-ready dose is checked at the nuclear pharmacy in a dose calibrator to verify the prescribed dosing and assay. The dose is calibrated to the time of injection to assure that the dose has the necessary activity at the time of injection. The verified dose is then shipped to a treatment location, where it is again verified in a dose calibrator. At the treatment location, the dose usually has to be used within a certain number of hours of the dose draw before the dose is no longer suitable for patient use due to the half-life of the radioactive material. After administration, the used syringe is checked again in the dose calibrator to verify that the correct prescribed dose was administered to the patient.

As shown in FIG. 2, the process for diagnosing, referring, and treating a patient requires multiple processes and many different medical professionals. After a patient P is diagnosed by a doctor D, doctor D prescribes a dose of a radiopharmaceutical based on a dose regimen. That dose is filled by a nuclear pharmacist NP at a nuclear pharmacy before being delivered to an authorized user AU to verify the dose, administer the dose, and verify that the correct dose was delivered to the patient.

The conventional process for distribution and administration of TRT and other therapeutic or diagnostic agents that require precise volumetric delivery from a controlled source severely limits their applicability and use. After accounting for shipping, handling and patient scheduling, treatment locations will only have a limited time for administering a dose to a specific patient. The challenges imposed by variability in shipping, handling, and patient scheduling may have an impact on the efficacy of the TRT or other therapeutic or diagnostic agents, such as under-dosing at the time of delivery of the pharmaceutical to the patient. Due to these challenges associated with conventional systems and processes for distribution and administration of TRTs and other therapeutic or diagnostic agents that require precise volumetric delivery from a controlled source, there exists a need in the art for improved systems and processes for distribution, handling, administration, and disposal of such therapies.

SUMMARY OF THE DISCLOSURE

In view of the disadvantages of conventional systems and processes for distribution, handling, administration, and disposal of TRTs and other therapeutic or diagnostic agents, a better supply chain process is needed such that a treatment location can have TRTs available and ready to use for a longer period of time. Furthermore, improved systems and processes are needed to ensure that stored products are no longer patient specific. Instead, the treatment location can be provided equipment to help dose a treatment for any patient that may be in the location on any particular day so that there is more flexibility in how the stored product can be utilized at the treatment location such that an effective dose of the radiopharmaceutical can be delivered to the patient. Such patient-specific dosing is accomplished without the need for treatment location dose calibrators, thereby reducing or eliminating the need for manual measurements and handling within a designated hot lab. The dose, volume, and concentration may be accurately measured at the manufacturing or filling sites where it is much more efficient to use dosing and filling equipment, such as multiple dose calibrators with error detection and correction, automated handling of samples, automated recording of data, and accurate weighing or volume determination. The more accurate equipment and reduction or elimination of the chance for human error increases the reliability of the whole supply chain.

In some embodiments or aspects of the present disclosure, provided is a storage device configured to connect to a delivery system for delivering a therapeutic or diagnostic agent. The storage device may include: a housing having a chamber defined therein and a vessel positioned within the chamber. The vessel may have a distal end opposite a proximal end with an interior defined therebetween and configured for receiving the therapeutic or diagnostic agent. The proximal end of the vessel may have an access port for accessing the interior. The storage device further may have a door associated with the housing, the door being movable relative to the housing between a closed position and an open position. In the closed position, the door may cover an opening in the housing to enclose the chamber of the housing. In the open position, the door may reveal the opening in the housing for accessing the access port of the vessel. The storage device further may have a holder within the chamber of the housing and in contact with the vessel to fix the vessel relative to the housing such that the access port of the vessel is positioned at the opening in the housing. The door may be moveable between the closed position and the open position in response to actuation by an access mechanism of the delivery system.

In some embodiments or aspects of the present disclosure, the holder may include a contact element for contacting the distal end of the vessel and a plurality of tabs connected to the contact element and configured to engage an inner surface of the housing to fix the distal end of the vessel relative to the housing. The storage device further may include a plurality of ribs within the chamber of the housing and surrounding the opening. The plurality of ribs may be configured for fixing the proximal end of the vessel relative to the housing.

In some embodiments or aspects of the present disclosure, the storage device further may include a lock for locking the door in one of the open position and the closed position. A door cover may be connected to the housing, wherein the door cover encloses the door within a door chamber. The door cover may include a door access opening having a seal, and a vessel access opening, such as via a spike, positioned opposite the opening in the housing. The seal may be pierceable by the access mechanism of the delivery system.

In some embodiments or aspects of the present disclosure, the storage device further may include a label or a tag or data carrier on the housing that contains machine readable authenticatable data that includes at least one of product information, production information, prescription information, and shipping conditions information. The opening in the housing may be configured to receive a spike extending into the access port for accessing the therapeutic or diagnostic agent when the door is in the open position. In some embodiments or aspects, the therapeutic or diagnostic agent may be a radiopharmaceutical, wherein the housing includes shielding configured to prevent radiation from the radiopharmaceutical from being emitted out of the housing.

In some embodiments or aspects of the present disclosure, provided is an assembly configured to connect to a delivery system for delivering a therapeutic or diagnostic agent. The assembly may include a storage device containing the therapeutic or diagnostic agent, and a fluid cassette fluidly connectable to the storage device for accessing the therapeutic or diagnostic agent. The storage device may include a housing having a chamber defined therein and a vessel positioned within the chamber. The vessel may have an interior configured for receiving therapeutic or diagnostic agent and an access port for accessing the interior. The storage device further may include a door associated with the housing, the door movable relative to the housing between a closed position and an open position. In the closed position, the door may cover an opening in the housing to enclose the chamber of the housing. In the open position, the door may reveal the opening in the housing for accessing the access port of the vessel. The fluid cassette may include a spike, a metering device, and a fluid path set fluidly connecting the spike to the metering device. The fluid cassette further may include an enclosure enclosing the spike, the metering device, and the fluid path set. The storage device and the fluid cassette may be configured to connect to a delivery system such that the door of the storage device is accessible by an access mechanism of the delivery system and such that the spike and the metering device of the fluid cassette are accessible by a delivery mechanism of the delivery system.

In some embodiments or aspects of the present disclosure, the spike of the fluid cassette may be insertable into an access port of the vessel when the door is moved to the open position to fluidly connect the metering device to the vessel via the fluid path set. The fluid path set may include one or more valves operable by the delivery mechanism of the delivery system for regulating fluid flow through the fluid path element. The fluid cassette may be connectable to a saline source.

In some embodiments or aspects of the present disclosure, the storage device may include a guide mechanism configured for positioning the storage device in a desired orientation relative to the fluid cassette. The guide mechanism may include one or more geometric features on the storage device. The one or more geometric features may be configured to mate with the corresponding one or more geometric features on the fluid cassette. The one or more geometric features may prevent mating between incompatible system components.

In some embodiments or aspects of the present disclosure, an outlet of the metering device of the fluid cassette may be configured to connect to an infusion set for delivering a dose of the therapeutic or diagnostic agent from the vessel to the infusion set. The storage device further may include a label or a tag on the housing that contains machine readable authenticatable data that includes at least one of product information, production information, prescription information, and shipping conditions information. The therapeutic or diagnostic agent may be a radiopharmaceutical, wherein the housing includes shielding configured to prevent significant radiation from the radiopharmaceutical from being emitted out of the housing.

In some embodiments or aspects of the present disclosure, provided is a delivery system for delivering a therapeutic or diagnostic agent. The delivery system may include an injector having a delivery mechanism and an access mechanism, and a fluid delivery assembly removably connectable to the injector. The fluid delivery assembly may include a storage device containing the therapeutic or diagnostic agent, and a fluid cassette fluidly connectable to the storage device for accessing the therapeutic or diagnostic agent. The storage device may include a housing having a chamber defined therein, and a vessel positioned within the chamber. The vessel may have an interior configured for receiving therapeutic or diagnostic agent and an access port for accessing the interior. The storage device further may include a door associated with the housing, the door being movable relative to the housing via the access mechanism of the injector between a closed position and an open position. In the closed position, the door may cover an opening in the housing to enclose the chamber of the housing. In the open position, the door may reveal the opening in the housing for accessing the access port of the vessel. The fluid cassette may include a spike, a metering device, and a fluid path set fluidly connecting the spike to the metering device. The fluid cassette further may include an enclosure enclosing the spike, the metering device, and the fluid path set. The spike and the metering device of the fluid cassette may be accessible by the delivery mechanism of the injector for fluidly connecting the interior of the vessel with the metering device via the fluid path set.

In some embodiments or aspects of the present disclosure, the delivery system further includes an injector controller configured to determine a dose of the therapeutic or diagnostic agent to be drawn from the vessel into the metering device based on machine readable authenticated data on the storage device. The injector controller may be further configured to determine a dose of the therapeutic or diagnostic agent to be drawn from the vessel into the metering device based on at least one patient parameter. The injector controller may be connected to a hospital network system, hospital enterprise system, or other healthcare network. The injector controller may include a plurality of dosing algorithms for different pre-defined therapies or diagnostic procedures.

In some embodiments or aspects of the present disclosure, the fluid path set may include one or more valves operable by the delivery mechanism of the delivery system for regulating fluid flow through the fluid path element. The fluid cassette may be connectable to a saline or other flushing fluid source. An outlet of the metering device of the fluid cassette may be configured to connect to an infusion set for delivering a dose of therapeutic or diagnostic agent from the vessel to the infusion set. The storage device may be configured to be removably or non-removably connectable to the fluid cassette.

In some embodiments or aspects of the present disclosure, provided is an inventory device for managing storage and disposal of used therapeutic or diagnostic agent. The inventory device may include a cart having a storage compartment that is accessible via a lockable door. The storage compartment may be configured to store one or more disposal containers. Each disposal container may include a storage device with a housing having a chamber defined therein, and a vessel positioned within the chamber of the housing. The vessel may be configured to store a radiopharmaceutical within an interior thereof. A door may be connected to the housing and be movable between an open position and a closed position. In the closed position, the door may entirely enclose the chamber of the housing. The device further may include a fluid cassette having a spike and a metering device. The storage device may be affixed to the fluid cassette such that the spike is inserted into the vessel to fluidly connect the metering device to the vessel. The metering device may be connected to an infusion set used for injecting a dose of the radiopharmaceutical. The infusion set, the storage device, and the fluid cassette may be retained within the disposal container.

In some embodiments or aspects of the present disclosure, the cart may include at least one indicator associated with the storage compartment to indicate whether any of the one or more disposal containers have been stored for a pre-selected storage time period so that a radioactive component of the used therapeutic or diagnostic agent has decayed to a pre-selected safety threshold level. The cart may include wheels having a wheel lock configured to prevent unauthorized or unintended movement of the cart. The wheel lock may be an electronic lock in communication with a controller. The wheel lock may be a mechanical lock having a key or other mechanical lock mechanism. The wheel lock may be operatively connected with the lockable door so that the wheels are unlocked and rollable only after the lockable door is unlocked.

In some embodiments or aspects of the present disclosure, provided is a process for manufacture and distribution of a therapeutic or diagnostic agent. The process may include filling a vessel with the therapeutic or diagnostic agent, positioning the vessel within a chamber of a storage device having a housing, closing the storage device so that the housing fully encloses the vessel within the chamber, shipping the storage device to an administration facility, opening a door of the storage device using an access mechanism of a delivery system, disinfecting an access port of the vessel using a disinfection mechanism of the delivery system, and accessing the therapeutic or diagnostic agent within the vessel via the access port using the delivery system.

In some embodiments or aspects of the present disclosure, accessing therapeutic or diagnostic agent may include piercing the access port using a spike of a cassette connected to the storage device. The process further may include reading a label or a tag on the storage device to determine at least one of product information, production information, prescription information, and shipping conditions information. The process further may include disinfecting the access port by emitting ultraviolet light or outputting a disinfecting material.

In some embodiments or aspects of the present disclosure, provided is a process for storing and disposing of used therapeutic or diagnostic agent. The process may include collecting a storage device that retains a vessel with a remaining portion of the therapeutic or diagnostic agent, a cassette to which the storage device is fluidly connected, and an infusion set for positioning in a disposal container. The process further may include placing a label, tag, or other indicia on the disposal container to indicate date of use; positioning the disposal container having the storage device, the cassette, and the infusion set therein into a storage compartment; and indicating the disposal container is safe to dispose of after a pre-selected decay time period has elapsed. The process further may include reading the label or other indicia to determine at least one of product information, production information, prescription information, and shipping conditions information.

In some embodiments or aspects of the present disclosure, provided is a process for delivering a dose of a therapeutic or diagnostic agent. The process may include inserting a therapeutic or diagnostic agent into a vessel; positioning the vessel within a chamber of a storage device having a housing; closing a door of the storage device so that the housing fully encloses the vessel within the chamber to shield radiation emitted by the radiopharmaceutical from being emitted out of the housing for transportation and storage of the radiopharmaceutical; determining a dose of the radiopharmaceutical for a patient based on manufacturing information of the radiopharmaceutical included with the storage device; and unlocking the door of the storage device to open the housing to access the radiopharmaceutical within the vessel and inject the determined dose into a patient.

In some embodiments or aspects of the present disclosure, accessing the therapeutic or diagnostic agent may include piercing the access port of the vessel using a spike of a cassette connected to the storage device. The process further may include reading a label or a tag on the storage device to determine at least one of product information, production information, prescription information, and shipping conditions information. The process further may include disinfecting an access port of the vessel. Disinfecting the access port may include emitting ultraviolet light or outputting a disinfecting material.

Additional embodiments or aspects of the systems and processes described herein are detailed in one or more of the following clauses:

Clause 1: A storage device configured to connect to a delivery system for delivering a therapeutic or diagnostic agent, the storage device comprising: a housing having a chamber defined therein; a vessel positioned within the chamber, the vessel having a distal end opposite a proximal end with an interior defined therebetween and configured for receiving the therapeutic or diagnostic agent, the proximal end having an access port for accessing the interior; a door associated with the housing, the door movable relative to the housing between a closed position and an open position, wherein, in the closed position, the door covers an opening in the housing to enclose the chamber of the housing, and wherein, in the open position, the door reveals the opening in the housing for accessing the access port of the vessel; and a holder within the chamber of the housing and in contact with the vessel to fix the vessel relative to the housing such that the access port of the vessel is positioned at the opening in the housing; wherein the door is moveable between the closed position and the open position in response to actuation by an access mechanism of the delivery system.

Clause 2: The storage device according to clause 1, wherein the holder comprises a contact element for contacting the distal end of the vessel and a plurality of tabs connected to the contact element and configured to engage an inner surface of the housing to fix the distal end of the vessel relative to the housing.

Clause 3: The storage device according to clause 1 or 2, further comprising a plurality of ribs within the chamber of the housing and surrounding the opening, wherein the plurality of ribs is configured for fixing the proximal end of the vessel relative to the housing.

Clause 4: The storage device according to any of clauses 1 to 3, further comprising a lock for locking the door in one of the open positon and the closed position.

Clause 5: The storage device according to any of clauses 1 to 4, further comprising a door cover connected to the housing, wherein the door cover encloses the door within a door chamber.

Clause 6: The storage device according to any of clauses 1 to 5, wherein the door cover comprises a door access opening having a seal, and a vessel access opening positioned opposite the opening in the housing.

Clause 7: The storage device according to clause 6, wherein the seal is pierceable by the access mechanism of the delivery system.

Clause 8: The storage device according to any of clauses 1 to 7, further comprising a label or a tag on the housing that contains machine readable authenticatable data that includes at least one of product information, production information, prescription information, and shipping conditions information.

Clause 9: The storage device according to any of clauses 1 to 8, wherein the opening in the housing is configured to receive a spike extending into the access port for accessing the therapeutic or diagnostic agent when the door is in the open position.

Clause 10: The storage device according to any of clauses 1 to 9, wherein the therapeutic or diagnostic agent is a radiopharmaceutical, and wherein the housing comprises shielding configured to prevent radiation from the radiopharmaceutical from being emitted out of the housing.

Clause 11: An assembly configured to connect to a delivery system for delivering a therapeutic or diagnostic agent, the assembly comprising: a storage device containing the therapeutic or diagnostic agent; and a fluid cassette fluidly connectable to the storage device for accessing the therapeutic or diagnostic agent, wherein the storage device comprises: a housing having a chamber defined therein; a vessel positioned within the chamber, the vessel having an interior configured for receiving the therapeutic or diagnostic agent and an access port for accessing the interior; and a door associated with the housing, the door movable relative to the housing between a closed position and an open position, wherein, in the closed position, the door covers an opening in the housing to enclose the chamber of the housing, and wherein, in the open position, the door reveals the opening in the housing for accessing the access port of the vessel, wherein the fluid cassette comprises: a spike, a metering device, and a fluid path set fluidly connecting the spike to the metering device; and an enclosure enclosing the spike, the metering device, and the fluid path set, and wherein the storage device and the fluid cassette are configured to connect to a delivery system such that the door of the storage device is accessible by an access mechanism of the delivery system and such that the spike and the metering device of the fluid cassette are accessible by a delivery mechanism of the delivery system.

Clause 12: The assembly according to clause 11, wherein the vessel access member of the fluid cassette is insertable into the access port of the vessel when the door is moved to the open position to fluidly connect the metering device to the vessel via the fluid path set.

Clause 13: The assembly according to clause 11 or 12, wherein the fluid path set comprises one or more valves operable by the delivery mechanism of the delivery system for regulating fluid flow through the fluid path element.

Clause 14: The assembly according to any of clauses 11 to 13, wherein the fluid cassette is connectable to a saline source.

Clause 15: The assembly according to any of clauses 11 to 14, wherein the storage device comprises a guide mechanism configured for positioning the storage device in a desired orientation relative to the fluid cassette.

Clause 16: The assembly according to clause 15, wherein the guide mechanism comprises one or more geometric features on the storage device, and wherein the one or more geometric features are configured to mate with the corresponding one or more geometric features on the fluid cassette.

Clause 17: The assembly according to any of clauses 11 to 16, wherein an outlet of the metering device of the fluid cassette is configured to connect to an infusion set for delivering a dose of the therapeutic or diagnostic agent from the vessel to the infusion set.

Clause 18: The assembly according to any of clauses 11 to 17, further comprising a label or a tag on the housing that contains machine readable authenticatable data that includes at least one of product information, production information, prescription information, and shipping conditions information.

Clause 19: The assembly according to any of clauses 11 to 18, wherein the therapeutic or diagnostic agent is a radiopharmaceutical, and wherein the housing comprises shielding configured to prevent radiation from the radiopharmaceutical from being emitted out of the housing.

Clause 20: A delivery system for delivering a therapeutic or diagnostic agent, the delivery system comprising: an injector having a delivery mechanism and an access mechanism; and a fluid delivery assembly removably connectable to the injector, the fluid delivery assembly comprising: a storage device containing the therapeutic or diagnostic agent; and a fluid cassette fluidly connectable to the storage device for accessing the therapeutic or diagnostic agent, wherein the storage device comprises: a housing having a chamber defined therein; a vessel positioned within the chamber, the vessel having an interior configured for receiving the therapeutic or diagnostic agent and an access port for accessing the interior; and a door associated with the housing, the door movable relative to the housing via the access mechanism of the injector between a closed position and an open position, wherein, in the closed position, the door covers an opening in the housing to enclose the chamber of the housing, and wherein, in the open position, the door reveals the opening in the housing for accessing the access port of the vessel, wherein the fluid cassette comprises: a vessel access member, a metering device, and a fluid path set fluidly connecting the vessel access member to the metering device; and an enclosure enclosing the vessel access member, the metering device, and the fluid path set, and wherein the vessel access member and the metering device of the fluid cassette are accessible by the delivery mechanism of the injector for fluidly connecting the interior of the vessel with the metering device via the fluid path set.

Clause 21: The delivery system according to clause 20, further comprising an injector controller configured to determine a dose of the therapeutic or diagnostic agent to be drawn from the vessel into the metering device based on machine readable authenticated data on the storage device.

Clause 22: The delivery system according to clause 21, wherein the injector controller is further configured to determine a dose of the therapeutic or diagnostic agent to be drawn from the vessel into the metering device based on at least one patient parameter.

Clause 23: The delivery system according to clause 21 or 22, wherein the injector controller is connected to a hospital network system.

Clause 24: The delivery system according to any of clauses 21 to 23, wherein the injector controller comprises a plurality of dosing algorithms for different pre-defined therapies or diagnostic procedures.

Clause 25: The delivery system according to any of clauses 20 to 24, wherein the fluid path set comprises one or more valves operable by the delivery mechanism of the delivery system for regulating fluid flow through the fluid path element.

Clause 26: The delivery system according to any of clauses 20 to 25, wherein the fluid cassette is connectable to a saline source.

Clause 27: The assembly according to any of clauses 20 to 26, wherein an outlet of the metering device of the fluid cassette is configured to connect to an infusion set for delivering a dose of the therapeutic or diagnostic agent from the vessel to the infusion set.

Clause 28: The assembly according to any of clauses 20 to 27, wherein the storage device is configured to be removably or non-removably connectable to the fluid cassette.

Clause 29: The delivery system according to any of clauses 20 to 28, further comprising a label or a tag on the housing that contains machine readable authenticatable data that includes at least one of product information, production information, prescription information, and shipping conditions information.

Clause 30: The delivery system according to any of clauses 20 to 29, wherein the therapeutic or diagnostic agent is a radiopharmaceutical, and wherein the housing comprises shielding configured to prevent radiation from the radiopharmaceutical from being emitted out of the housing.

Clause 31: An inventory device for managing storage and disposal of used therapeutic or diagnostic agent, the inventory device comprising: a cart having a storage compartment that is accessible via a lockable door, the storage compartment configured to store one or more disposal containers, each disposal container comprising: a storage device comprising: a housing having a chamber defined therein; a vessel positioned within the chamber of the housing, the vessel configured to store a radiopharmaceutical within an interior thereof; a door connected to the housing, the door movable between an open position and a closed position, wherein, in the closed position, the door entirely encloses the chamber of the housing; and a fluid cassette comprising a vessel access member and a metering device, the storage device affixed to the fluid cassette such that the vessel access member is inserted into the vessel to fluidly connect the metering device to the vessel, the metering device being connected to an infusion set used for injecting a dose of the radiopharmaceutical, wherein the infusion set, the storage device, and the fluid cassette are retained within the disposal container.

Clause 32: The inventory device according to clause 31, wherein the cart comprises at least one indicator associated with the storage compartment to indicate whether any of the one or more disposal containers have been stored for a pre-selected storage time period so that a radioactive component of the used therapeutic or diagnostic agent has decayed to a pre-selected safety threshold level.

Clause 33: The inventory device according to clause 31 or 32, wherein the cart comprises wheels having a wheel lock configured to prevent unauthorized movement of the cart.

Clause 34: The inventory device according to clause 33, wherein the wheel lock is an electronic lock in communication with a controller.

Clause 35: The inventory device according to clause 33 or 34, wherein the wheel lock is a mechanical lock having a key or other mechanical lock mechanism.

Clause 36: The inventory device according to any of clauses 33 to 35, wherein the wheel lock is operatively connected with the lockable door so that the wheels are unlocked and rollable only after the lockable door is unlocked.

Clause 37: A process for manufacture and distribution of a therapeutic or diagnostic agent, the process comprising: filling a vessel with the therapeutic or diagnostic agent; positioning the vessel within a chamber of a storage device having a housing; closing the storage device so that the housing fully encloses the vessel within the chamber; shipping the storage device to an administration facility; opening a door of the storage device using an access mechanism of a delivery system; disinfecting an access port of the vessel using a disinfection mechanism of the delivery system; and accessing the therapeutic or diagnostic agent within the vessel via the access port using the delivery system.

Clause 38: The process according to clause 37, wherein accessing the therapeutic or diagnostic agent comprises piercing the access port using a vessel access member of a cassette connected to the storage device.

Clause 39: The process according to clause 37 or 38, further comprising reading a label or a tag on the storage device to determine at least one of product information, production information, prescription information, and shipping conditions information.

Clause 40: The process according to any of clauses 37 to 39, wherein disinfecting the access port comprises emitting ultraviolet light or outputting a disinfecting material.

Clause 41: A process for storing and disposing of used therapeutic or diagnostic agent, the process comprising: collecting a storage device that retains a vessel with a remaining portion of the therapeutic or diagnostic agent, a cassette to which the storage device is fluidly connected, and an infusion set for positioning in a disposal container; placing a label, tag, or other indicia on the disposal container to indicate date of use; positioning the disposal container having the storage device, the cassette, and the infusion set therein into a storage compartment; and indicating the disposal container is safe to dispose of after a pre-selected decay time period has elapsed.

Clause 42: The process according to clause 41, further comprising reading the label, tag, or other indicia to determine at least one of product information, production information, prescription information, and shipping conditions information.

Clause 43: A process for delivering a dose of a therapeutic or diagnostic agent, the process comprising: inserting a therapeutic or diagnostic agent into a vessel; positioning the vessel within a chamber of a storage device having a housing; closing a door of the storage device so that the housing fully encloses the vessel within the chamber to shield radiation emitted by the radiopharmaceutical from being emitted out of the housing for transportation and storage of the radiopharmaceutical; determining a dose of the radiopharmaceutical for a patient based on manufacturing information of the radiopharmaceutical included with the storage device; and unlocking the door of the storage device to open the housing to access the radiopharmaceutical within the vessel and inject the determined dose into a patient.

Clause 44: The process according to clause 43, wherein accessing the therapeutic or diagnostic agent comprises piercing the access port using a vessel access member of a cassette connected to the storage device.

Clause 45: The process according to clause 43 or 44, further comprising reading a label or a tag on the storage device to determine at least one of product information, production information, prescription information, and shipping conditions information.

Clause 46: The process according to any of clauses 43 to 45, further comprising disinfecting an access port of the vessel.

Clause 47: The process according to clause 46, wherein disinfecting the access port comprises emitting ultraviolet light or outputting a disinfecting material.

Clause 48: A storage device configured to connect to a delivery system, the storage device comprising: a housing having a chamber defined therein; a vessel positioned within the chamber, the vessel containing a radiopharmaceutical within an interior thereof, wherein the radiopharmaceutical is a therapeutically or prophylactically effective amount of a free metallic cation of the alkaline earth metal radium-223; a door associated with the housing, the door movable relative to the housing between a closed position and an open position, wherein, in the closed position, the door covers an opening in the housing to enclose the chamber of the housing, and wherein, in the open position, the door reveals the opening in the housing for accessing the access port of the vessel; and a holder within the chamber of the housing and in contact with the vessel to fix the vessel relative to the housing such that the access port of the vessel is positioned at the opening in the housing; wherein the door is moveable between the closed position and the open position in response to actuation by an access mechanism of the delivery system.

Clause 49: An assembly configured to connect to a delivery system for delivering a radiopharmaceutical, the assembly comprising: a storage device containing the therapeutic or diagnostic agent; and a fluid cassette fluidly connectable to the storage device for accessing the therapeutic or diagnostic agent, wherein the storage device comprises: a housing having a chamber defined therein; a vessel positioned within the chamber, the vessel containing a radiopharmaceutical within an interior thereof, wherein the radiopharmaceutical is a therapeutically or prophylactically effective amount of a free metallic cation of the alkaline earth metal radium-223; a door associated with the housing, the door movable relative to the housing between a closed position and an open position, wherein, in the closed position, the door covers an opening in the housing to enclose the chamber of the housing, and wherein, in the open position, the door reveals the opening in the housing for accessing the access port of the vessel, wherein the fluid cassette comprises: a vessel access member, a metering device, and a fluid path set fluidly connecting the vessel access member to the metering device; and an enclosure enclosing the vessel access member, the metering device, and the fluid path set, and wherein the storage device and the fluid cassette are configured to connect to a delivery system such that the door of the storage device is accessible by an access mechanism of the delivery system and such that the vessel access member and the metering device of the fluid cassette are accessible by a delivery mechanism of the delivery system.

Clause 50: A delivery system for delivering a therapeutic or diagnostic agent, the delivery system comprising: an injector having a delivery mechanism and an access mechanism; and a fluid delivery assembly removably connectable to the injector, the fluid delivery assembly comprising: a storage device containing the therapeutic or diagnostic agent; and a fluid cassette fluidly connectable to the storage device for accessing the therapeutic or diagnostic agent, wherein the storage device comprises: a housing having a chamber defined therein; a vessel positioned within the chamber of the housing, the vessel containing a radiopharmaceutical within an interior thereof, wherein the radiopharmaceutical is a therapeutically or prophylactically effective amount of a free metallic cation of the alkaline earth metal radium-223; and a door associated with the housing, the door movable relative to the housing via the access mechanism of the injector between a closed position and an open position, wherein, in the closed position, the door covers an opening in the housing to enclose the chamber of the housing, and wherein, in the open position, the door reveals the opening in the housing for accessing the access port of the vessel, wherein the fluid cassette comprises: a vessel access member, a metering device, and a fluid path set fluidly connecting the vessel access member to the metering device; and an enclosure enclosing the vessel access member, the metering device, and the fluid path set, and wherein the vessel access member and the metering device of the fluid cassette are accessible by the delivery mechanism of the injector for fluidly connecting the interior of the vessel with the metering device via the fluid path set, wherein the injector comprises an injector controller configured to determine a dose of the radiopharmaceutical based on manufacturing data attached to the housing of the storage device, the injector controller communicatively connected to the injector to control the injector for injecting the dose so that the injected dose that is received by a patient is the dose determined by the injector controller based on the manufacturing data attached to the housing of the storage device.

Clause 51: An inventory device for managing storage and disposal of used radiopharmaceutical, the inventory device comprising: a cart having shelving that is accessible via a lockable door, the shelving configured to store disposal containers, each disposal container comprising: a storage device comprising: a housing having a chamber defined therein; a vessel positioned within the chamber of the housing, the vessel configured to store a radiopharmaceutical within an interior thereof; a door connected to the housing, the door movable between an open position and a closed position, wherein, in the closed position, the door entirely encloses the chamber of the housing; and a fluid cassette comprising a vessel access member and a metering device, the storage device affixed to the fluid cassette such that the vessel access member is inserted into the vessel to fluidly connect the metering device to the vessel, the metering device being connected to an infusion set used for injecting a dose of the radiopharmaceutical, wherein the infusion set, the storage device, and the fluid cassette are retained within the disposal container, wherein the cart comprises indicators for the shelving to indicate which disposal containers have been stored for a pre-selected storage time period so that the radiopharmaceutical has decayed so radioactivity of the material is at or below a pre-selected safety threshold level.

Clause 52: A process for manufacture and distribution of a radiopharmaceutical for a targeted radionuclide therapy or a diagnostic imaging service, the process comprising: filling a vessel with a radiopharmaceutical for a TRT or the diagnostic imaging service, wherein the radiopharmaceutical is a therapeutically or prophylactically effective amount of a free metallic cation of the alkaline earth metal radium-223; positioning the vessel within a chamber of a storage device having a housing; closing the storage device so that the housing fully encloses the vessel within the chamber; shipping the storage device to an administration facility; opening a door of the storage device using an access mechanism of a delivery system; disinfecting an access port of the vessel using a disinfection mechanism of the delivery system; and accessing the radiopharmaceutical within the vessel via the access port using the delivery system.

Clause 53: A process for storing and disposing of radiopharmaceutical used in a targeted radionuclide therapy or a diagnostic imaging service, the process comprising: collecting a storage device that retains a vessel with a remaining portion of radiopharmaceutical, a cassette to which the storage device is connected, and an infusion set for positioning in a disposal container; placing a label, tag, or other indicia on the disposal container to indicate date of use; positioning the disposal container having the storage device, the cassette, and the infusion set therein into a storage compartment; and indicating the disposal container is safe to dispose of after a pre-selected decay time period has elapsed, wherein the radiopharmaceutical is a therapeutically or prophylactically effective amount of a free metallic cation of the alkaline earth metal radium-223.

Clause 54: A process for injecting a dose of a targeted radionuclide therapy or a diagnostic imaging service, the process comprising: inserting a radiopharmaceutical into a vessel, wherein the radiopharmaceutical is a therapeutically or prophylactically effective amount of a free metallic cation of the alkaline earth metal radium-223; positioning the vessel within a chamber of a storage device having a housing; closing a door of the storage device so that the housing fully encloses the vessel within the chamber to shield radiation emitted by the radiopharmaceutical from being emitted out of the housing for transportation and storage of the radiopharmaceutical; determining a dose of the radiopharmaceutical for a patient based on manufacturing information of the radiopharmaceutical included with the storage device; and unlocking the door of the storage device to open the housing to access the radiopharmaceutical within the vessel and inject the determined dose into a patient.

Clause 55: A radiopharmaceutical dosing injection system for a therapeutically or prophylactically effective amount of a free metallic cation of radium-223, according to any preceding clause.

Clause 56: An inventory device for the managing, storage and disposal of a therapeutically or prophylactically effective amount of a free metallic cation of radium-223, according to any preceding clause.

Clause 57: A process further including a therapeutically or prophylactically effective amount of a free metallic cation of radium-223, according to any preceding clause.

BRIEF DESCRIPTION OF THE DRAWINGS

In FIGS. 1-39, like characters refer to the same components and elements, as the case may be, unless otherwise stated.

DETAILED DESCRIPTION

Figure 1:
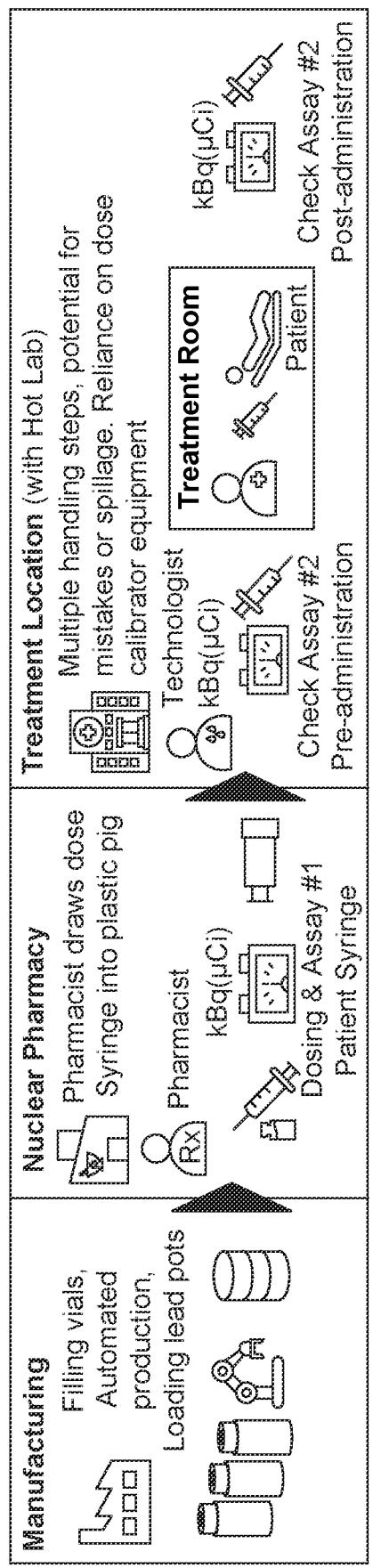
FIG. 1 is a representative schematic of a conventional supply chain for a radioactive therapeutic agent configured for use with TRT according to the prior art.
Figure 2:
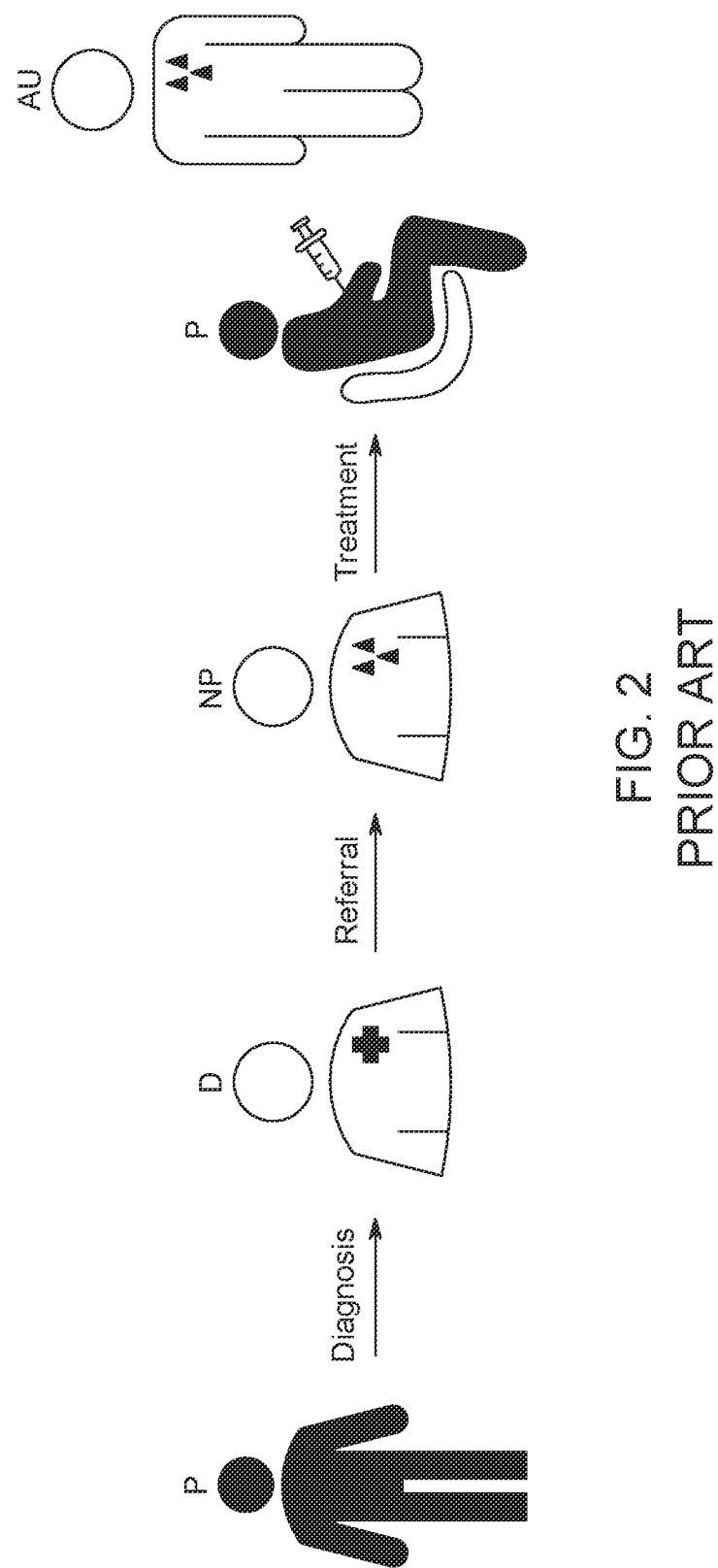
FIG. 2 is a representative schematic of a conventional process for administration of TRT according to the prior art.

As used herein, the singular form of "a", "an", and "the" include plural referents unless the context clearly dictates otherwise.

Spatial or directional terms, such as "left", "right", "inner", "outer", "above", "below", and the like, relate to the embodiments or aspects as shown in the drawing figures and are not to be considered as limiting as the embodiments or aspects can assume various alternative orientations.

All numbers used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to".

The term "not greater than" is synonymous with "less than or equal to".

Some non-limiting embodiments or aspects may be described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

As used herein, "at least one of" is synonymous with "one or more of". For example, the phrase "at least one of A, B, or C" means any one of A, B, or C, or any combination of any two or more of A, B, or C. For example, "at least one of A, B, or C" includes A alone; or B alone; or C alone; or A and B; or A and C; or B and C; or all of A, B, and C.

The term "includes" is synonymous with "comprises".

When used in relation to a component of a fluid delivery system such as a fluid reservoir, a syringe, or a fluid line, the term "distal" refers to a portion of said component nearest to a patient. When used in relation to a component of an injector system such as a fluid reservoir, a syringe, or a fluid line, the term "proximal" refers to a portion of said component nearest to the injector of the injector system (i.e. the portion of said component farthest from the patient). When used in relation to a component of a fluid delivery system such as a fluid reservoir, a syringe, or a fluid line, the term "upstream" refers to a direction away from the patient and towards the injector in relation to the normal flow of fluid of the injector system. When used in relation to a component of a fluid delivery system such as a fluid reservoir, a syringe, or a fluid line, the term "downstream" refers to a direction towards the patient and away from the injector in relation to the normal flow of fluid of the fluid delivery system.

As used herein, the terms "communication" and "communicate" may refer to the reception, receipt, transmission, transfer, provision, and/or the like, of information (e.g., data, signals, messages, instructions, commands, and/or the like).

The term "radiopharmaceutical", as used herein, refers to a pharmaceutical comprising a radionuclide. Radiopharmaceuticals, as discussed herein, are preferably configured to be administered intravenously (i.v.). There are two types of radiopharmaceuticals: diagnostic (or imaging) and therapeutic radiopharmaceuticals, although in some instances, therapeutic radiopharmaceuticals may be used for both. For example, so TRSs may emit gamma radiation which may be used for dosimetry assessments and/or diagnostic purposes. Radiopharmaceutical generally used for imaging, such as the positron emitters, may also be used for therapy. See for example Hioki, T., Gholami, Y. H., McKelvey, K. J. et al. Overlooked potential of positrons in cancer therapy. Sci Rep 11, 2475 (2021).

The term "diagnostic radiopharmaceutical" or "imaging radiopharmaceutical", as used herein, comprises Gamma emitting imaging radiopharmaceuticals for use in SPECT or SPECT/CT imaging and/or Positron emitting imaging radiopharmaceuticals for use in PET or PET/CT imaging. Examples of Gamma emitting imaging radiopharmaceuticals include, without limitation, technetium (Tc-99m), iodine (I-123), indium (In-111), gallium (Ga-67), or rhenium (Re-186). Examples of Positron emitting imaging radiopharmaceuticals include, without limitation, fluorine (F-18), gallium (Ga-68), zirconium (Zr-89), iodine (I-124), copper (Cu-64), rubidium (Rb-82) or yttrium (Y-86).

The term "therapeutic radiopharmaceutical", as used herein, comprises Beta Therapeutic Radiopharmaceuticals, Alpha Therapeutic Radiopharmaceuticals, Positron Therapeutic Radiopharmaceuticals, Auger Therapeutic Radiopharmaceuticals, Gamma Therapeutic Radiopharmaceuticals, and/or combinations thereof.

As used herein, the term "therapeutic or diagnostic agent" refers to any diagnostic pharmaceutical, imaging pharmaceutical, a radiotherapy or chemotherapy pharmaceutical, a therapeutic pharmaceutical, or any other liquid or powder (once reconstituted) used in a therapeutic or diagnostic capacity that requires precise dose delivery from a controlled source, where dose is the amount of active ingredient. The dose delivery may be accomplished by precise volumetric delivery.

All radiation shielding is fractional or partial. Adding a half value layer of thickness to the shielding reduces the transmitted radiation by a factor of two. The effectiveness of shielding depends upon the energy of the radiation being shielded. Thus, terms such as "block", "stop", or "prevent" radiation transmission or radiation release indicate a reduction in transmitted or released radiation to an acceptable level. This acceptable level may be dependent upon local regulations, requirements, policies, or preferences. The many materials used for shielding and the guidelines involved are well known to those in the health physics field.

The disclosure comprises, consists of, or consists essentially of the following examples of the embodiments or aspects, in any combination. Various examples of the disclosure may be discussed separately. However, it is to be understood that this is simply for ease of illustration and discussion. In the practice of the disclosure, one or more aspects of the disclosure described in one example can be combined with one or more aspects of the disclosure described in one or more of the other examples.

In various embodiments or aspects, the present disclosure is directed to systems and processes for distribution, storage, administration, and disposal of a radiopharmaceutical therapeutic agent. The present disclosure is also directed to systems and processes for distribution, storage, administration, and disposal of other therapeutic or diagnostic agents that require precise volumetric delivery from a controlled source, such as chemotherapy pharmaceuticals. As discussed herein, conventional processes for distribution and administration of therapeutic or diagnostic agents that require precise volumetric delivery from a controlled source severely limits their applicability and use. After accounting for shipping, handling and patient scheduling, treatment locations have a limited time for administering a dose to a specific patient. The systems and processes described herein provide an improvement in the distribution, storage, administration, and disposal of therapeutic or diagnostic agents to allow increased time for administering a dose to a specific patient.

As discussed in various embodiments or aspects of the present disclosure, a storage device can be configured to store a radioactive therapeutic agent from a point of production for shipment and storage at a treatment facility so the radioactive therapeutic agent is fully enclosed and encased until use. Each of the storage devices can be sized, shaped, and configured to provide radiation shielding appropriate to the radioactive isotope and dose being stored. The storage devices can also be further packaged and surrounded by additional shielding. The storage device housing is configured to be opened and unsealed only at the treatment site utilizing a dedicated device, as described herein. In some embodiments or aspects, a storage device can be configured to store a therapeutic or diagnostic agent other than a radiopharmaceutical from the point of production for shipment and storage at a treatment facility so the therapeutic or diagnostic agent is fully enclosed and encased until use.

As discussed in various embodiments or aspects of the present disclosure, a system can be provided to include a radioactive therapeutic agent injection/infusion system specifically adapted for accessing the therapeutic or diagnostic agent stored in a storage device so the material is only accessible for administering to a patient via the injection/infusion system and is otherwise prevented from being administered if the storage device is not recognized as an untampered storage device. The storage device can be configured so that only the injection/infusion system can open the storage device to access the therapeutic or diagnostic agent for injecting the agent into a patient. When the therapeutic or diagnostic agent is a radiopharmaceutical, the combination of the storage device and injection/infusion system can help ensure the radioactive material remains fully sealed and enclosed from the time of production until use. Further, the injection/infusion system and storage device once used can remain connected and unopenable to facilitate safe containment and disposal of radioactive waste after use.

As discussed in various embodiments or aspects of the present disclosure, a system and process can be provided to calculate the dose for a specific patient based on the therapeutic or diagnostic agent being administered, the patient's parameters, such as patient weight, the known manufacturing and/or calibration date, known radioactivity or other property of the therapeutic or diagnostic agent at the time of manufacture, and known current date and time to determine the appropriate dose for the patient for injecting the volume of the therapeutic or diagnostic agent that corresponds to the calculated activity dose of the agent into the patient for the treatment. When the therapeutic or diagnostic agent is a radiopharmaceutical, the unused portion of the radiopharmaceutical and other components that contacted that radiopharmaceutical that may be contaminated can be stored in a disposal container for storage until the radioactivity has degraded to an acceptable level (usually about 10 half-lives of the radioactive isotope) depending upon the initial dose in the storage device. The system and process are configured such that dosing consistency can be assured in that each patient receives the desired amount of therapeutic or diagnostic agent.

As discussed in various embodiments or aspects of the present disclosure, improved systems and processes are provided for assuring that stored product is no longer designed to be or required to be patient specific. Instead, the systems disclosed herein are configured to dose a treatment for any patient that may be in the location on any particular day so that there is more flexibility in how the stored product can be utilized at the treatment location such that an effective dose of the radiopharmaceutical can be delivered to the patient. Such patient-specific dosing is accomplished without the need for dose calibrators, thereby eliminating additional dose assays for preparation of patient ready doses.

As discussed in various embodiments or aspects of the present disclosure, a system and process can be provided to monitor the therapeutic or diagnostic agent that is stored in the disposal container and indicate when the stored material has sufficiently decayed and is safe for throwing away. Once that determination is made, indication to the user can be provided (e.g. software prompts, or an LED light can turn from a red color to a green color or a red LED can be turned off and a green LED can be turned on) so staff can recognize that there is material that is suitable for disposal, locate the material to throw away, and suitably dispose of the material.

As discussed in various embodiments or aspects of the present disclosure, the improved inventory management flexibility associated with the systems and processes described herein permits care providers to more effectively manage inventory, which no longer has to be managed using a simplistic first in/first out approach and/or an approach that requires each stored dose to be provided for only a single, specific patient. Instead, inventory management and use of doses is managed to account for various factors including patient needs to better manage the supply of available doses. For instance, if a particular patient would require a large dose due to the patient's size (e.g. weight, height and weight, body composition, etc.), a newer, more radioactive vial of the therapeutic agent can be selected to administer to the patient so that only one vial (instead of multiple vials) is needed for the injection of a dose into the patient. This can permit the administration to occur more simply (e.g. only use of one injection sequence) and allow for more flexibility in terms of storage management and administration so doses are more efficiently utilized and less waste occurs. In some situations, this type of flexibility may also help reduce the exposure to a clinician during administering of the therapy and minimize the subsequent cleanup process after the patient has received his or her dose.

Figure 3:
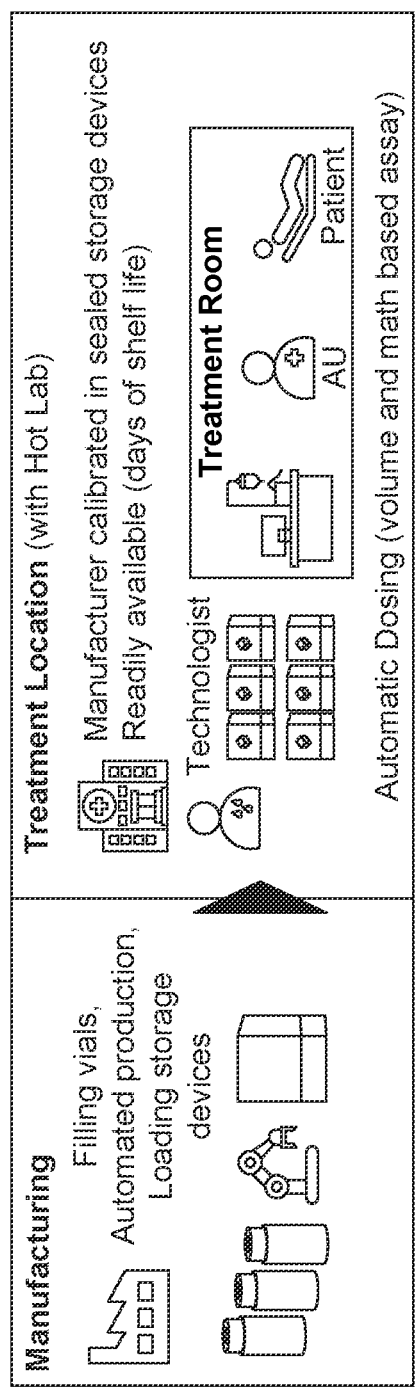
FIG. 3 is a representative schematic of an improved supply chain for a radioactive therapeutic agent configured for use with TRT according to some embodiments or aspects of the present disclosure.

FIG. 3 illustrates an improved supply chain for a therapeutic or diagnostic agent in accordance with some embodiments or aspects of the present disclosure. The therapeutic or diagnostic agent can be manufactured in bulk at a manufacturing facility. Instead of loading the therapeutic or diagnostic agent into bulk containers for shipping to a hot lab, the therapeutic or diagnostic agent is loaded into storage devices which are shipped directly to a treatment location. The storage device is configured to store the therapeutic or diagnostic agent from the point of production, during shipping, and during storage at the treatment facility. The therapeutic or diagnostic agent is configured to be administered directly from the storage device to a patient using a delivery system, as described herein. Dosing for each specific patient is determined by the delivery system instead of using a dose calibrator.

Figure 4:
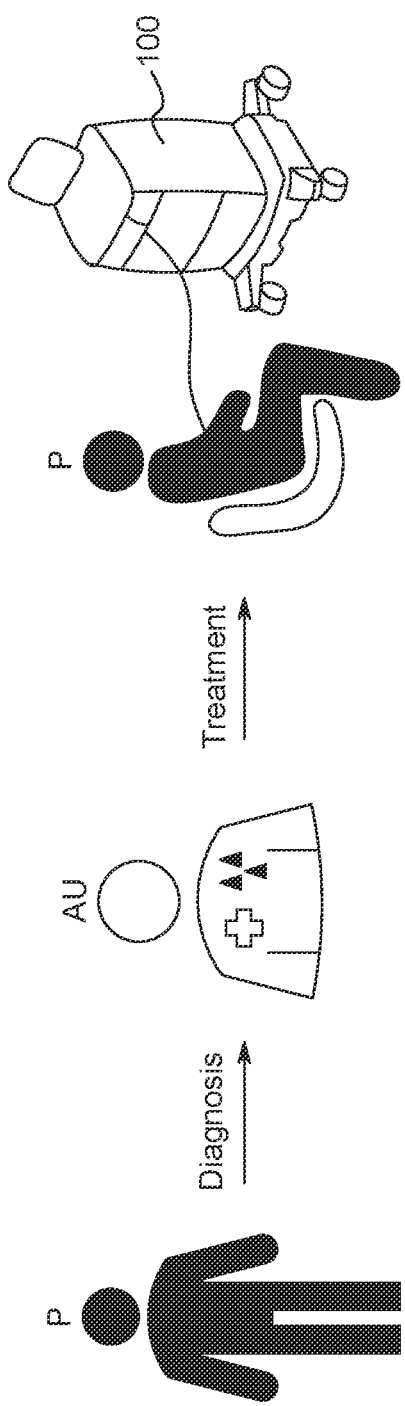
FIG. 4 is a representative schematic of an improved process for administration of TRT according to some embodiments or aspects of the present disclosure.

As shown in FIG. 4, the process for diagnosing, referring, and treating a patient in accordance with the improved supply chain eliminates multiple processes relative to a conventional process. After the patient P is diagnosed and prescribed a dose of the therapeutic or diagnostic agent based on the patient's weight, the dose can be administered using a delivery system 100 directly from a storage device 200 that is loaded into the delivery system 100. Prescribing and administration can be performed by the same authorized user AU.

Figure 5:
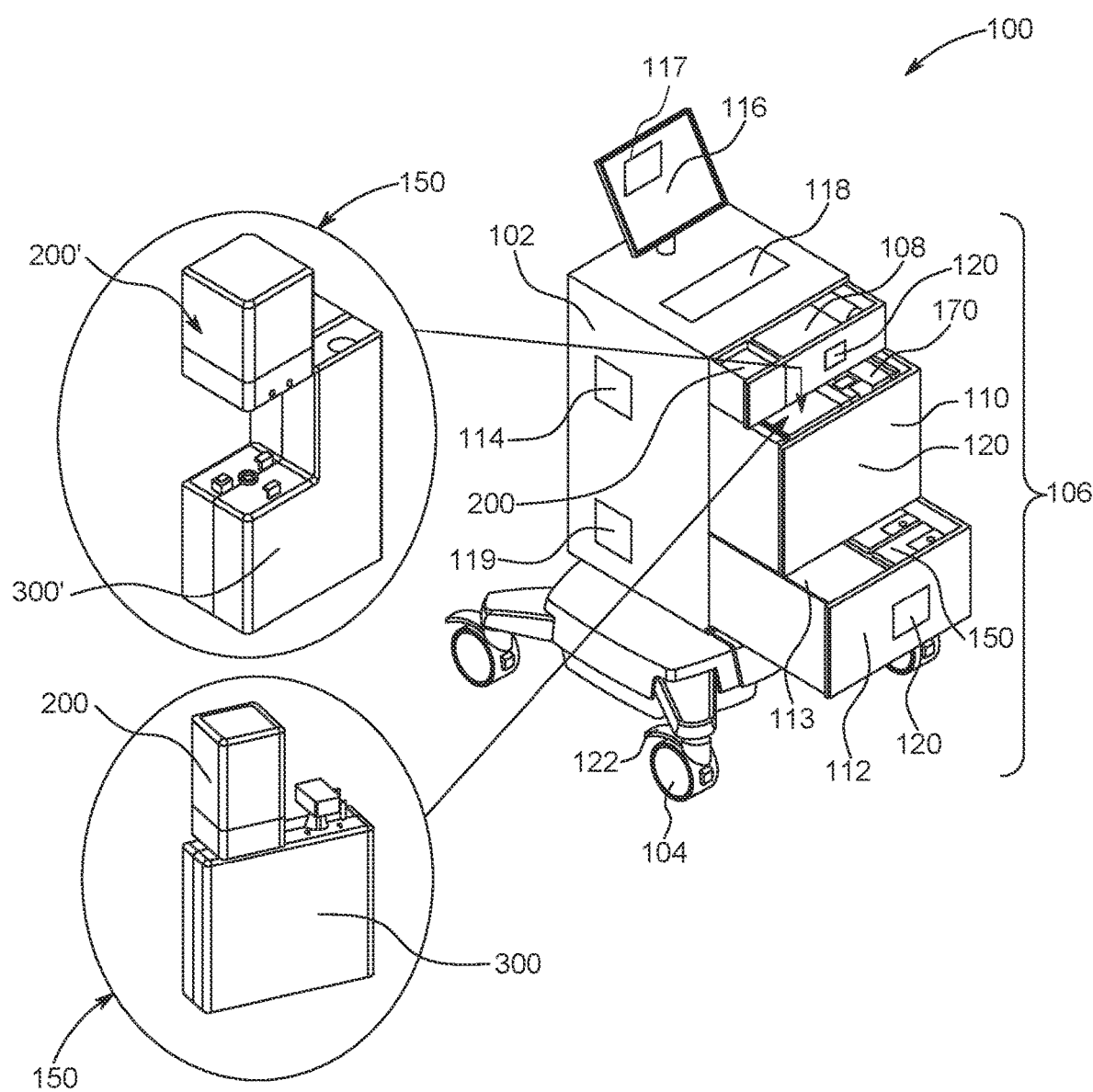
FIG. 5 is a perspective view of a system for distribution, administration, and disposal of a liquid product requiring precise volumetric delivery from a controlled source in accordance with some embodiments or aspects of the present disclosure.

With reference to FIG. 5, the delivery system 100 for distribution, administration, and disposal of a therapeutic or diagnostic agent is shown in accordance with some embodiments or aspects of the present disclosure. As described herein, the system 100 includes a number of components that are designed to work together to provide a safe, streamlined, and flexible distribution of the therapeutic or diagnostic agent. The delivery system 100 is further configured to help end users maintain and manage an inventory of the therapeutic or diagnostic agent.

In some embodiments or aspects, the delivery system 100 can be configured to store, administer, and dispose of the therapeutic or diagnostic agent, such as a radiopharmaceutical therapeutic or diagnostic agent. The radiopharmaceutical therapeutic or diagnostic agent that can be stored and injected into a patient can be a material that is in a fluid. The radiopharmaceutical can emit primarily alpha radiation or can emit primarily beta radiation. In some embodiments or aspects, the radiopharmaceutical can emit primarily auger radiation or positron radiation and thus secondary gamma radiation. For material that may emit primarily beta radiation, the storage device 200 and the delivery system 100 can be adapted to address secondary X-ray radiation that can be emitted as a result of the shielding of the beta radiation, as described herein. The delivery system 100 can be adapted to address gamma radiation emitted additionally emitted by the radiopharmaceutical. In some examples or aspects, the delivery system 100 can be configured for storage, administration, and disposal of XOFIGO® treatments as well as other TRT treatments that may utilize targeted alpha therapy or a targeted beta therapy. The delivery system 100 may also be configured to work for radioisotopes that may be made at a treatment location for a treatment or a diagnostic service (e.g. a radioisotope with a very short half-life such as technetium-99 or copper-64 that can be used for imaging or other purposes).

In some embodiments or aspects, the delivery system 100 can be configured to store, administer, and dispose of the therapeutic or diagnostic agent that is a radiopharmaceutical, such as an imaging radiopharmaceutical. The imaging radiopharmaceutical may be, in some embodiments or aspects, a Gamma emitting imaging radiopharmaceutical. Gamma emitting imaging radiopharmaceuticals include, without limitation, 99mTc, 123I, 111In, 67Ga, and/or 186Re. In some embodiments or aspects, the imaging radiopharmaceutical may be a Positron emitting imaging radiopharmaceutical. Positron emitting imaging radiopharmaceuticals include, without limitation, 13N, 18F, 68Ga, 89Zr, 124I, 64Cu, 82Rb, and/or 86Y.

In some embodiments or aspects, the delivery system 100 can be configured to store, administer, and dispose of the therapeutic or diagnostic agent that is a radiopharmaceutical, such as a therapeutic radiopharmaceutical. The therapeutic radiopharmaceutical may be, in some embodiments or aspects, a Beta therapeutic radiopharmaceutical. Beta therapeutic radiopharmaceuticals include, without limitation, Lutetium-177, Iodine-131, Yttrium-90, Copper-67, Rhenium-188 and/or Holmium-166. The therapeutic radiopharmaceutical may be, in some embodiments or aspects, an Alpha therapeutic radiopharmaceutical. Alpha therapeutic radiopharmaceuticals include, without limitation, Radium-223, Actinium-225, Thorium-227, Astatine-211, Lead-212 and/or Bismuth-213. The therapeutic radiopharmaceutical may be, in some embodiments or aspects, an Auger therapeutic radiopharmaceutical. Auger therapeutic radiopharmaceuticals include, without limitation, Terbium-161 and/or Iodine-125. In some embodiments or aspects, the radiopharmaceutical is selected from the group consisting of 177Lu-Oxodotreotide, 223Ra dichloride, 18F-Fluciclovine, 123I-Ioflupane, 68Ga-Dotatate, 111In, 99mTc-Tilmanocept, 99mTc-tetrofosmin, 18F-Florbetaben, 99mTc, 90Y-Ibritumomab tiuxetan, 18F-Florbetapir, 153Sm-Lexidronam EDTMP, 131I-Iobenguane MIBG, and/or 89Sr-Chloride. In some embodiments or aspects, the radionuclide of the radiopharmaceutical configured for imaging or therapy use is linked to FAP (fibroblast activation protein), PSMA (prostate specific membrane antigen), DOTA (dodecane tetraacetic acid and its chelating derivatives), HER2 (human epidermal growth factor receptor 2), GPC-3 (glypican-3 protein) or other mechanisms of action with radiopharmaceuticals.

In some embodiments or aspects, the delivery system 100 can be configured to work for radioisotopes that may be made at a treatment location for a treatment or a diagnostic service (e.g., a radioisotope with a very short half-life such as technetium-99m, nitrogen-13, flourine-18, gallium-68 or copper-64) that can be used for imaging or other purposes. These types of radioisotopes tend to have a very short half-life, which requires an imaging provider to prepare the radioisotopes in a hot lab or central radiopharmacy on site for effective use for a diagnostic service. For such an application, the provider may prepare the diagnostic service material on-site. The provider can then insert that material within a vial, place the vial in a storage device, and record and label that storage device to indicate its date of creation fluid volume, concentration, and/or initial radioactivity. The storage device may have a unique device identifier that is used to record the contents information in the software system. That storage device can then be coupled to a cassette, injector, and infusion set as described herein to provide a determined dose to a patient prior to the patient undergoing imaging. The used materials can also be stored etc. in a similar fashion for disposal, as described herein.

Following is a detailed description of various components of the delivery system 100 and how such components permit utilization of the delivery system 100 for an improved distribution, administration, and disposal of therapeutic or diagnostic agents.

With continued reference to FIG. 5, the delivery system 100 is shown in accordance with one embodiment or aspect of the present disclosure. The delivery system 100 may be configured as a mobile device. The delivery system 100 includes a cart 102 supported on wheels 104 for moving the cart 102. In some embodiments or aspects, the delivery system 100 can be fixedly mounted. The cart 102 includes a plurality of storage components 106, such as shelves or drawers for storing various components of the delivery system 100. In some embodiments or aspects, the storage components 106 include a first drawer or shelf 108 for storing one or more storage devices 200 prior to use. The first drawer 108 may include the ability to keep a storage container 200 cold to meet the requirements of the drug being stored. The first drawer or shelf 108 may be further configured to store infusion sets and other fluid path components for connecting the delivery system 100 to a patient during administration of the therapeutic or diagnostic agent. The storage components 106 may include a second drawer or shelf 110 configured for receiving components of the delivery system 100 for administration of the therapeutic or diagnostic agent. For example, the second drawer or shelf 110 can be configured to receive one or more assemblies 150 for administering a dose of the therapeutic or diagnostic agent. As described herein, each assembly 150 includes a single storage device 200 connected to a single use fluid cassette 300. In some embodiments or aspects, the assembly 150 can include one or more multi-use storage devices 200 and multi-use fluid cassettes 300. Each assembly 150 is removably insertable into the second drawer or shelf 110. The assembly 150 is operatively connectable to an injector 170 for delivering a dose of the therapeutic or diagnostic agent. The assembly 150 may be configured for a single use with a single patient. In some embodiments or aspects, the assembly 150 may be configured for use with multiple patients.

The delivery system 100 further includes a third drawer or shelf 112 configured for storing one or more used assemblies 150. Each assembly is configured to minimize the handling of the storage device 200 during workflow. At least one of the first, second, and third drawers or shelves 108, 110, 112 can have radiation shielding material to sufficiently reduce emission or radioactivity outside the cart 102.

With further reference to FIG. 5, the delivery system 100 further includes a controller 114 for controlling a delivery of a dose of the therapeutic or diagnostic agent. The controller 114 can be connected to one or more user displays 116 for displaying information relating to the storage, administration, and/or disposal aspects of the therapeutic or diagnostic agent. In some embodiments or aspects, the display 116 is a touch screen display enabling control via touch commands received from a user. The controller 114 can further be connected to an input device 118 for inputting data relating to storage, administration, and/or disposal of the therapeutic or diagnostic agent. In some embodiments or aspects, the input device 118 can be a bar code scanner, a keyboard, a mouse, a touch screen display, and/or any other input mechanism for inputting data and/or commands to the controller 114 relating to operation of the delivery system 100. The input device 118 may include the capability for video conferencing. The controller 114 can further be connected to a camera 117. The camera may be used to give input to the controller, such as reading a machine readable or human readable label or tag. The camera may be used to take images of, record, and/or communicate anything that is going on for use by the onsite operator, an offsite operator, or for training or archiving purposes. In some embodiments or aspects, an output device 119, such as a printer, is provided. The printer 119 may be used to print a label for documentation, a label to put on trash, a travel card for a patient, a reminder for patient, and/or guidelines for a patient.

The controller 114 may include at least one processor programmed or configured to calculate a dose of a therapeutic or diagnostic agent to be delivered to a specific patient based on patient data and/or data relating to one or more characteristics of the therapeutic or diagnostic agent. The at least one processor of the controller 118 further may be configured to actuate various components of the delivery system 100 to effect a delivery of a dose to a patient according to a programmed protocol for an injection procedure. The controller 118 may include computer readable media, such as memory, on which one or more injection protocols may be stored for execution by the at least one processor.

Figure 16:
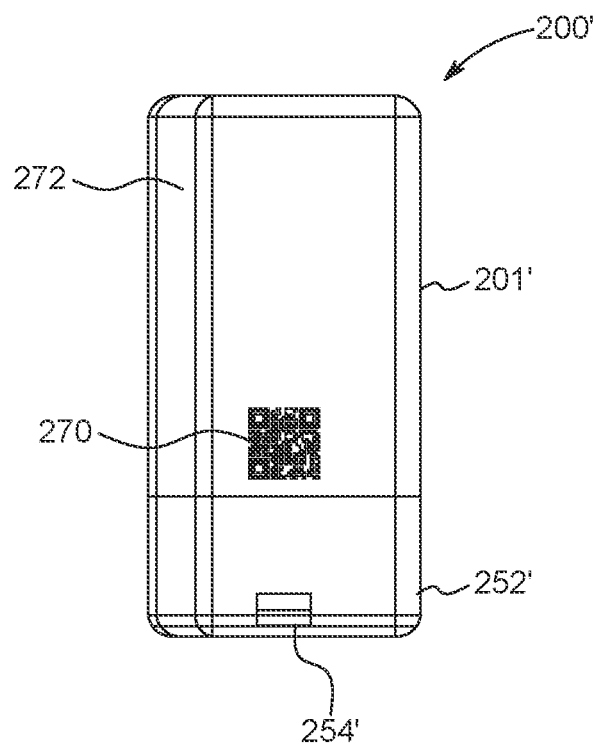
FIG. 16 is a side view of the storage device shown in FIG. 15.

The controller 114 of the delivery system 100 can be adapted to determine a dose of the therapeutic or diagnostic agent to provide to a patient. The dose can be determined from one or more variables that can be provided to the controller 114 via the one or more input devices 118. For example, patient weight or other patient characteristics can be entered via a keyboard and/or mouse. Ranges of radiopharmaceutical activities of the therapeutic or diagnostic agent can be determined by the controller 114 based on information associated with the label or tag 270, such as a machine readable label (e.g. barcode) or electronic tag (e.g. RFID) attached to the storage device 200 shown in FIG. 16. In some embodiments or aspects, the information associated with the label or tag 270 can include manufacturing information and/or radioactivity information (e.g., date of manufacture, date and time of calibration, activity at calibration, level of radioactivity of the material at the time of manufacture, volume of fluid, concentration of fluid, type of radioisotope, etc.). In further embodiments or aspects, information associated with the label or tag 270 can include time and temperature history values of the storage device 200 during shipping and handling. This information as well as the current date or time can be used by the controller 114 to determine an appropriate dose for a patient by use of a pre-defined dosing algorithm that can utilize such parameters. Some pre-defined dosing algorithm can also use additional parameters, such as weight of the patient, sex of the patient, and/or age of the patient. Some pre-defined dosing algorithms can also use additional parameters such as prescribed dose and prescribed or targeted tissue dose.

In some embodiments or aspects, the controller 118 can have different dosing algorithms for different pre-defined treatments. The scanned barcode, read RFID tag, and/or other input provided by a user can be utilized to select the appropriate dosing algorithm to be run for determining the dose for the patient.

With continued reference to FIG. 5, each of the storage compartments 106 is lockable and is configured to be accessed by an authorized user having the appropriate access protocol. For example, each of the storage compartments 106 may have a lock 120 that is operatively connected to the controller 114. Operation of the lock 120 may require inputting a password or other authentication means using, for example, the display 116 or the input device 118 to authenticate an authorized user of the delivery system 100.

With continued reference to FIG. 5, one or more of the wheels 104 of the cart 102 may have a wheel lock 122 for selectively locking the wheels 104 to prevent movement of the cart 102. The wheel lock 122 may be configured to prevent unauthorized movement of the cart 102. For example, the wheel lock 122 may be operatively connected to the controller 114. Operation of the wheel lock 122 may require inputting a password or other authentication means using, for example, the display 116 or the input device 118 to authenticate an authorized user of the delivery system 100 to permit movement of the wheels 104. The wheel lock 122 may be a mechanical lock having a key or other mechanical lock mechanism. In some embodiments or aspects, the wheel lock 122 may be operatively connected with the lock 120 of the storage compartments 106 such that operation of one of the wheel lock 122 and the lock 120 also controls the operation of the other of the wheel lock 122 and the lock 120. In some embodiments or aspects, an alarm system may be operatively connected to at least one of the lock 120 and the wheel lock 122 such that an alarm may sound or an alarm message is provided for an unauthorized use of the delivery system 100. In some embodiments or aspects, the alarm system may be configured to prevent operation of the delivery system 100 and/or movement of the cart 102, such as by locking the wheel lock 122. Cart 102 may also include a compartment for storing ancillary equipment 113 which, while not used directly in the infusion process, is necessary or useful in the overall procedure. For example it may contain a survey meter or other radiation detector to survey the outside of the packaging and/or storage containers 200 when checking them in to the cart. The survey meter may also be used to survey the outside of assemblies 150 after an injector to check for leakage. The survey meter may also be used to survey the patient, the operator, and the injection room for any contamination, The auxiliary equipment compartment 113 may also contain a spill remediation kit for unusual instances where a spill occurs, for example if the IV comes out of the patient's arm during an infusion. The auxiliary equipment compartment may include other items commonly found in a hot lab and needed for this infusion because a benefit of this delivery system 100 is to provide the necessary capabilities and equipment to safely deliver the drugs it is designed to deliver.

Figure 6:
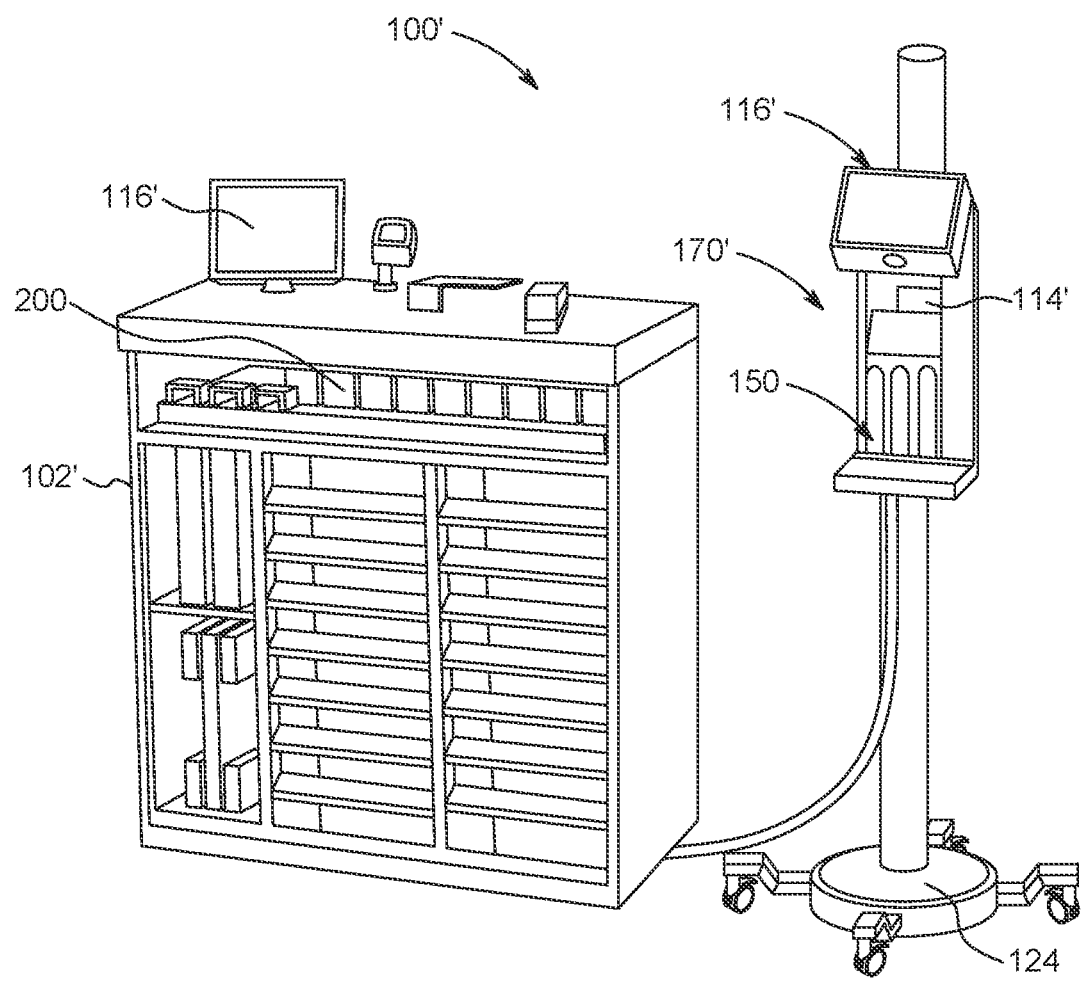
FIG. 6 is a perspective view of a system for distribution, administration, and disposal of a liquid product requiring precise volumetric delivery from a controlled source in accordance with some embodiments or aspects of the present disclosure.

With reference to FIG. 6, a delivery system 100' is shown in accordance with another embodiment or aspect of the present disclosure. Similar to the delivery system 100 shown and described with reference to FIG. 5, the delivery system 100' shown in FIG. 6 is configured as a mobile device that includes a cart 102' supported on optional wheels. The cart 102' includes a plurality of storage components 106' for storing one or more storage devices 200 prior to use and for storing one or more used assemblies 150.

Instead of incorporating the injector 170 into the cart 102, the delivery system 100' shown in FIG. 6 has a separate injector 170' supported on a separate movable base 124. The injector 170' is configured to receive the assembly 150 including the storage device 200 and the fluid cassette 300. The delivery system 100' further includes a controller 114' for controlling a delivery of a dose of the therapeutic or diagnostic agent. The controller 114' can be connected to one or more user displays 116' for displaying information relating to the storage, administration, and/or disposal aspects of the therapeutic or diagnostic agent. In some embodiments or aspects, the display 116' is a touch screen display enabling control via touch commands received from a user. The user display 116' may be configured for inputting data relating to storage, administration, and/or disposal of the therapeutic or diagnostic agent. In some aspects some of the communications may be wireless so that no continuous physical connection is required between the selected parts. In some aspects of the system 100 there may be one or more fixed carts 102' and one or more mobile carts 102 in communication with each other to facilitate flexible or optimal storage and use of the materials involved. In busy sites, used assemblies 150 may be transferred from movable carts to fixed carts which may provide auxiliary decay in place storage. This may be done, for example at the end of the day, either by moving individual units or through a transfer of a whole drawer from one cabinet to another. The auxiliary decay in place cabinet may be in a different room or even a different facility.

Figure 7:
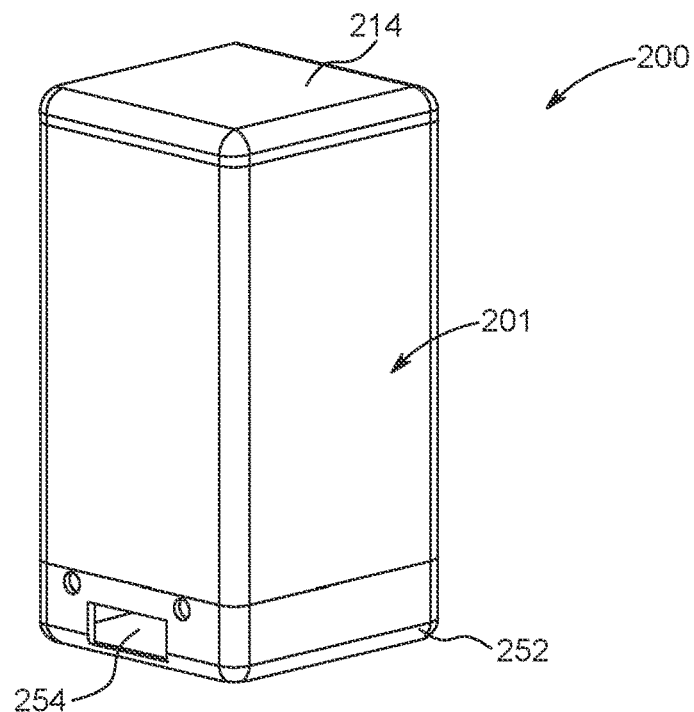
FIG. 7 is a perspective view of a storage device for storing a liquid product, such as a radioactive therapeutic agent, in accordance with some embodiments or aspects of the present disclosure.
Figure 8:
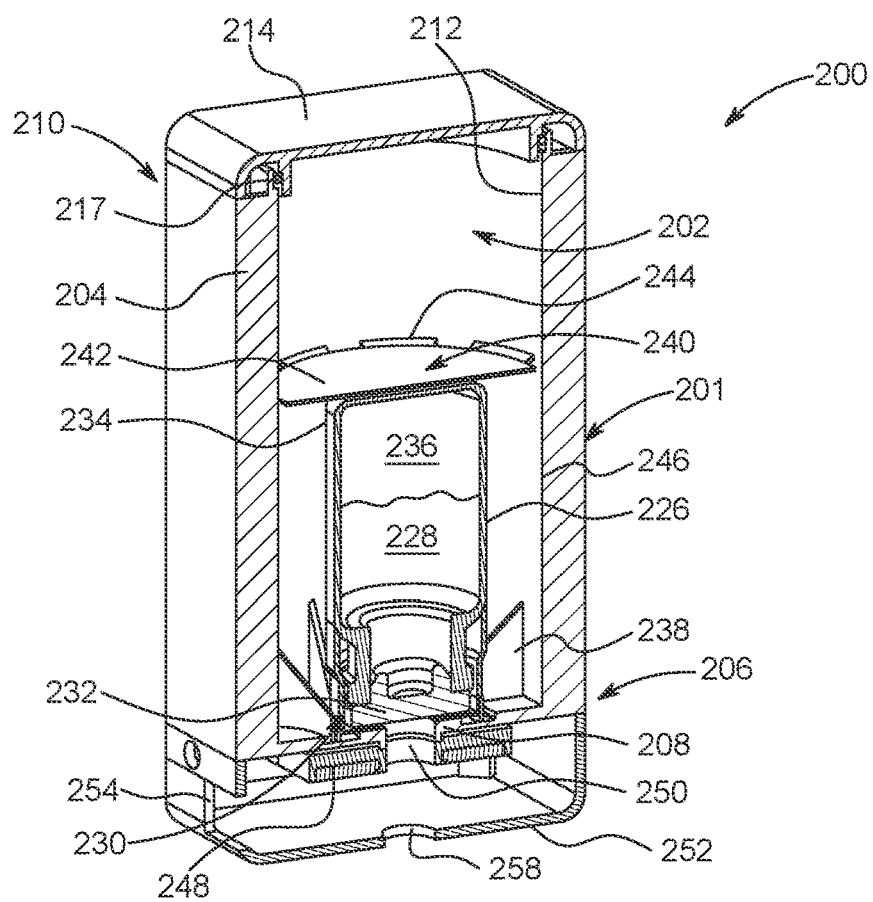
FIG. 8 is a cross-sectional perspective view of the storage device shown in FIG. 7.
Figure 9:
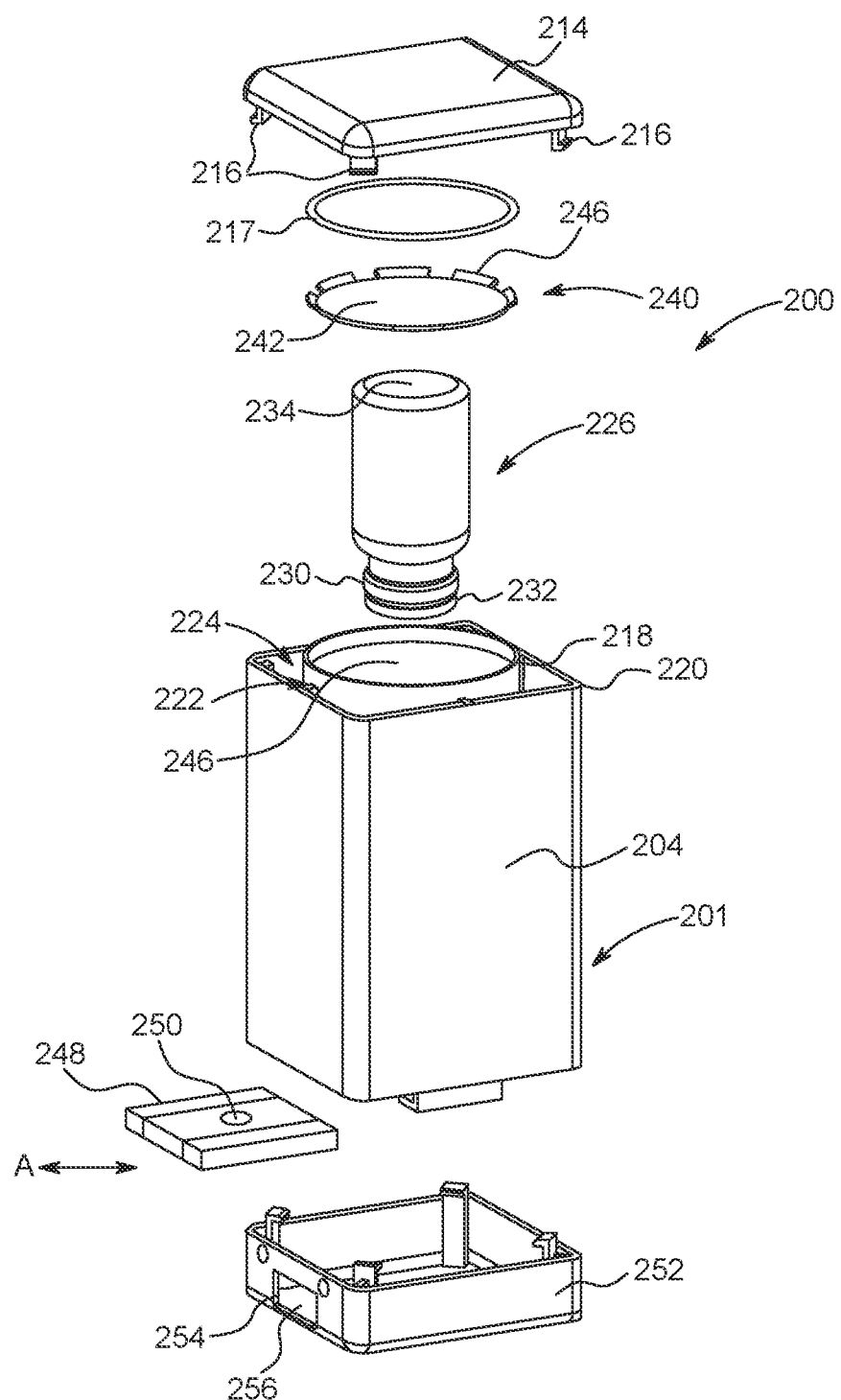
FIG. 9 is an exploded top perspective view of the storage device shown in FIG. 7.

With reference to FIGS. 7-9, the storage device 200 is shown in accordance with one embodiment or aspect of the present disclosure. As discussed herein, the storage device 200 is configured to store a quantity of a therapeutic or diagnostic agent. In embodiments or aspects where the therapeutic or diagnostic agent is a radiopharmaceutical, the storage device 200 is configured to contain the radiation emitted by the radioisotope of the radiopharmaceutical.

With reference to FIG. 8, the storage device 200 includes a housing 201 having a chamber 202 defined therein. The housing 201 has a main body 204 defining the chamber 202. The main body 204 has a proximal end 206 with a first opening 208 and a distal end 210 with a second opening 212. A cap 214 is provided to enclose the second opening 212 at the distal end 210 of the main body 204 of the housing 201. In some embodiments or aspects, a gasket or seal 217 is provided at an interface between the cap 214 and the distal end 210 of the main body 204. In some embodiments or aspects, the cap 214 is non-removably connected to the main body 204 via, for example, one or more clips 216 (shown in FIG. 9). In some embodiments or aspects, the cap 214 may be removably connectable to the main body 204. In some embodiments or aspects, the main body 204 and the cap 214 of the housing 201 may be made from, incorporate, or house a shielding material, such as poly(methyl methacrylate) (PMMA), lead, or tungsten.

With reference to FIG. 9, the main body 204 has an inner portion 218 defining the chamber 202 and an outer portion 220. The inner portion 218 may be connected to the outer portion 220 by one or more connectors 222. In some embodiments or aspects, a cavity 224 is defined between the inner portion 218 and the outer portion 220. The cavity 224 may be an air cavity, or it may be filled with one or more of a shielding material, such as PMMA, lead, or tungsten, a shock absorbing material such as polystyrene beads, or an absorbent material such as paper. The filling material may be formed for example from one or more of a solid sheet, in loose form, such as in the form of beads or pellets, a liquid, or a pourable filling that hardens, or a combination thereof. The inner portion 218 and the outer portion 220 may have the same shape or a different shape. For example, the inner portion 218 may have a substantially cylindrical shape while the outer portion 220 may have a substantially cuboid shape. The edges of the cuboid-shaped outer portion 220 may be rounded. In some embodiments or aspects, the inner portion 218 and the outer portion 220 may be monolithically formed.

For agents that emit beta radiation, the internal structure of the storage device 200 can be designed and configured to prevent X-rays formed from beta radiation from being emitted out of the housing 201. This blocking of beta radiation and X-rays can be affected by an inner structure of the storage device 200, such as a shielding material disposed in the cavity 224. Alternatively, or in addition, the sidewall of the housing 201 can be chosen, such as by selecting the thickness and material properties, to prevent emissions of X-rays and beta radiation. In some embodiments or aspects, the storage device 200 can have a plurality of spaced shields (e.g. spaced apart shield walls) defined between the chamber 202 and the outer walls of the housing 201. In some configurations, packing or a fluid (e.g. air) can be positioned in the cavity 224 to provide sufficient shielding of X-rays and/or beta radiation.

Alpha radiation is typically not as difficult to block as alpha particles are large, have more limited penetrating power, and generally administered in lower doses than betas. The sidewalls of the housing 201 can be selected to be of a sufficient thickness for shielding the alpha radiation. Additional wall thickness or packing can be provided within the cavity 224 to help secure the vessel 226 in a desired location and/or provide additional shielding as many alpha and beta emitting isotopes or their daughter isotopes also give off gamma radiation to prevent any additional radiation exposure from the radiopharmaceutical being emitted out of the housing. The size of the housing 201 relative to the vessel 226 may be selected so as to set a minimum distance from the exterior of the housing 201 to the vessel 226 in order to reduce user exposure. In general, though, isotopes emit more than one type of radiation or radiation of different energy levels with different penetrating powers. In addition, all isotopes with have some buildup of daughter products between manufacture of the drug and delivery. Thus there may need to be significant gamma shielding for what are nominally alpha or beta emitters. The materials used for shielding and the guidelines involved are well known to those in the health physics field.

With reference to FIGS. 8-9, the chamber 202 of the housing 201 is configured to hold a vessel 226 containing a therapeutic or diagnostic agent 228 therein (shown in FIG. 8). The vessel 226 can be a glass vial that is formed separately from the housing 201 of the storage device 200 and is inserted into the chamber 202 of the housing 201. In some embodiments or aspects, the vessel 226 may be integrally formed with the storage device 200. Size of the chamber 202 is selected to accommodate the largest vessel 226 that may be used with the storage device 200 and/or to account for any additional packing or shielding material that may be required.

The vessel 226 has a proximal end 230 having an access port 232 and a closed distal end 234 with an interior 236 defined between the proximal end 230 and the distal end 234. The access port 232 may be a pierceable septum configured to be pierced by a vessel access member or other access mechanism for accessing the therapeutic or diagnostic agent 228 within the interior 236 of the vessel 226, as discussed herein. During manufacture of the therapeutic or diagnostic agent 228, the agent 228 can be filled into the vessel 226 and the vessel 226 can subsequently be sealed via the access port 232 to retain the agent 228 therein. Filling of the vessel 226 can occur after the vessel 226 is connected or positioned within a chamber 201 of the storage device 200, or prior to connecting or positioning the vessel 226 within the chamber 201. In some embodiments or aspects, the access port 232 may be fully sterilized at the point of manufacture. Vessel 226 may also be a plastic vial, a flexible bladder, a collapsible bag, or a prefilled syringe, preferably with a plunger but no handle to reduce the space needed. A benefit of collapsible vessels and prefilled syringes is that as fluid is pulled, the vessel collapses or plunger moves down so that no air needs to be admitted into the vessel as fluid is removed.

With reference to FIG. 8, the proximal end 230 of the vessel 226 is positioned at the proximal end 206 of the housing 201 such that the access port 232 is positioned opposite the first opening 208. In this manner, the vessel access member can extend through the first opening 208 of the housing 201 and through the access port 232 of the vessel 226 during administration of the therapeutic or diagnostic agent 228.

In some embodiments or aspects, the vessel 226 may be secured at the proximal end 206 of the housing 201 by a plurality of ribs 238 within the chamber 202 of the housing 201 and surrounding the first opening 208. Each of the plurality of ribs 238 may be configured to engage the proximal end 230 of the vessel 226 to fix the position of the access port 232 relative to the first opening 208 of the housing 201.

Figure 10:
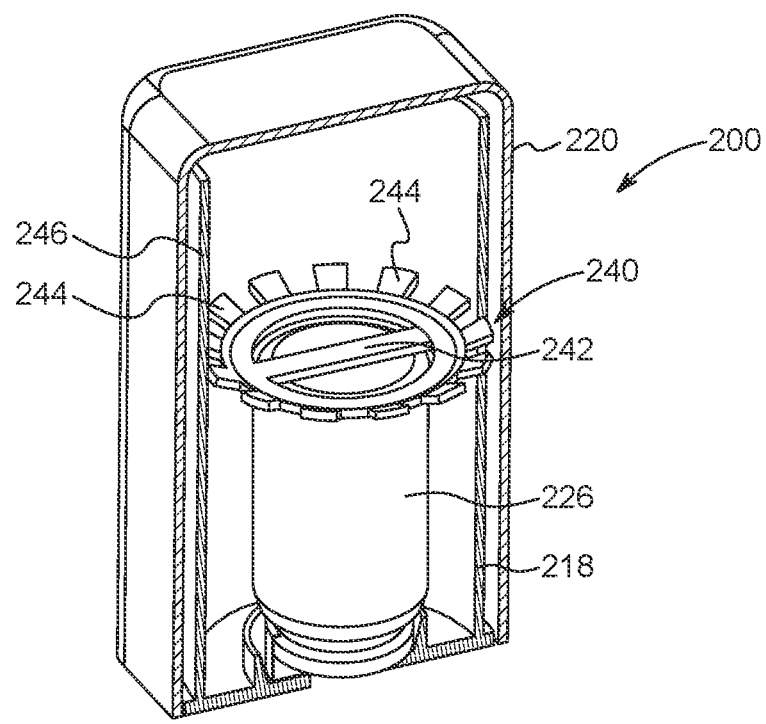
FIG. 10 is a cross-sectional perspective view of a storage device shown with a first vessel.
Figure 11:
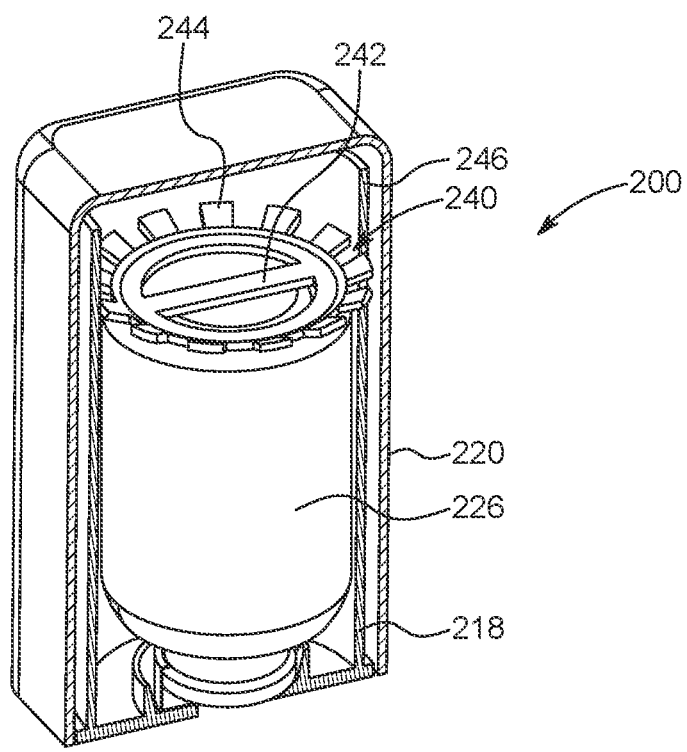
FIG. 11 is a cross-sectional perspective view of a storage device shown with a second vessel.

With reference to FIGS. 8-9, the storage device 200 has a holder 240 within the chamber 202 of the housing 201. The holder 240 may be configured to retain the distal end 234 of the vessel 226 relative to the housing 201. The holder 240 may be in contact with the distal end 234 of the vessel 226 so as to fix the position of the vessel 226 relative to the housing 201. In some embodiments or aspects, the holder 240 includes a contact element 242 for contacting the distal end 234 of the vessel 226 and a plurality of tabs 244 connected to the contact element 242 and configured to engage housing 201, such as an inner surface 246 of the inner portion 218 of the housing 201 to fix the position of the vessel 226 relative to the housing 201. As shown in FIGS. 9-10, the plurality of tabs 244 may be angled relative to the contact element 242 such that they are oriented at a non-perpendicular angle relative to the inner surface 246 of the inner portion 218 of the housing 201. The plurality of tabs 244 may flex relative to the contact element 242 such that, when the contact element 242 is pushed against the distal end 234 of the vessel 226, the plurality of tabs 244 provide a restoring force against movement of the holder 240 in a distal direction away from the distal end 234 of the vessel 226. In this manner, the holder 240 is configured to retain a plurality of different vessels 226, regardless of their diameter and longitudinal length.

With reference to FIGS. 8-9, the storage device 200 has a door 248 associated with the housing 201. In some embodiments or aspects, the door 248 may be movable relative to the housing 201 between a closed position and an open position shown in FIG. 8. The door 248 may be moveable between the closed position and the open position in response to actuation by an access mechanism of the delivery system 100, as described herein. In some embodiments or aspects, the door 248 may be normally closed. In the closed position, the door 248 is configured to cover the first opening 208 in the housing 201 to enclose the chamber 202 of the housing 201. In this manner, the vessel 226 is completely enclosed within the chamber 202 and access to the access port 232 is prevented. In the open position, the door 248 is moved relative to the housing 201 to reveal the first opening 208 in the housing 201 for accessing the access port 232 of the vessel 226. In some embodiments or aspects, the door 248 may be slidably movable relative to the housing in a direction of arrow A shown in FIG. 9.

With continued reference to FIGS. 8-9, the door 248 has an access aperture 250 configured to line up with the first opening 208 of the housing 201 when the door 248 is in the open position. In this manner, the vessel access member can extend through the access aperture 250 and the first opening 208 and into the access port 232 of the vessel 226.

With continued reference to FIGS. 8-9, a door cover 252 is connected to the housing 201 and is configured to enclose the door 248 within a door chamber. The door cover 252 is non-removably connected to the main body 204 via, for example, one or more clips 216 (shown in FIG. 9). In some embodiments or aspects, the door cover 252 may be removably connectable to the main body 204 of the housing 201. In some embodiments or aspects, the door cover 252 may be made from the same material as the main body 204 and the cap 214 of the housing 201.

With reference to FIG. 9, the door cover 252 has a door access opening 254 having a seal 256 and a vessel access opening 258 (shown in FIG. 8) positioned opposite the first opening 208 of the housing 201. The vessel access opening 258 is configured to receive a spike or other vessel access member of the delivery system during administration of the therapeutic or diagnostic agent 228. The vessel access opening 258 is aligned with the access aperture 250 on the door 248 when the door 248 is in the open position to permit the spike or other vessel access member to extend through the first opening 208 on the housing 201 for access to the access port 234.

Figure 12:
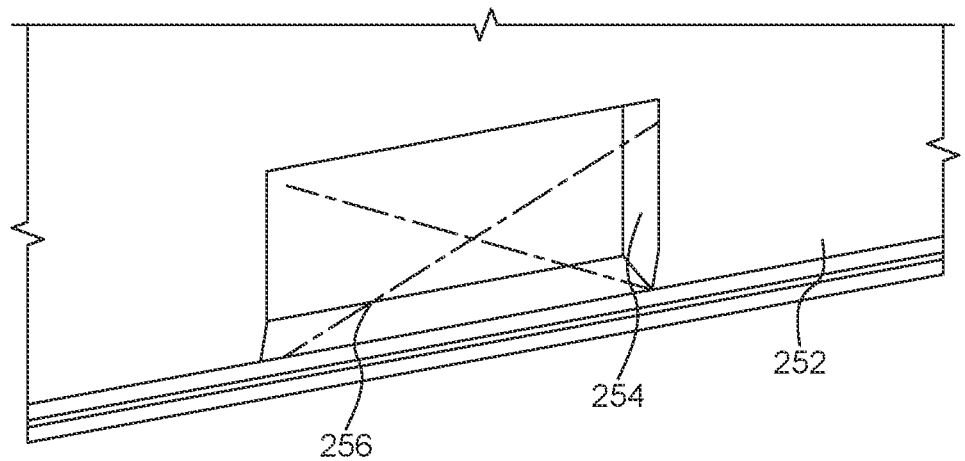
FIG. 12 is a detailed perspective view of a security cover on an access door of a storage device in accordance with some embodiments or aspects of the present disclosure.

With reference to FIG. 12, the seal 256 covers the door access opening 254 and is pierceable by an access mechanism of the delivery system 100, as described herein. In some embodiments or aspects, the access mechanism of the delivery system 100 may be configured to sense the presence of the seal 256, such as by sensing a resistance to movement through the door access opening 254 when the seal 256 is present. If the access mechanism of the delivery system 100 does not detect the seal 256, such as due to no resistance to movement through the door access opening 254, the controller 114 may be configured to prevent operation of the delivery system 100 because a used storage device 200 (i.e., one with a pierced seal 256), or a tampered storage device 200 (i.e., one with a removed seal 256) has been installed for use with the delivery system 100. In this manner, the seal 256 functions as a security mechanism to assure that only an untampered storage device 200 can be used with the delivery system 100. In some embodiments or aspects, the seal 256 may also be provided over the vessel access opening 258. In some embodiments, the seal may be a member of the housing 201 which is broken off or permanently deformed as evidence of use or tampering.

Figure 13:
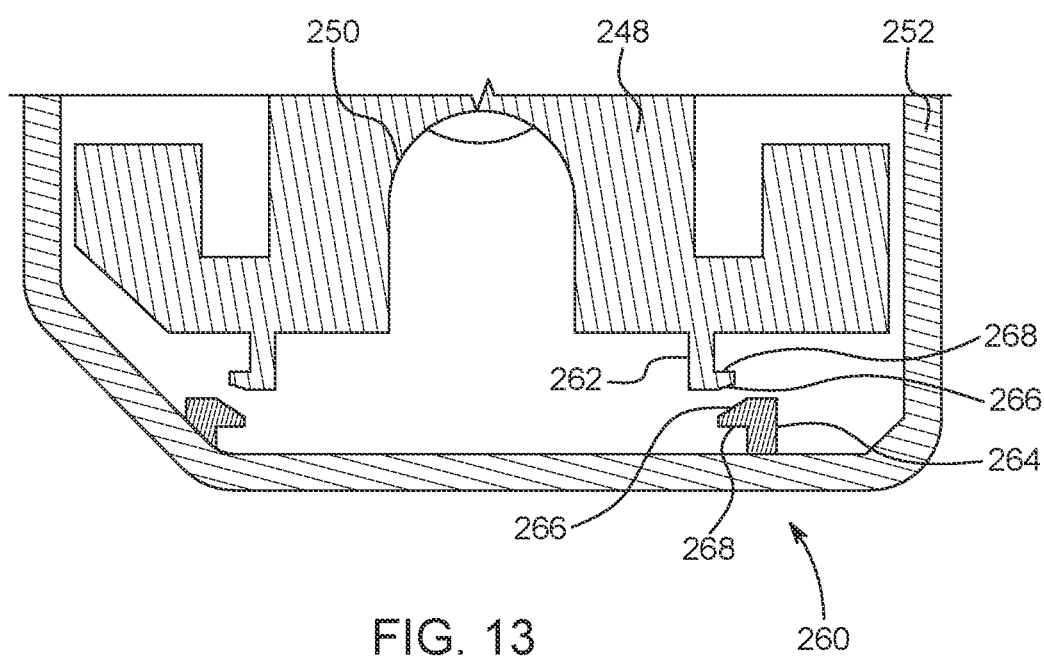
FIGS. 13-14 are detailed views of a locking mechanism for preventing reuse of a storage device in accordance with some embodiments or aspects of the present disclosure.
Figure 14:
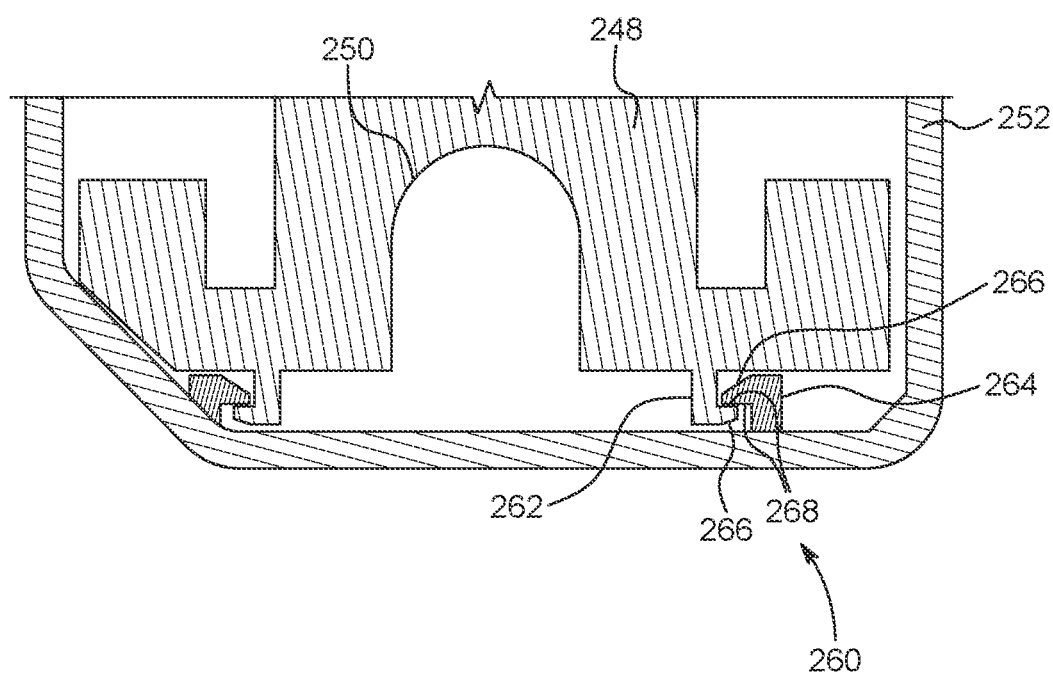
Figure 15:
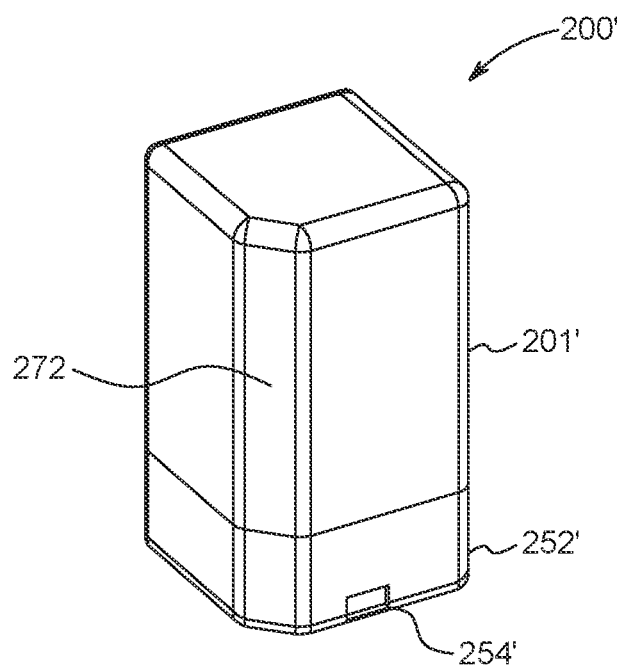
FIG. 15 is a perspective view of a storage device for storing a liquid product, such as a radioactive therapeutic agent, in accordance with some embodiments or aspects of the present disclosure.

With reference to FIGS. 13-14, a door lock 260 is shown in accordance with some embodiments or aspects. The door lock 260 may be provided on the door 248 for locking the door 248 in the open position after the door 248 is moved from the closed position to the open position. In some embodiments or aspects, the door lock 260 includes at least one first hook 262 that is configured to engage with at least one second hook 264 on the housing 201 or the door cover 252 (shown in FIGS. 8-9). Each of the at least one first hook 262 and the at least one second hook 264 may have an angled contact surface 266 and a catch 268 that is configured to engage once the two contact surfaces 266 slide past each other. FIG. 14 shows the at least one first hook 262 and the at least one second hook 264 in a locked engagement with each other when the door 248 is in the open position. Due to this locked engagement, the door 248 cannot be moved back to the closed position.

In some embodiments or aspects, the door 248 may be movable between three different positions. In an initial position, the door 248 may be closed. In an intermediate position, the door 248 may be moved from the initial (closed) position to an open position to permit access to the vessel 226. In a final position, the door 248 may be moved to a closed position, in which the door 248 is engaged with the door lock 260 to prevent the door 248 from being reopened and any remaining contents in the vessel 226 from being accessed.

With reference to FIGS. 15-19, a storage device 200' is shown in accordance with another embodiment or aspect of the present disclosure. As the structure of the storage device 200' shown in FIGS. 15-19 is substantially similar to the structure of the storage device 200 shown and described with reference to FIGS. 7-14, a detailed description of the components of the storage device 200' will be omitted. The same reference numbers will be used in FIGS. 15-19 to describe the components of the storage device 200' as used in FIGS. 7-14 to describe the components of the storage device 200, except for the addition of a " ' " mark after each reference number in FIGS. 15-19. The following detailed disclosure will focus only on relative differences between the two storage devices.

In some embodiments or aspects, the storage device 200 may have at least one label, tag, or other indicia 270 on the housing 201. While the at least one label, tag, or other indicia 270 is shown in connection with the embodiment of the storage device shown in FIG. 16, the at least one label, tag, or other indicia 270 may be applied to any storage device 200 described herein, such as the storage device 200 described herein with reference to FIGS. 7-14. The at least one label, tag, or other indicia 270 may contain machine readable authenticatable data configured to be read by the delivery system 100 to authenticate the storage device 200 prior to use. In some embodiments or aspects, the machine readable authenticatable data includes at least one of product information, production information, prescription information, and shipping conditions information. The at least one label, tag, or other indicia 270 can be a label (e.g. barcode, a QR code, or similar) and/or a tag (e.g. electronic, RFID, or similar) that includes at least one of product information, production information, prescription information, and shipping conditions information relating to the therapeutic or diagnostic agent. In some embodiments or aspects, the at least one label, tag, or other indicia 270 can include a data logger configured for logging, for example, temperature, shock, and/or pressure data. In some embodiments or aspects, the at least one label, tag, or other indicia 270 can include a link to accessing information from a website or a database.

Figure 28:
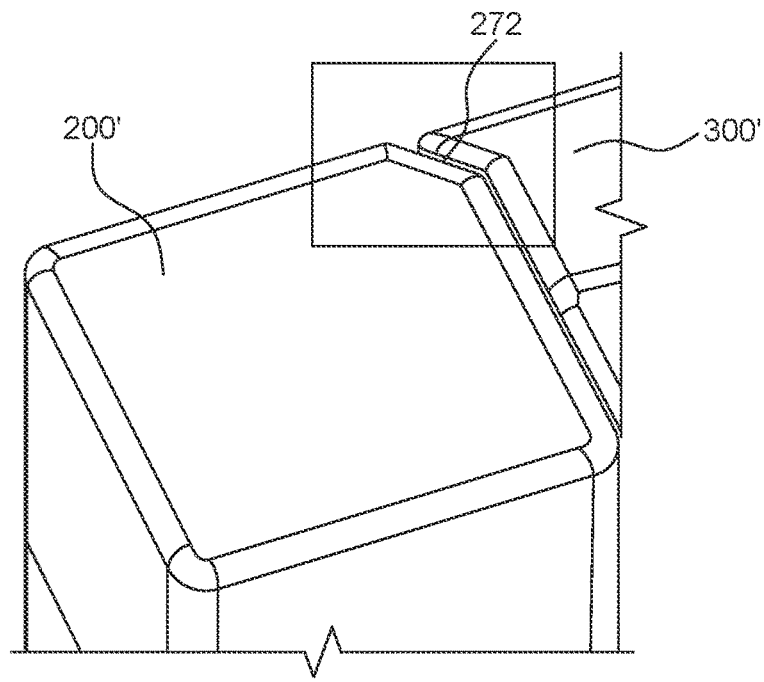
FIG. 28 is a detailed view of a connection between the storage device and the fluid cassette shown in FIG. 27.

In some embodiments or aspects, the storage device 200' can be configured such that the storage device 200' is connectable to a fluid cassette only in a particular orientation. In this manner, the access opening 254' on the door cover 252' of the storage device 200' can be properly aligned with the fluid cassette for proper connection of the vessel access member with the access port 232' on the vessel 226'. With reference to FIGS. 15-17B, the housing 201' of the storage device 200' includes a guide mechanism 272 that is configured for positioning the storage device 200' in a desired orientation relative to the fluid cassette 300 (see FIG. 28, for example). In some embodiments or aspects, the guide mechanism 272 includes one or more geometric features such as grooves, chamfers, projections, holes or tabs, etc. that can be configured to mate with corresponding features of the fluid cassette 300 for providing a direct connection to the fluid cassette 300 in a pre-determined orientation.

Figure 17A:
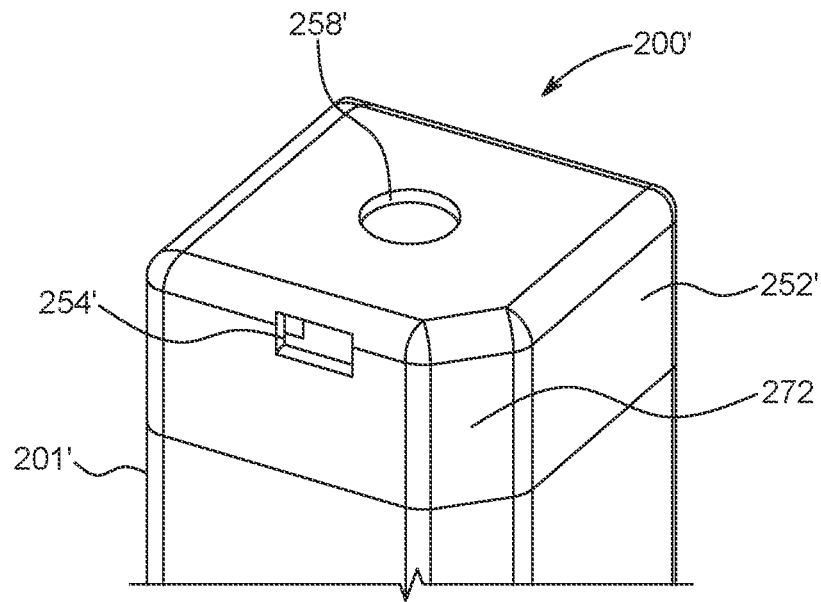
FIGS. 17A-17B show bottom perspective views of storage devices in accordance with some embodiments or aspects of the present disclosure.
Figure 17B:
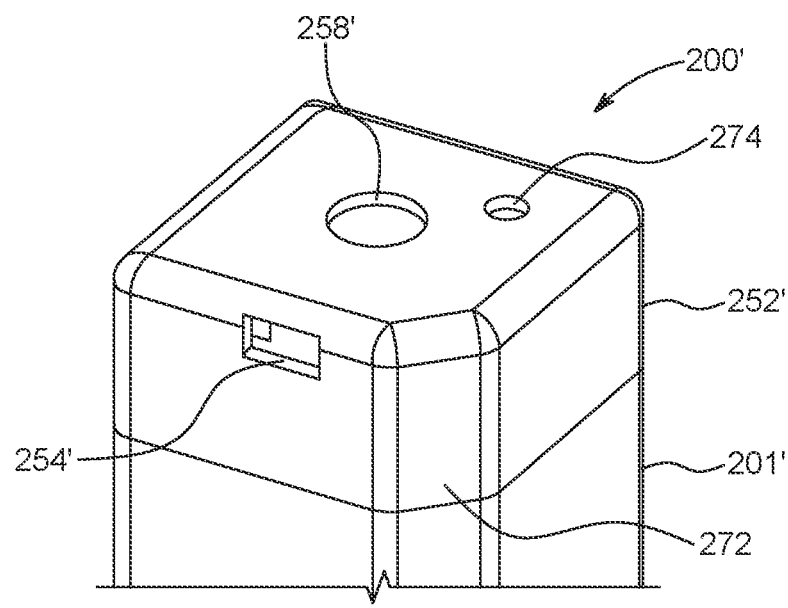

With reference to FIGS. 17A-17B, the storage device 200' may have at least one identification feature 274 (shown in FIG. 17B) that may be used to identify a particular characteristic of the storage device 200', such as the type of therapeutic or diagnostic agent in the storage device 200'. The at least one identification feature 274 may be one or more geometric features or physical indicia such as grooves, chamfers, projections, holes or tabs, etc. Such geometric features can be used to identify a particular storage device 200' and/or verify that the storage device 200' is an authentic storage device 200'. The at least one identification feature 274 may have a corresponding identification feature on the fluid cassette 300. The same or different identification features 274 may be used in relation to other aspects of the system, for example the storage compartment 108 and the used container compartment 112. This provides tangible feedback that the drugs in the storage containers 200' are compatible with the shielding and temperature capabilities of the applicable storage compartments.

In some embodiments or aspects, at least a portion of the housing 201' of the storage device 200' may have a colored portion that may be used for identifying purposes. For example, a particular color on at least a portion of the housing 201' of the storage device 200' may be used for identifying the contents of the storage device 200', such as the type of the therapeutic or diagnostic agent contained therein. In some embodiments or aspects, a particular color on at least a portion of the housing 201' of the storage device 200' may be used for identifying the storage device 200' as a storage device 200' intended for training purposes only. Such a storage device 200' would not contain any therapeutic or diagnostic agent but a safe, harmless liquid, optionally with coloring so that its behavior can be visualized.

Figure 18:
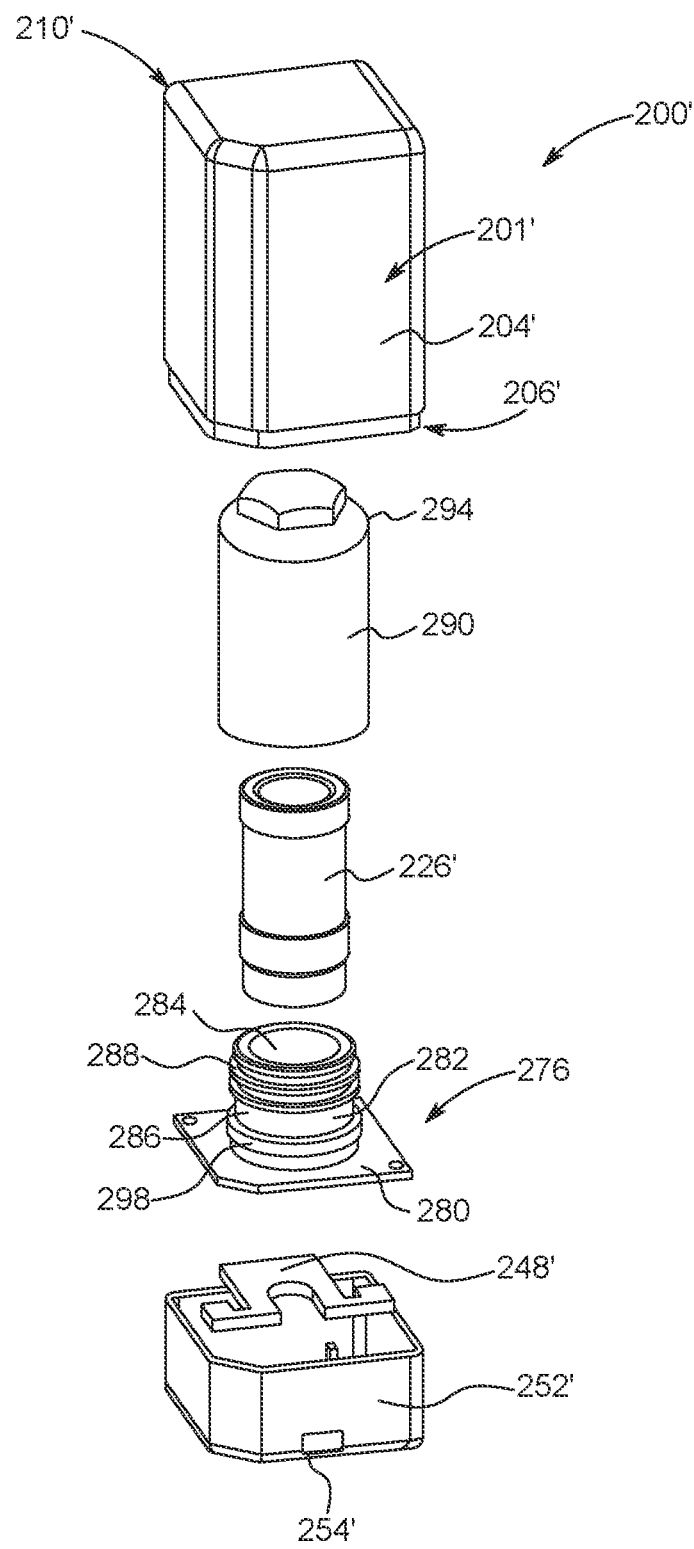
FIG. 18 is an exploded perspective view of the storage device shown in FIG. 15.
Figure 19:
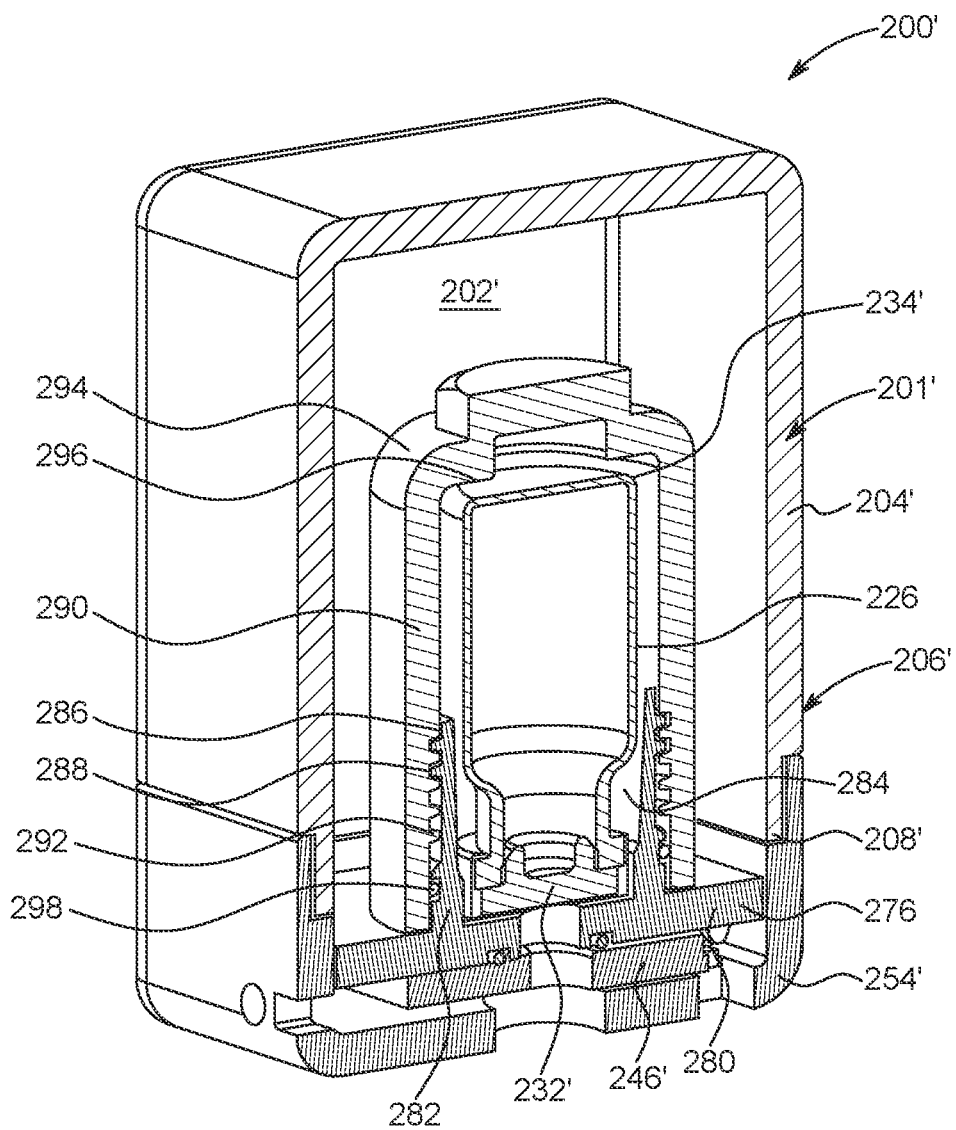
FIG. 19 is a cross-sectional perspective view of the storage device shown in FIG. 15.

With reference to FIGS. 18-19, the storage device 200'includes a housing 201' having a chamber 202' defined therein (shown in FIG. 19). The housing 201' has a main body 204' with a proximal end 206' with a first opening 208' and a closed distal end 210'. Instead of having a cap 214 at the distal end 210, such as shown in the storage device 200 in FIGS. 7-9, the storage device 200' shown in FIGS. 18-19 has a proximal cap 276 that is configured to enclose the first opening 208' at the proximal end 206' of the housing 201'.

With continued reference to FIGS. 18-19, the proximal cap 276 has a retainer 278 having a base 280 connectable to at least one of the main body 204' and the door cover 252' and a retaining portion 282 protruding distally from the base 280. The retaining portion 282 has a substantially cylindrical shape having an inner surface 284 configured to engage the vessel 226' and an outer surface 286 having a threaded collar 288. The threaded collar 288 is configured to threadably engage with a cover 290 that encloses the vessel 226' within the chamber 202'. The cover 290 has threads 292 configured to threadably engage with the threaded collar 288 on the retaining portion 282. A distal end 294 of the cover 290 has an inner engagement surface 296 configured to contact the distal end 234' of the vessel 226'. A seal 298 may be provided at an interface between the retaining portion 282 and the cover 290.

Figure 20:
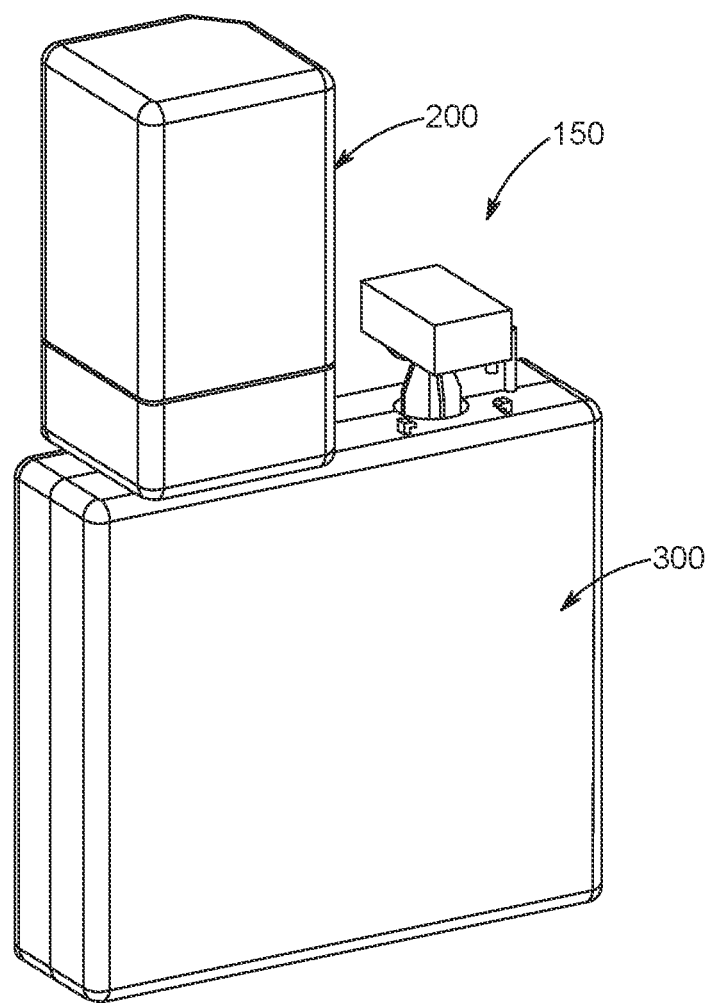
FIG. 20 is a perspective view of a storage device and a fluid cassette for administering a dose from the storage device in accordance with some embodiments or aspects of the present disclosure.

With reference to FIG. 20, an assembly 150 having a storage device 200 and a fluid cassette 300 is shown in accordance with some embodiments or aspects of the present disclosure. As described herein, the assembly 150 is configured to deliver the therapeutic or diagnostic agent from the storage device 200 via the fluid cassette 300 using the injector 170 (shown in FIG. 5). The fluid cassette 300 is configured to be removably connectable to the injector 170 and may be connected to a saline source for a saline flush application, priming, a saline test injection, and a saline infusion. The fluid cassette 300 is further configured to connect to the vessel 226 (shown in FIG. 8) of the storage device 200 to deliver the therapeutic or diagnostic agent 228 to a patient using the injector 170.

In some embodiments or aspects, the storage device 200 and the fluid cassette 300 may be configured to be removably connectable to each other. In other embodiments or aspects, the storage device 200 and the fluid cassette 300 may be configured to be non-removably connectable to each other, such that when the storage device 200 is connected to the fluid cassette 300, the storage device 200 cannot be removed from the fluid cassette 300. This type of interlocked connection helps prevent any undesired contact with the therapeutic or diagnostic agent. Each fluid cassette 300 can be adapted for connection to one storage device 200 or a pair of storage devices 200. In further embodiments or aspects, the fluid cassette 300 may only be fluidly connectable to the storage device 200, without any direct physical connection between housings thereof.

Figure 21:
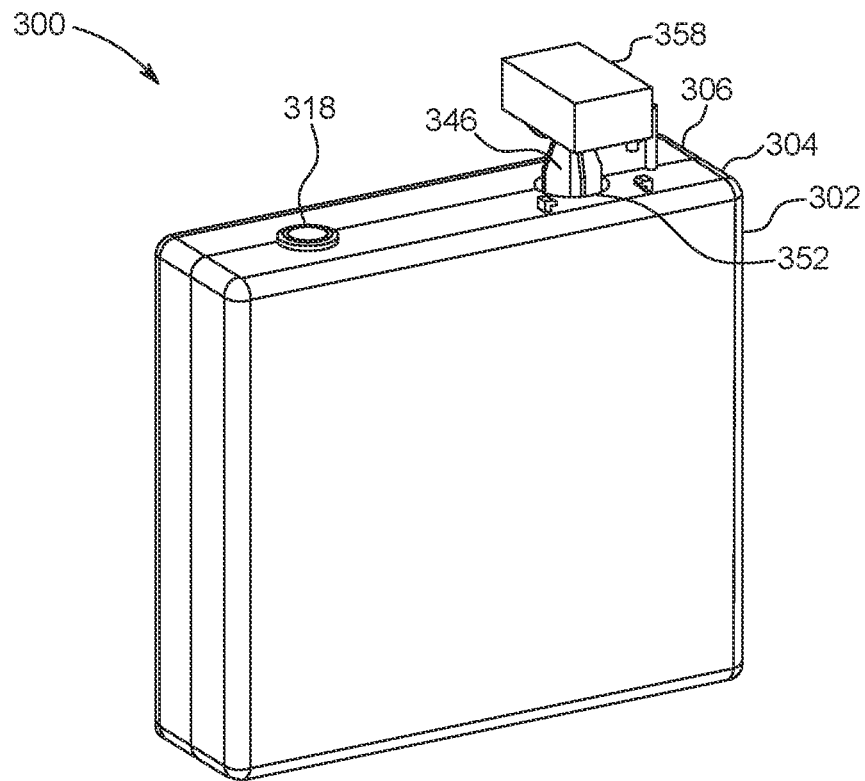
FIG. 21 is a perspective view the fluid cassette shown in FIG. 20.

With reference to FIG. 21, the fluid cassette 300 is shown without the storage device shown in FIG. 20. The fluid cassette 300 includes an enclosure 302 that encloses various components of the fluid cassette 300. The enclosure 302 has a first portion 304 and a second portion 306. The first and second portions 304, 306 may be removably or non-removably connectable to each other. In some embodiments or aspects, the fluid cassette 300 may have a substantially cuboid shape.

Figure 22:
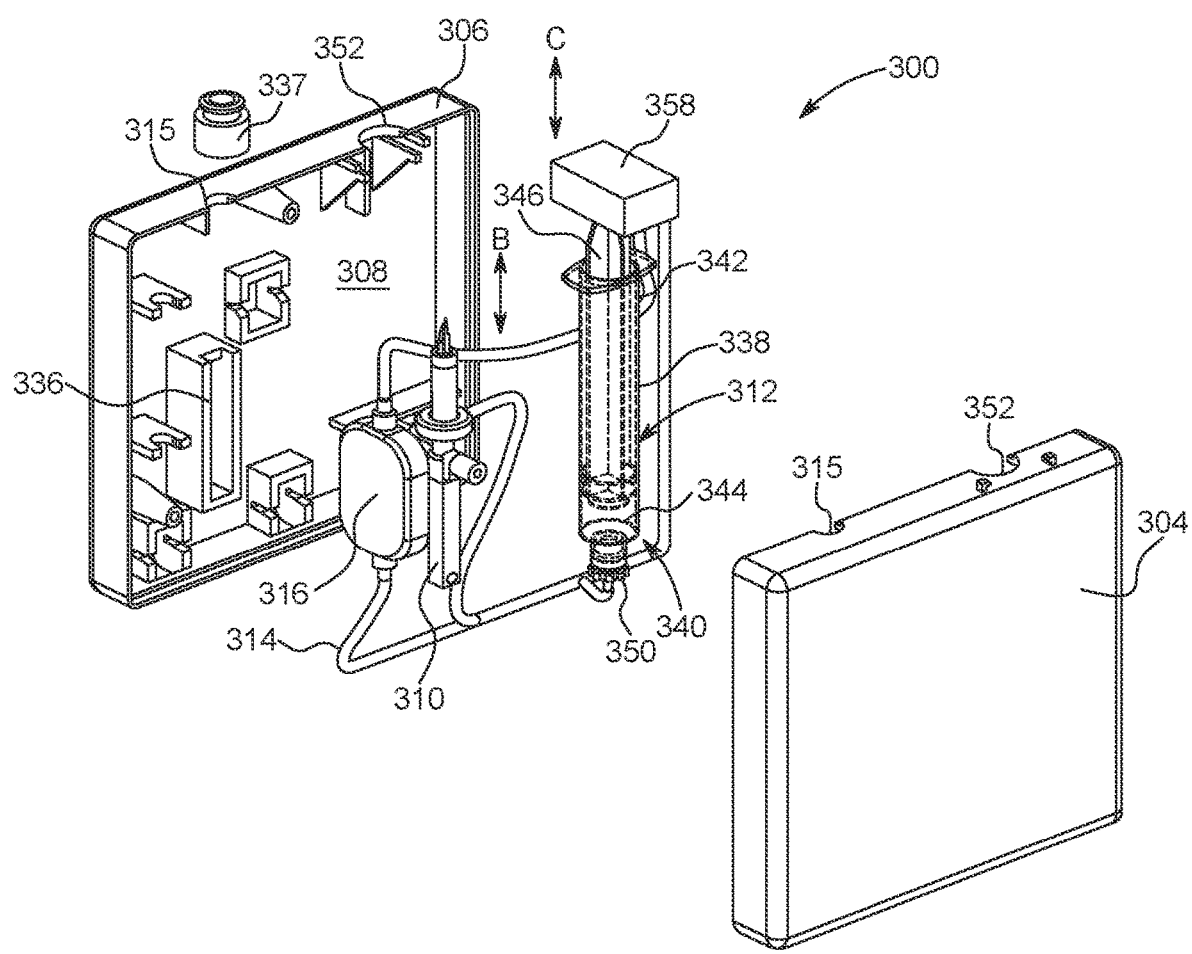
FIG. 22 is an exploded perspective view of the fluid cassette shown in FIG. 21.

With reference to FIG. 22, the first and second portions 304, 306 of the enclosure 302 of the fluid cassette 300 define an interior 308 configured to receive components of the fluid cassette 300. In some embodiments or aspects, the fluid cassette 300 may have a vessel access member, such as a spike 310, a metering device, such as a syringe 312, and a fluid path set 314 received within the interior 308 of the enclosure 302. The fluid path set 314 has tubing that fluidly connects the spike 310 to the syringe 312. In some embodiments or aspects, the fluid path set 314 may have a particle/air filter 317 (shown in FIG. 31). In further embodiments or aspects, the fluid path set 314 may have a valve block, as described herein with reference to FIG. 31. In some embodiments, the valve block may have one or more valves to control fluid flow through the spike 310, the syringe 312, and the fluid path set 314. The fluid path set 314 is further configured for connecting to an infusion set, to be described herein with reference to FIG. 31.

With continued reference to FIG. 22, the spike 310 is configured to be extendable through a spike opening 315 in the enclosure 302 between a retracted position and an extended position in a direction of arrow B. In the retracted position, the spike 310 is contained within the interior 308 of the enclosure 302. In the extended position, the spike 310 protrudes from the interior 308 of the enclosure 302 through the spike opening 315 such that the spike 310 is insertable through the access port 232 of the vessel 226 (shown in FIG. 8). An alignment element 337 may be provided on the spike opening 315 of the fluid cassette 300 for aligning the storage device 200 relative to fluid cassette 300 such that the spike 310 is axially aligned for insertion into the access portion 232 of the vessel 226 when the storage device 200 is connected to the fluid cassette 300. A cap may be provided for enclosing the spike opening 315 prior to use of the fluid cassette 300.

Figure 23:
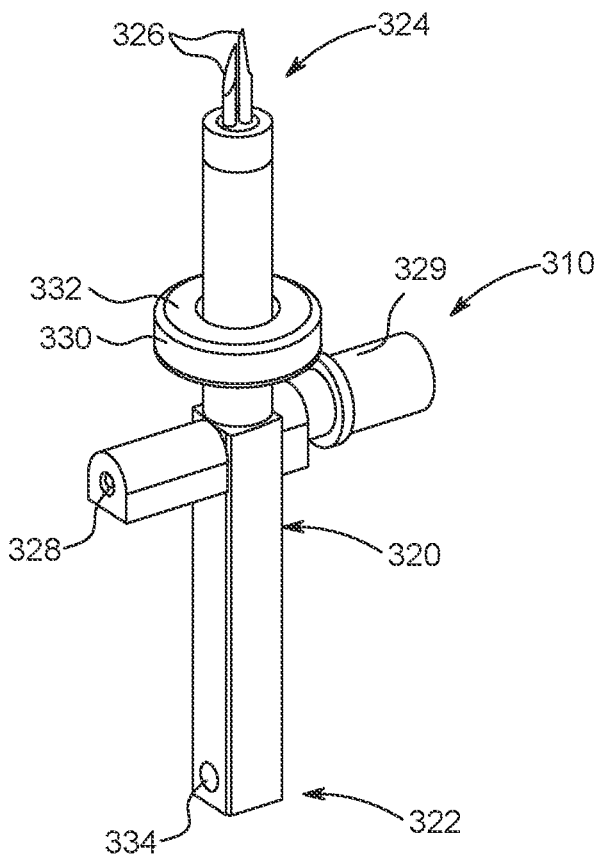
FIG. 23 is a perspective view of a vessel access member configured to pierce a vessel of a storage device in accordance with some embodiments or aspects of the present disclosure.

As shown in FIG. 23, the spike 310 has a body 320 with a proximal end 322, a distal end 324, and a hollow interior. The distal end 324 of the spike 310 has at least one piercing tip 326 configured for piercing the access port 232 of the vessel 226 (shown in FIG. 8). The at least one piercing tip 326 may include two piercing tips 326, with a first of the two piercing tips 326 being configured to withdraw fluid from the vessel 226, and the second of the two piercing tips 326 being configured to deliver air into the vessel 226 as the fluid is withdrawn therefrom. The at least one piercing tip 326 is in fluid communication with the hollow interior of the body 320 of the spike 310 to deliver fluid from the access port 232 of the vessel 226 to a fluid path connector 328, which is adapted to connect to the fluid path set 314. In this manner, the therapeutic or diagnostic agent from the vessel 226 can be delivered to the fluid path set 314 via the at least one piercing tip 326 and the fluid path connector 328 of the spike 310. In some embodiments or aspects, the spike may have a filtered vent 329 configured to allow air to enter the vessel 226 as fluid is withdrawn from the vessel 226. The spike 310 may have a collar 330 extending around the body 320. In some embodiments or aspects, an absorbent material 332 may be provided on the collar 330 for absorbing any drips from the access port 232 as the spike 310 is inserted into the access port 232 or withdrawn from the access port 232. The spike 310 further has a drive element 334 configured for engagement with a spike drive of the delivery system, as described herein. The drive element 334 may be an opening, slot, or other feature configured to be engaged by the spike drive of the delivery system for moving the spike 310 between the retracted position and the extended position. As shown in FIG. 22, a spike drive slot 336 may be provided on the enclosure 302 such that the spike drive of the delivery system can extend into the interior 308 of the enclosure 302 to engage the spike 310.

With reference to FIG. 22, the syringe 312 has a barrel 338 with a proximal end 340 opposite a distal end 342 and an interior chamber 344 defined therebetween. The proximal end 340 is open and is configured to receive a plunger 346. The distal end 342 has a port 350 in fluid communication with the fluid path set 314. The plunger 346 is reciprocally movable within the barrel 338 of the syringe 312 via a syringe drive of the delivery system, as described herein. The plunger 346 is movable is a direction of arrow C, wherein movement of the plunger 346 in the proximal direction draws fluid into the interior chamber 344 via the port 350, and wherein movement of the plunger 346 in the distal direction expels fluid from the interior chamber 344 via the port 350. As shown in FIG. 21, a portion of the plunger 346 protrudes from the enclosure 302 through a plunger opening 352. In some embodiments or aspects, the syringe drive of the delivery system may be configured to engage a proximal end of the plunger 346 that protrudes through the plunger opening 352. In other embodiments or aspects, the plunger 346 may be entirely contained within the housing 302 of the fluid cassette 300.

Figure 24:
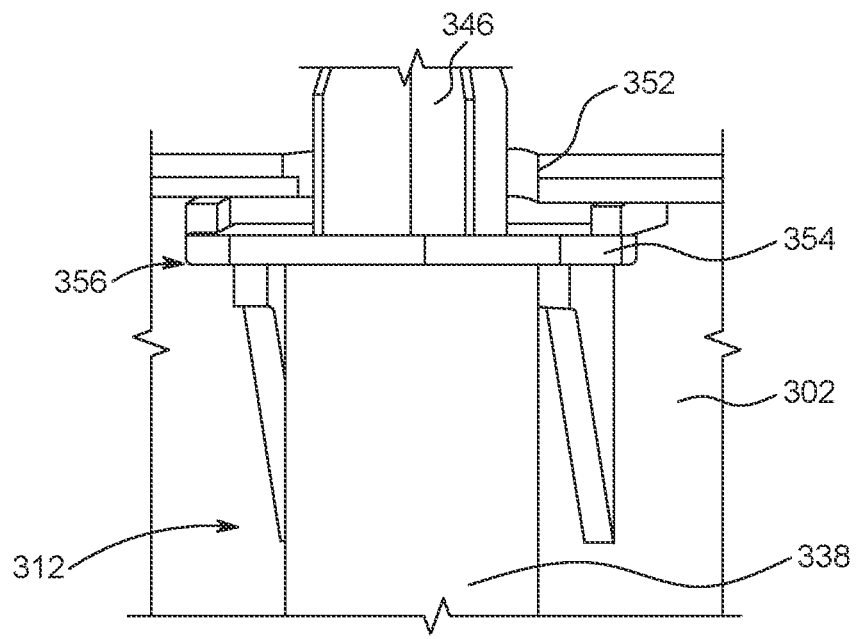
FIG. 24 is a detailed perspective view of a metering device connection interface of a fluid cassette in accordance with some embodiments or aspects of the present disclosure.

With reference to FIG. 24, the barrel 338 of the syringe 312 has a flange 354 protruding radially outward from the barrel 338 at the distal end 342. The flange 354 is configured to be received in a flange slot 356 on the enclosure 302 to prevent movement of the barrel 338 relative to the enclosure 302 as the plunger 346 is reciprocally moved within the barrel 338. The flange slot 356 may have a tapered geometry to ensure a tight fit with the flange 354.

Figure 25A:
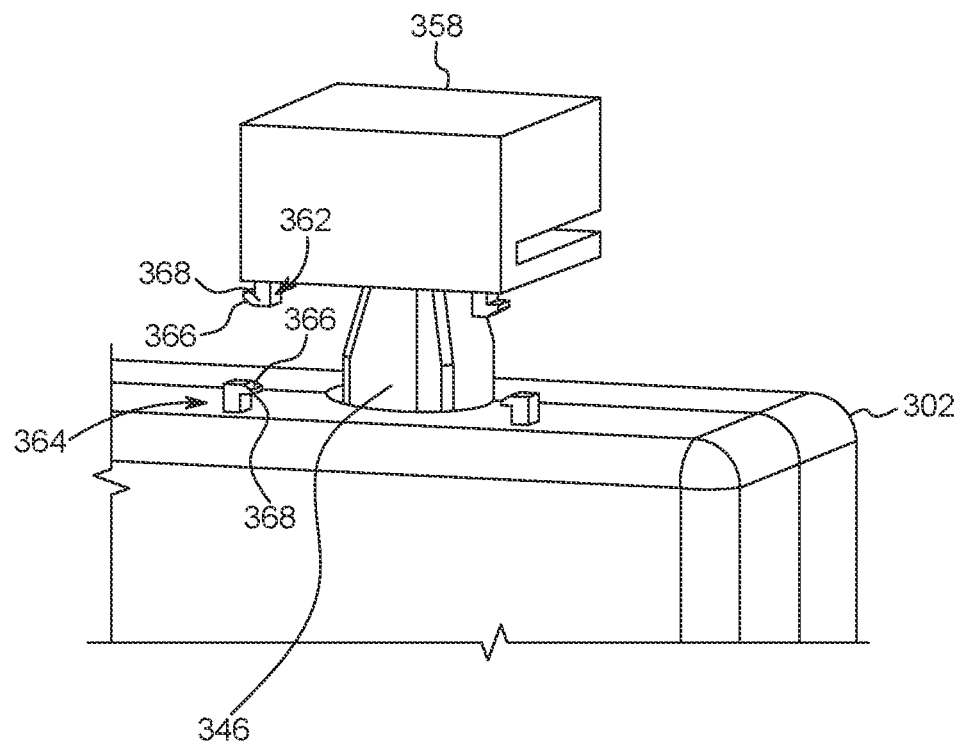
FIG. 25A is a perspective view of a plunger cap shown in an unlocked position.
Figure 25B:
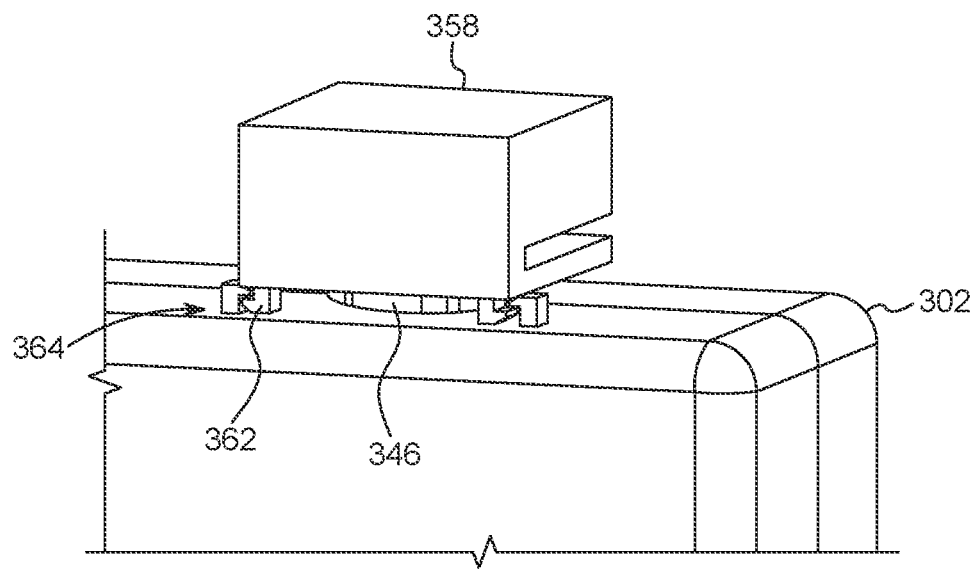
FIG. 25B is a perspective view of the plunger cap of FIG. 25A shown in a locked position.

With reference to FIGS. 25A-25B, the plunger 346 has a plunger cap 358 configured for locking the plunger 346 in a locked position and preventing movement thereof such that filling and dispensing functionality of the syringe 312 (shown in FIG. 22) is disabled. In some embodiments or aspects, the plunger cap 358 may be shipped in a locked configuration and the injector 170 may be configured to unlock the plunger cap 358 to permit movement of the plunger 346 for filling and dispensing functionality. In some embodiments or aspects, the plunger cap 358 has at least one first hook 362 that is configured to engage with at least one second hook 364 on the enclosure 302. Each of the at least one first hook 362 and the at least one second hook 364 may have an angled contact surface 366 and a catch 368 that is configured to engage once the two contact surfaces 366 slide past each other. FIG. 25B shows the at least one first hook 362 and the at least one second hook 364 in a locked engagement with each other when the plunger cap 358 is urged toward the enclosure 302. Due to this locked engagement, the plunger 346 cannot be moved to fill the syringe 312 with fluid or dispense fluid from the syringe 312. The plunger cap 358 is further configured to maintain a position of the syringe 312 in a set position such that the plunger 346 can be connected to the plunger drive mechanism during installation of the fluid cassette 300 into the delivery device 100.

Figure 26:
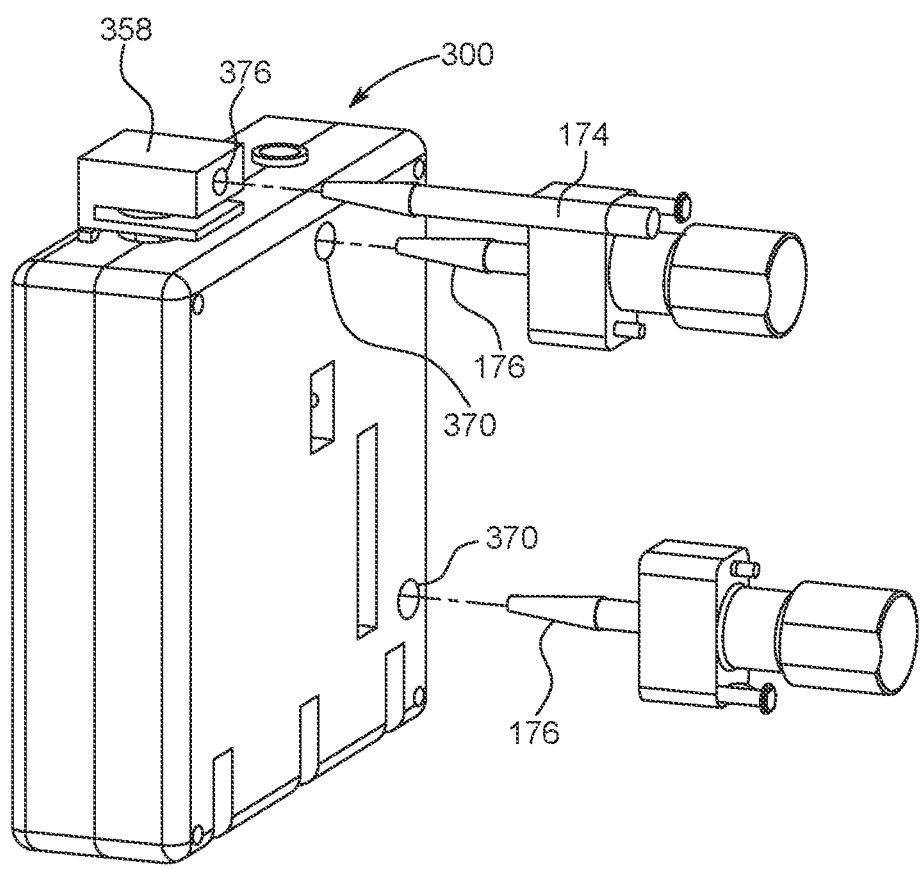
FIG. 26 is a perspective view of a fluid cassette and components of a delivery system configured for interacting with the fluid cassette in accordance with some embodiments or aspects of the present disclosure.

With reference to FIG. 26, the fluid cassette 300 has one or more alignment elements 370 for aligning the fluid cassette 300 relative to the injector 170 of the delivery system 100 (shown in FIG. 5). In some embodiments or aspects, the enclosure 302 of the fluid cassette 300 has a pair of alignment elements 370 configured as openings shaped to receive alignment pins 176 of the injector 170 (also shown in FIG. 31). Each of the pins 176 has a tapered surface configured for locating the alignment elements 370 on the fluid cassette 370 as the alignment pins 176 are moved in a direction toward the fluid cassette 370. Once the alignment pins 176 are inserted into the alignment elements 370, the fluid cassette 300 is positioned in a desired position relative to the injector 170 such that the spike 310 and the plunger 346 can be operated. For example, alignment of the alignment pins 176 with the alignment elements 370 on the fluid cassette 300 also aligns a delivery mechanism 174 with a corresponding plunger drive receiver 376 on the plunger cap 358 to move the plunger 346 during filling and dispensing operations. The plunger drive receiver 376 may have a tapered shape that corresponds to a tapered shape of the pin on the delivery mechanism 174. In some embodiments or aspects, the alignment elements 370 further facilitate alignment of valves and sensors of the delivery device 100 with corresponding locations on the fluid path set 314 in the fluid cassette 300.

With reference to FIGS. 27-30, a fluid cassette 300' is shown in accordance with another embodiment or aspect of the present disclosure. As the structure of the fluid cassette 300' shown in FIGS. 27-30 is substantially similar to the structure of the fluid cassette 300 shown and described with reference to FIGS. 20-26, a detailed description of the components of the fluid cassette 300' will be omitted. The same reference numbers will be used in FIGS. 27-30 to describe the components of the fluid cassette 300' as used in FIGS. 20-26 to describe the components of the fluid cassette 300, except for the addition of a " ' " mark after each reference number in FIGS. 27-30. The following detailed disclosure will focus only on relative differences between the two storage devices.

Figure 27:
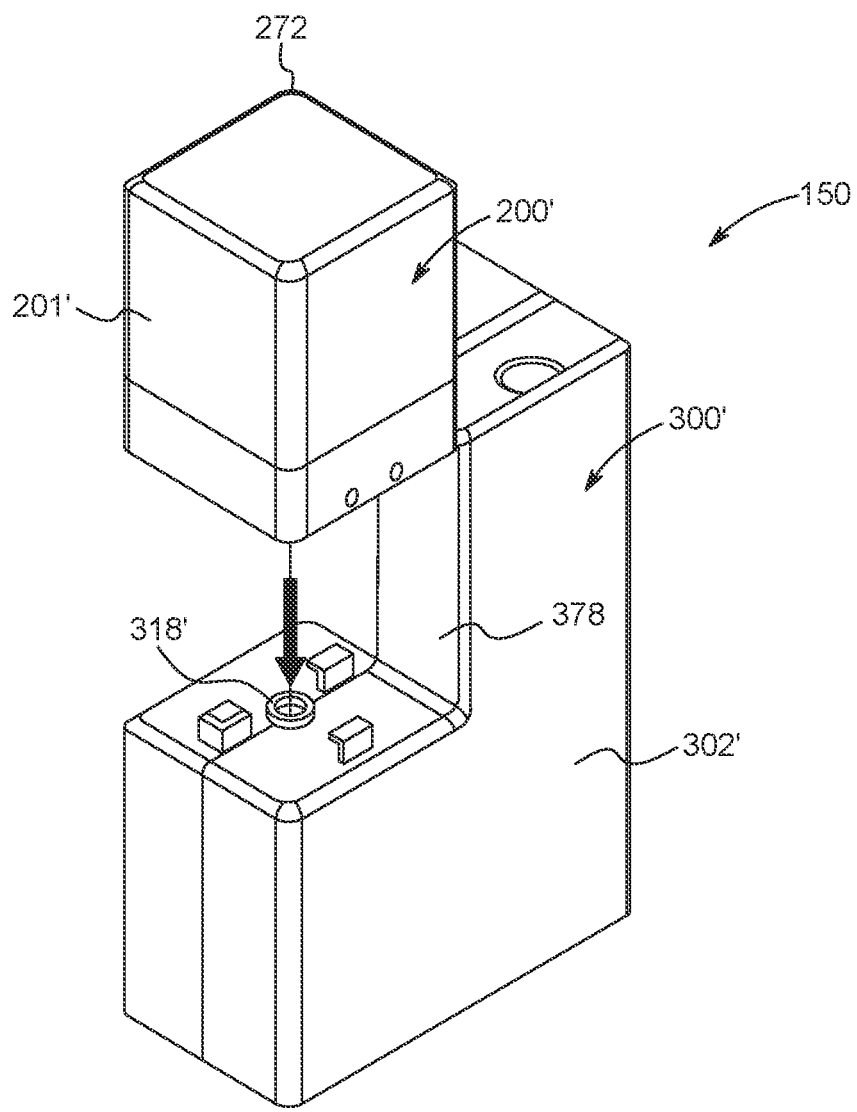
FIG. 27 is a perspective view of a storage device and a fluid cassette for administering a dose from the storage device in accordance with some embodiments or aspects of the present disclosure.
Figure 29:
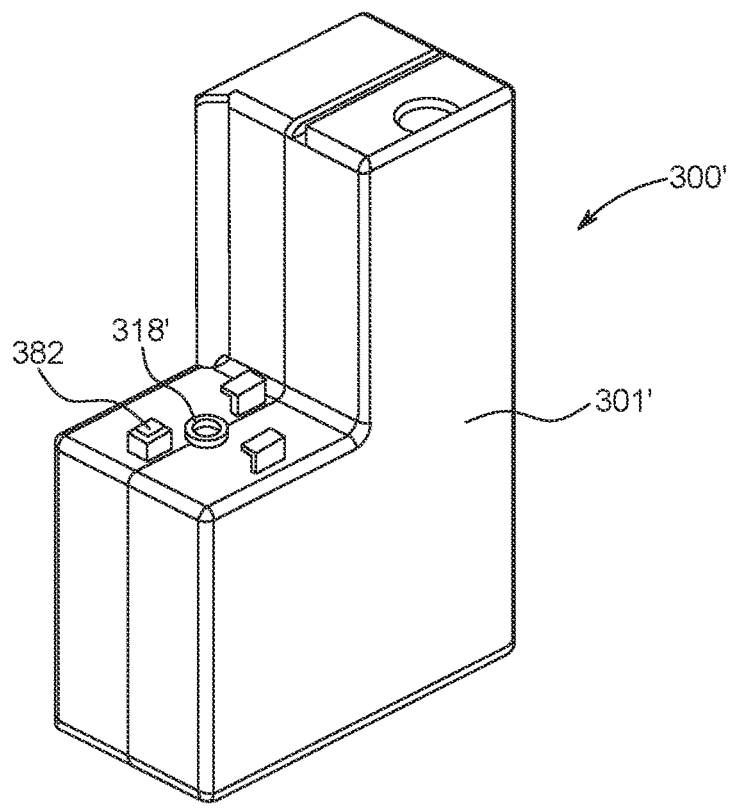
FIG. 29 is a perspective view the fluid cassette shown in FIG. 28.
Figure 30:
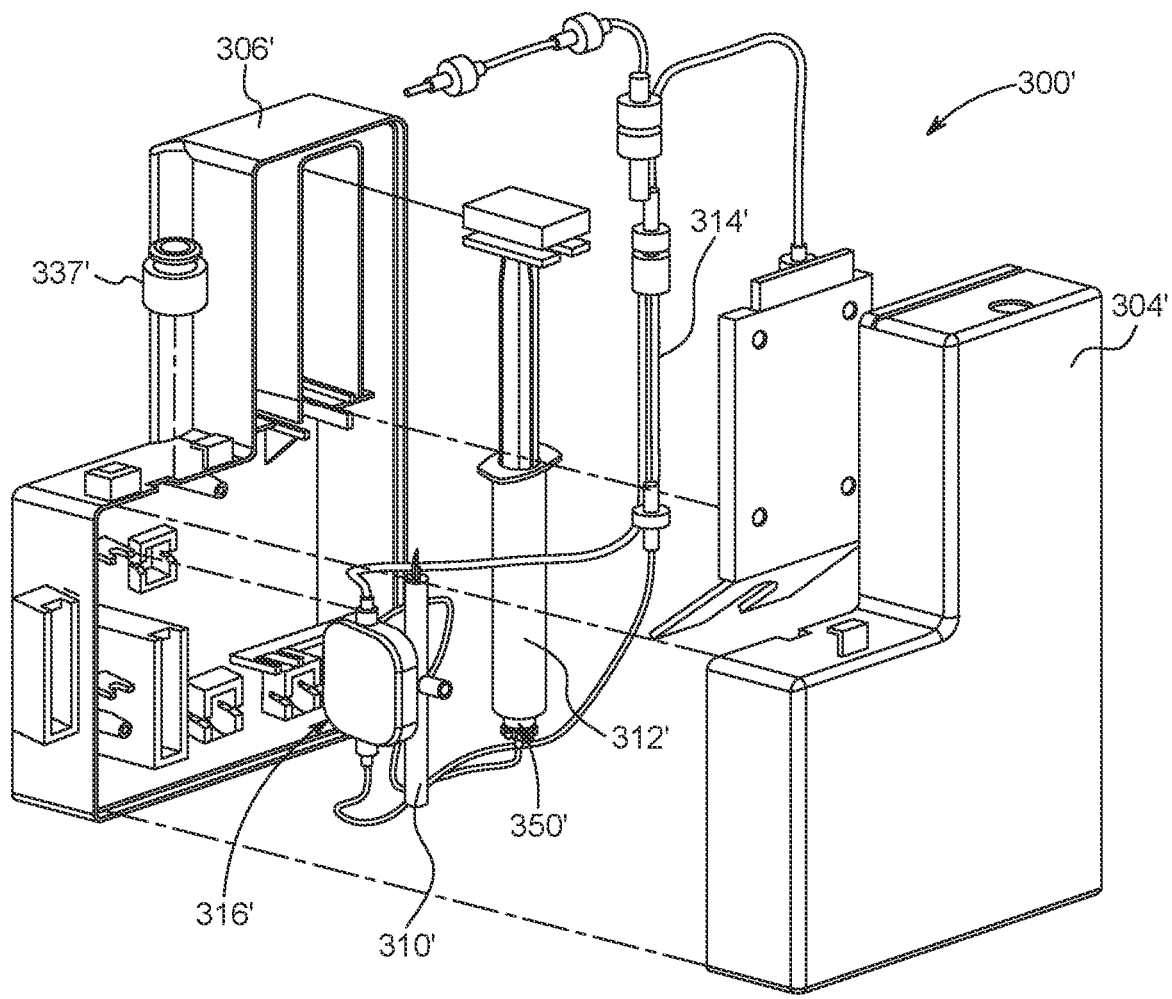
FIG. 30 is an exploded perspective view of the fluid cassette shown in FIG. 29.

With reference to FIG. 27, the fluid cassette 300' has an enclosure 302' with a recess 378 shaped to receive the storage device 200' shown in FIGS. 15-19. In some embodiments or aspects, the recess 378 is shaped such that the storage device 200' is connected to the fluid cassette 300', the resulting assembly 150 has a substantially cuboid shape. As discussed herein with reference to FIGS. 15-17B, the housing 201' of the storage device 200' includes a guide mechanism 272 that is configured for positioning the storage device 200' in a desired orientation relative to the fluid cassette 300'. For example, with reference to FIG. 28, the guide mechanism 272 includes one or more geometric features such as grooves, chamfers, projections, holes or tabs, etc. that can be configured to mate with corresponding guide features 380 of the fluid cassette 300' for providing a direct connection of the storage device 200' to the fluid cassette 300' in a pre-determined orientation. With reference to FIG. 29, the fluid cassette 300' has one or more locking elements 382 for non-removably connecting the storage device 200' to the fluid cassette 300'.

Figure 31:
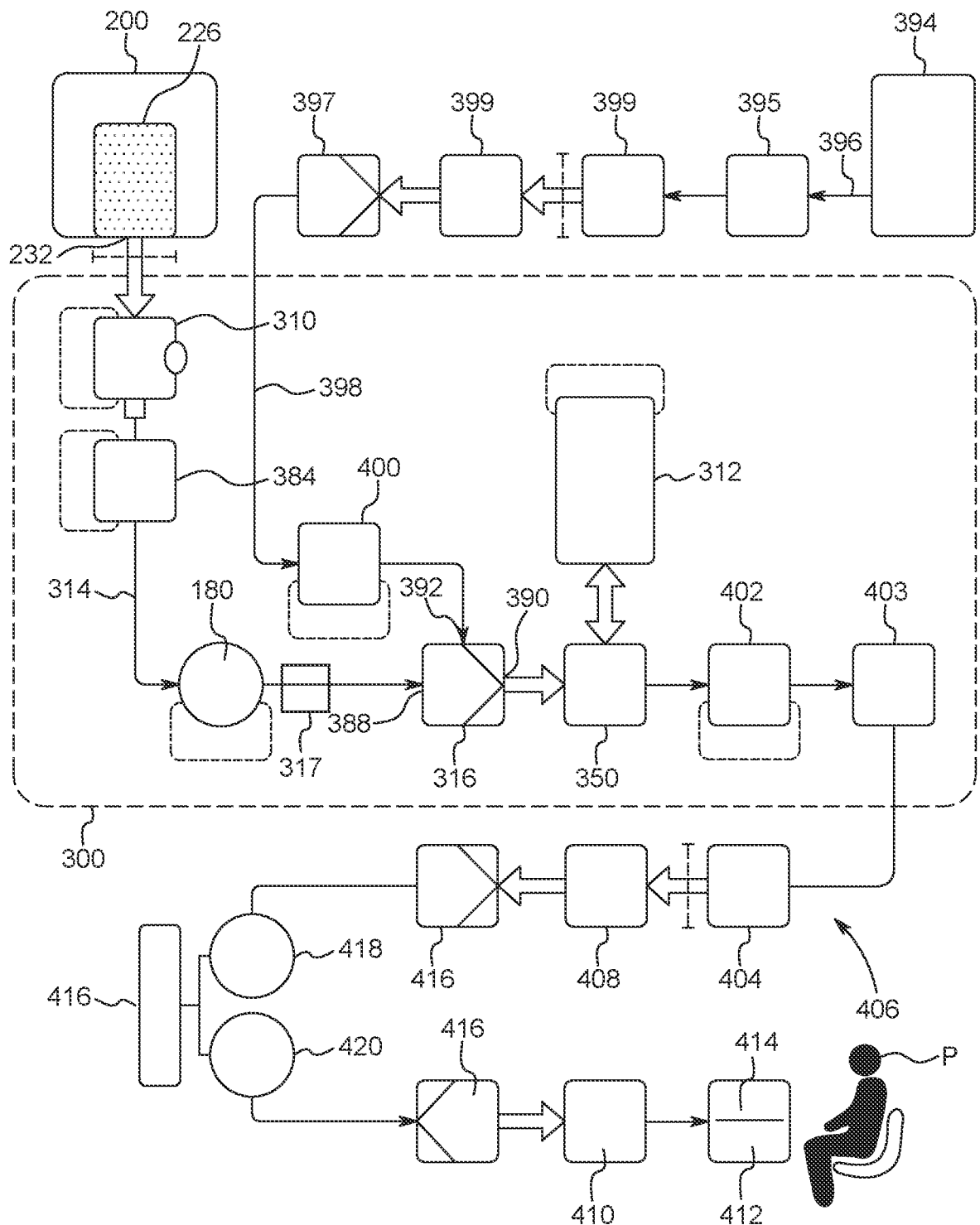
FIG. 31 is a schematic view of fluid connections between a vessel of a storage device, a fluid cassette, and a patient delivery line in accordance with some embodiments or aspects of the present disclosure.

With reference to FIG. 31, an exemplary fluid diagram is shown illustrating fluid pathways between the storage device 200 and the fluid cassette 300. As shown in FIG. 31, the vessel 226 of the storage device 200 is fluidly connectable to the fluid path set 314 of the fluid cassette 300 via the spike 310. The fluid path set 314 may have a plurality of valves to control flow of fluid from the vessel 226 to an infusion set 406. In some embodiments or aspects, a first valve 384 is provided downstream of the spike 310 to regulate fluid flow into the fluid path set 314 from the spike 310. In some embodiments or aspects, the first valve 384 may be a pinch valve, a stopcock valve, or any other type of a valve configured for selectively permitting fluid flow from the spike 310 into the fluid path set 314. In some embodiments or aspects, the first valve 384 may be operable between an open position and a closed position by the injector 170.

The flow path of the fluid path set 314 can be structured to facilitate air removal during priming and limit the formation of bubbles within the material being passed from the vessel 226 of the storage device 200 to the syringe 312, for example by limiting abrupt changes or transitions in the internal diameter of the tubing of the fluid path set 314. The flow path of the fluid path set 314 can further be structured to prevent any air bubbles from being passed from the syringe 312 to incorporate a tortuous fluid path to preferentially separate and divert bubbles or with a hydrophobic membrane. The flow path of the fluid path set 314 can be designed to incorporate valves or other fluidic control elements such as passive valve, active valves, one-way valves, diverting valves, pinch valves, rotary valves, stopcocks, or on-off valves.

With continued reference to FIG. 31, an air detector 180 is provided downstream of the first valve 384. The air detector 180 is configured to detect air within the fluid path set 314. In some embodiments or aspects, the air detector 180 is provided on the injector 170 (see FIGS. 5 and 32) and the fluid cassette 300 is positioned relative to the injector 170 such that the air detector 180 is configured to detect air in the fluid path set 314 at a location downstream of the first valve 384. In some embodiments or aspects, output from the air detector 180 may be used by the controller 114 of the delivery system 100 (shown in FIG. 5) to permit or prevent operation of the injector 170 depending on the absence or the presence of air in the fluid path set 314. The air detector 180 may be configured to detect the presence of the therapeutic or diagnostic agent in the line from the vessel 226 to aid with volumetric accuracy of dose delivery.

With continued reference to FIG. 31, the air/particle filter 317 is provided downstream of the air detector 180. In some embodiments or aspects, a valve block 316 is provided downstream of the air detector 180. In some embodiments or aspects, the valve block 316 may be a manifold having a plurality of ports that can be selectively opened or closed to permit or restrict fluid flow therethrough. For example, the valve block 316 may have a first port 388, a second port 390, and a third port 392. The valve block 316 is operable such that only two of the three ports can be in fluid communication with each other. For example, if the valve block 316 is arranged such that the first and second ports 388, 390 are in fluid communication with each other and in fluid isolation from the third port 392, the syringe 312 can be filled with the therapeutic or diagnostic agent from the vessel 226 via the port 350. If the valve block 316 is arranged such that the second and third ports 390, 392 are in fluid communication with each other and in fluid isolation from the first port 388, fluid from an auxiliary fluid source 394, such as a saline source, can be delivered to the port 350 of the syringe 312 via an auxiliary line 396. In this configuration, saline or other fluid can be delivered for a patency check, a test infusion, or a flush procedure, as discussed herein. The auxiliary line 396 is connectable to an auxiliary branch 398 of the fluid path set 314. The auxiliary line 396 has a spike 395 for connecting to the auxiliary fluid source 394, a check valve 397, and a pair of connectors 399.

In some embodiments, a second valve 400 may be provided on the auxiliary branch 398 for controlling fluid flow to the valve block 316. In some embodiments or aspects, the valve block 316 can be operated to selectively open or close the first, second, and third ports 388, 390, 392 via the injector 170. Similarly, the second valve 400 may be operable between open and closed positions via the injector 170.

With continued reference to FIG. 31, a third valve 402 is provided downstream of the port 350 of the syringe 312. The third valve 402 may be operable between open and closed positions via the injector 170. An air/particulate filter 403 is provided downstream of the third valve 402 prior to the fluid path set 314 terminating in an end connector 404.

With continued reference to FIG. 31, the infusion set 406 is removably connectable to the fluid path set 314 of the fluid cassette 300 via the end connector 404. The infusion set 406 has a proximal connector 408 configured for removably connecting with the end connector 404 of the fluid path set 314. In some embodiments or aspects, the end connector 404 and the proximal connector 408 may be Luer connectors. The infusion set 406 further has a distal connector 410 configured for connecting to a catheter 412 or a priming cap 414. A pair of check valves 416 are provided between the proximal and distal connectors 408, 410. In some embodiments or aspects, the infusion set 406 may be configured for connecting to a sensor arrangement 416 having an occlusion detection sensor 418 and an air detector 420. In some embodiments or aspects, the occlusion detection sensor 418 may be configured for pressure testing the integrity of the fluid path set 314 prior to access to the vessel 226.

Figure 32:
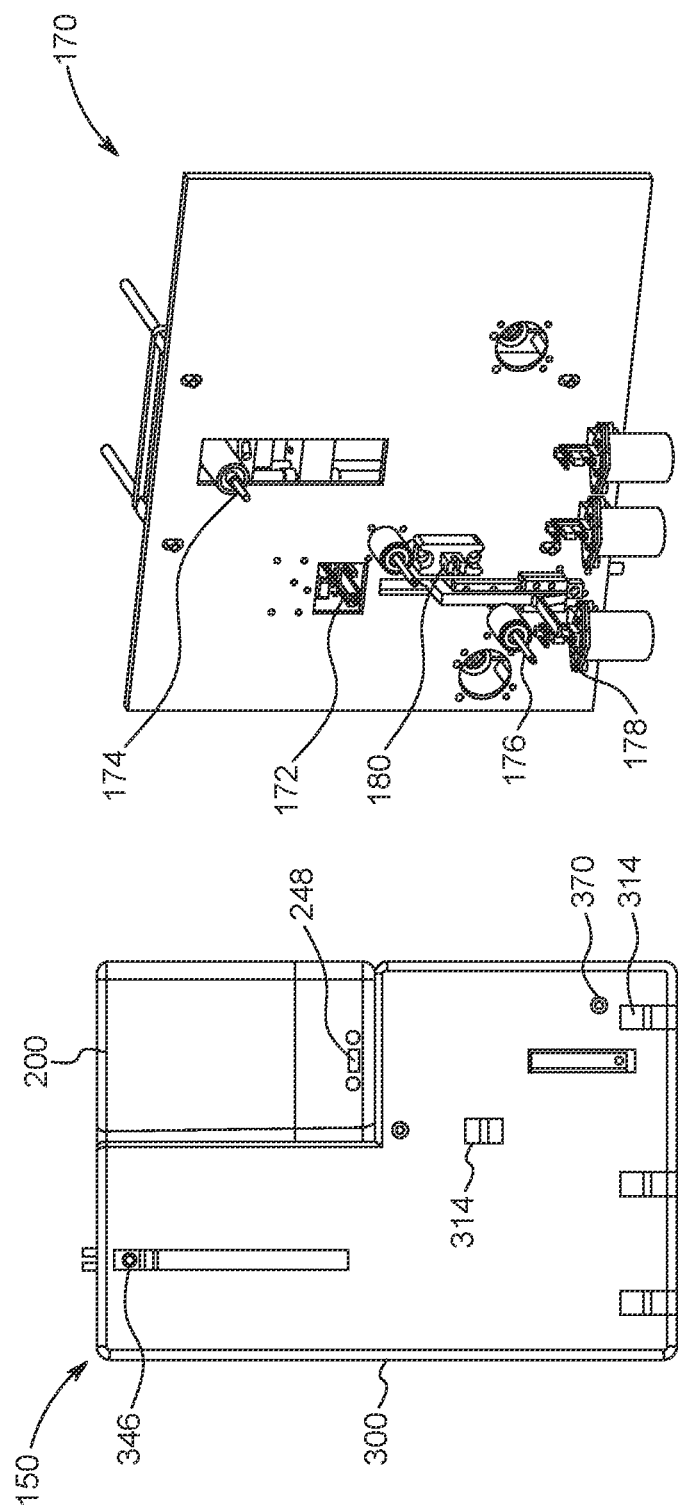
FIG. 32 is a perspective view of a fluid cassette and a storage device along with components of an infusion system configured for interacting with the fluid cassette and the storage device in accordance with some embodiments or aspects of the present disclosure.

With reference to FIG. 32, the fluid cassette 300 and storage device 200 are shown along with components of the injector 170 configured for interacting with the fluid cassette 300 and the storage device 200. In some embodiments or aspects, the injector 170 includes an access mechanism 172 configured for moving the door 248 of the storage device 200 (shown in FIG. 8) from the closed position to the open position. The injector 170 further includes a delivery mechanism 174 configured for actuating the plunger 346 of the syringe 312 to fill the syringe 312 with the therapeutic or diagnostic agent from the storage device 200 or to fill the syringe 312 with saline from the auxiliary fluid source 394 (shown in FIG. 31). The delivery mechanism 174 may be further configured for actuating the plunger 346 of the syringe 312 to deliver the contents of the syringe 312, such as the therapeutic or diagnostic agent, or saline, to the infusion set 406 (shown in FIG. 31). While the fluid cassette 300 and fluid path elements thereof have been shown with a single syringe 312 and valving to do the fluid movement and control, pumps other than a single syringe 312 may be used. In some embodiments or aspects, there may be multiple pumps, for example one syringe 312 each for the drug and the flushing fluid. In some embodiments, one or more of the pumps may be a peristaltic pump, a diaphragm pump, or a piston pump. In some embodiments, the additional pump may eliminate the need for some valves or may benefit from the use of additional valves. In some embodiments it is desirable to have separate pumps for drug and flushing fluid from auxiliary fluid source 394 to provide the ability to have dual flow, that is delivering the two fluids simultaneously, so that total volumetric flow rate may be set independently of drug delivery rate. One benefit of dilute introduction is to possibly reduce chance of patient discomfort or reaction. A second is to reduce the time that the TRT is in the infusing vein before it is conducted to and diluted in the central circulation. See for example U.S. 2021/0187186 A1, which incorporated herein by reference.

With continued reference to FIG. 32, the fluid injector has one or more alignment pins 176 configured for engaging with the one or more alignment elements 370 on the fluid cassette 300. Once the alignment pins 176 are inserted into the alignment elements 370, the fluid cassette 300 is positioned in a desired position relative to the injector 170 such that the spike 310 and the plunger 346 can be operated. The injector 170 further has the air detector 180 configured for detecting air within the tubing of the fluid path set 314. In some embodiments or aspects, the injector 170 further may have a fluid detector configured for detecting the presence of a fluid and/or other properties relating to the fluid. In some embodiments or aspects, the injector 170 further has a valve assembly 178 configured for selectively engaging the tubing of the fluid path set 314 to regulate fluid flow therethrough.

Figure 33:
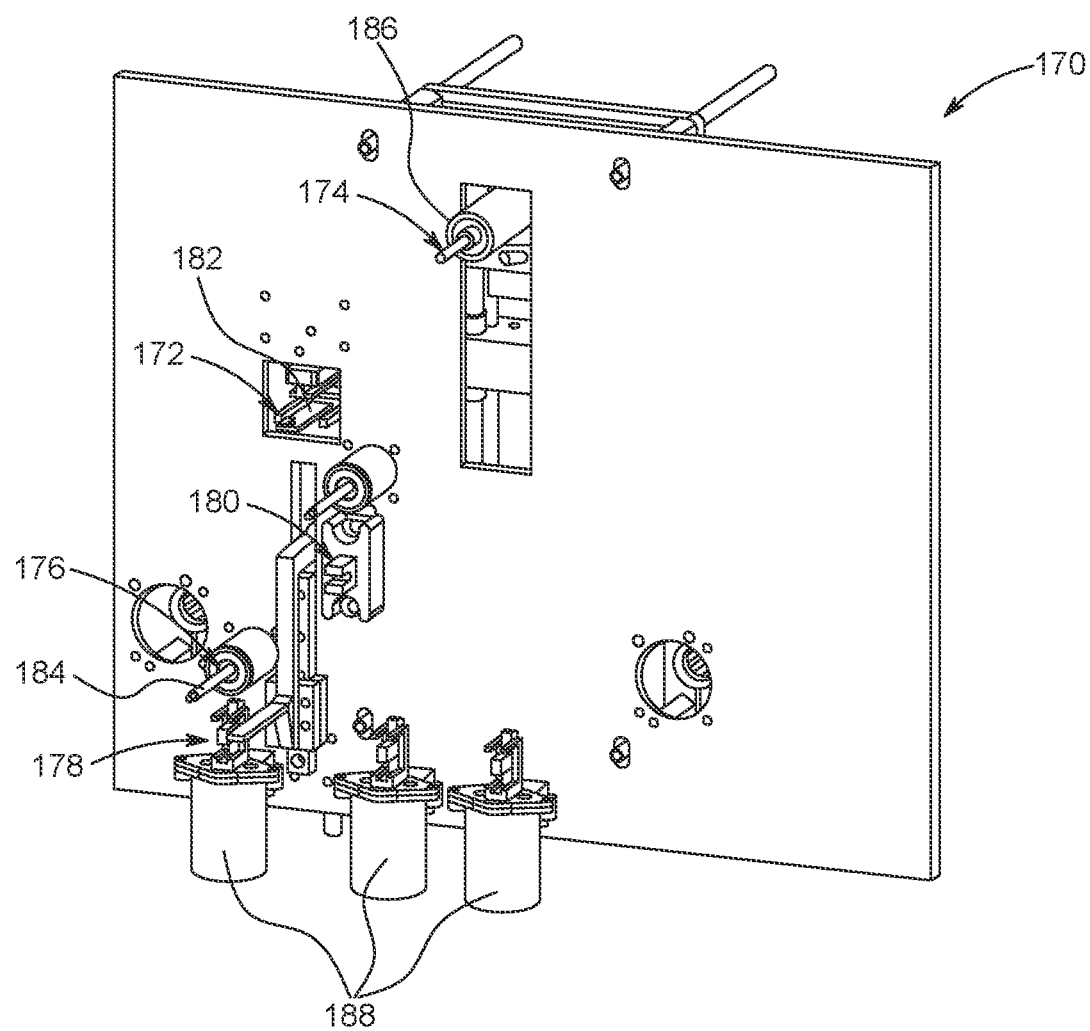
FIG. 33 is a perspective view of the components of an infusion system shown in FIG. 32.

Once the storage device 200 is coupled to the fluid cassette 300, and the combined assembly 150 is installed in the delivery system 100, the access mechanism 172 of the injector 100 is configured to move the door 248 from the closed position to the open position such that the spike 310 of the fluid cassette 300 can be extended to pierce through the access port 232 of the vessel 226. With reference to FIG. 33, the access mechanism 172 of the injector 170 may have a probe 182 configured to extend in a direction toward the door 248 through the access opening 254 in the door cover 252 (shown in FIG. 9). In some embodiments or aspects, the probe 182 may be configured to pierce through the seal 256 on the access opening 254. The probe 182 may be configured to sense the presence of the seal 256, such as by sensing a resistance to movement through the door access opening 254 when the seal 256 is present compared to a resistance to movement when the seal 256 is absent. If the probe 182 does not detect the seal 256, such as due to no resistance to movement through the door access opening 254, the controller 114 (shown in FIG. 5) may be configured to prevent operation of the delivery system 100 because a used storage device 200 (i.e., one with a pierced seal 256), or a tampered storage device 200 (i.e., one with a removed seal 256) has been installed on the fluid. Operation of the probe 182 may be controlled via the controller 114.

With continued reference to FIG. 33, the access mechanism 172 of the fluid injector further may include a spike driver 184 configured for engaging with a spike drive slot 336 (shown in FIG. 23) of the spike 310. The spike driver 184 may be movable in a linear direction from a first position, which corresponds to a retracted state of the spike 310, and a second position, which corresponds to an extended state of the spike 310 in which the spike 310 pierces the access port 232 of the vessel 226. Operation of the spike driver 184 may be controlled via the controller 114.

With continued reference to FIG. 33, the delivery mechanism 174 includes a plunger driver 186 configured for actuating the plunger 346 of the syringe 312 to cause the plunger 346 to move within the barrel of the syringe 312. The plunger driver 186 is shaped to be received in the plunger drive receiver 376 such that movement of the plunger driver 186 causes a corresponding movement of the plunger 346. The plunger driver 186 may have a motor for moving the plunger 346 in a linear direction. The plunger driver 186 may be movable in a linear direction in a first direction, in which the barrel of the syringe 312 is configured to be filled with fluid, and a second direction opposite the first direction, in which fluid from the barrel of the syringe 312 is configured to be delivered via the port 350. Operation of the plunger driver 186 may be controlled via the controller 114. In some embodiments or aspects, the plunger driver 186 determines a flow rate of the fluid that is delivered to the patient.

With continued reference to FIG. 33, the air detector 180 is configured for detecting air within the tubing of the fluid path set 314. The air detector 180 may be an optical air detector, an acoustic air detector, an ultrasonic air detector, or any other air detector configured for detecting a presence of air in the tubing of the fluid path set 314. Operation of the air detector 180 may be controlled via the controller 114.

With continued reference to FIG. 33, the valve assembly 178 may include a plurality of valves 188. In some embodiments or aspects, the plurality of valves 188 may be pinch valves configured to pinch the tubing of the fluid path set 314. In some embodiments or aspects, the valves 188 may be rotary stopcocks or other fluid flow shutoff mechanisms. Operation of the valve assembly 178 may be controlled via the controller 114.

Figure 34:
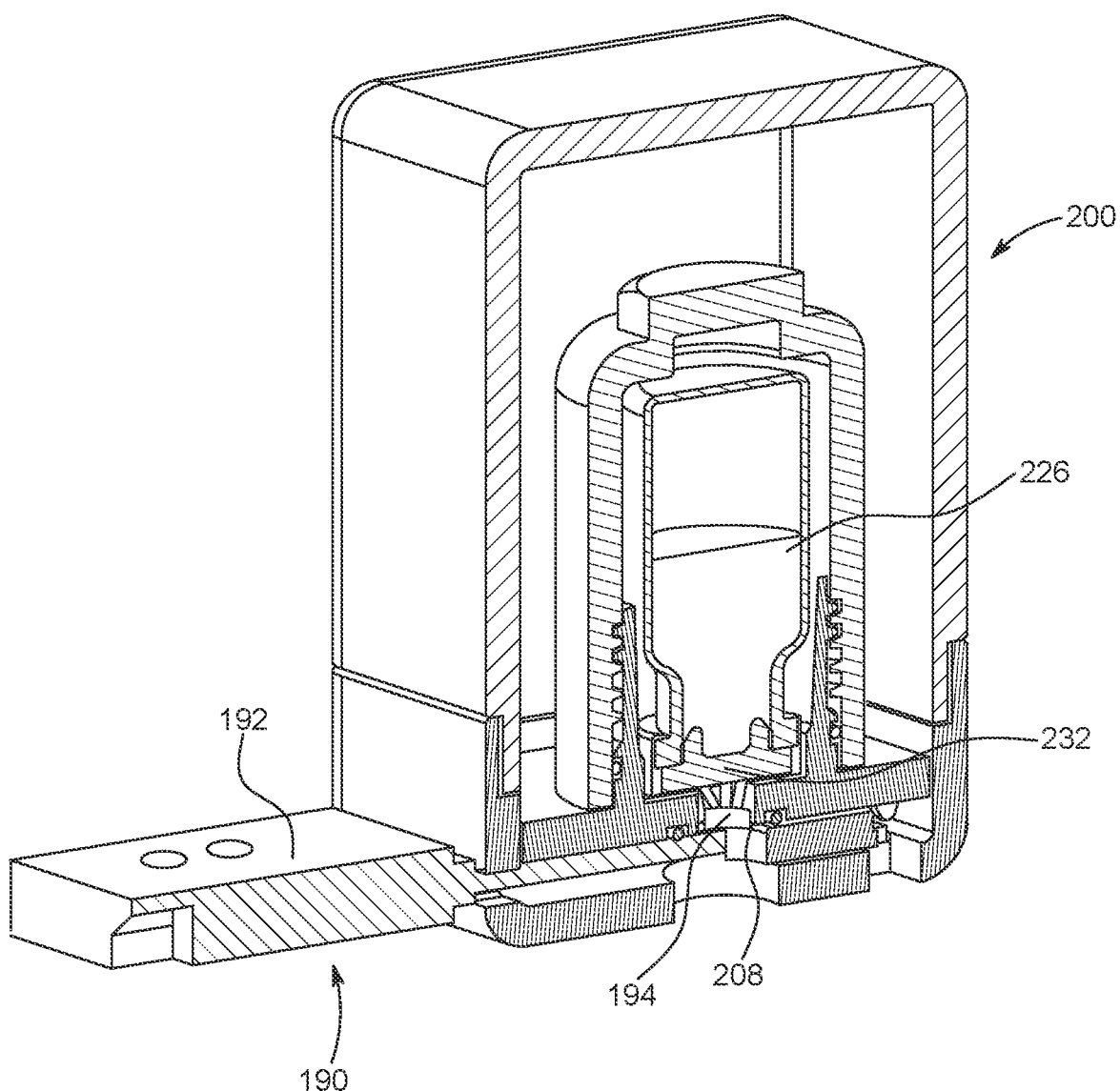
FIG. 34 is a perspective view of a disinfection system for disinfecting a portion of a storage device in accordance with some embodiments or aspects of the present disclosure.

With reference to FIG. 34, a disinfection mechanism 190 is provided for disinfecting the access port 232 of the vessel 226. In some embodiments or aspects, the disinfection mechanism 190 includes a movable arm 192 and a disinfection source 194. The movable arm 192 is movable relative to the storage device 200 such that the disinfection source 194 may be positioned opposite the access port 232. The disinfection source 194 can include, for example, a laser or light emitter that can emit electromagnetic energy at wavelengths capable of inactivating organisms on the surface of the access port 232. Examples of such electromagnetic energy that can be emitted include ultraviolet light (UV) light (10-400 nanometer (nm) wavelength light), ultraviolet C light (UV-C) light (light having a wavelength of 200-280 nm), white light, infrared (IR) light, a laser, etc. (e.g. the disinfection mechanism can include a UV light emitter, UVC LED, IR emitter, etc.). The emitted light can be emitted continuously onto the surface of the access port 232 for a pre-selected disinfection time period to deliver a sufficient energy dose to inactivate organisms on the access port 232 prior to the spike 310 being inserted through the access port 232 and into the vessel 226. In some embodiments or aspects, the disinfection source 194 may be configured to disinfect the access port 232 of the vessel 226 and the spike 310. In this manner, the access port 232 and the spike 310 are disinfected for a sterile connection therebetween. In further embodiments or aspects, a second disinfection source 194 may be provided on the movable arm 192 for disinfecting the spike 310 prior to insertion of the spike 310 into the access port 232 of the vessel 226.

In some embodiments or aspects, the disinfection source 194 can include a nozzle or sprayer that can spray an antiseptic material onto the access port and/or an agitation mechanism that can wipe an antiseptic agent onto the access port of a pre-selected sanitation time period. The disinfection time period that is selected can be based on the type of antiseptic that is utilized and the time period needed to eliminate a pre-selected set of organisms with that antiseptic or reduce the amount of such organisms to at or below a pre-selected threshold level. In some embodiments or aspects, the antiseptic material may be applied at the manufacturing site via an antiseptic containing absorbent member similar to that in a SwabCap made by ICU Medical, Inc. of San Clemente, California. The door 248 may hold the antiseptic containing absorbent member in contact with the access port. The antiseptic, for example 70% isopropyl alcohol disinfects, then evaporates slowly. The continued presence of the absorbent member held by the door 248 maintains the sterility of the access port. The absorbent member is moved with door 248 to allow access to the access port.

Figure 35:
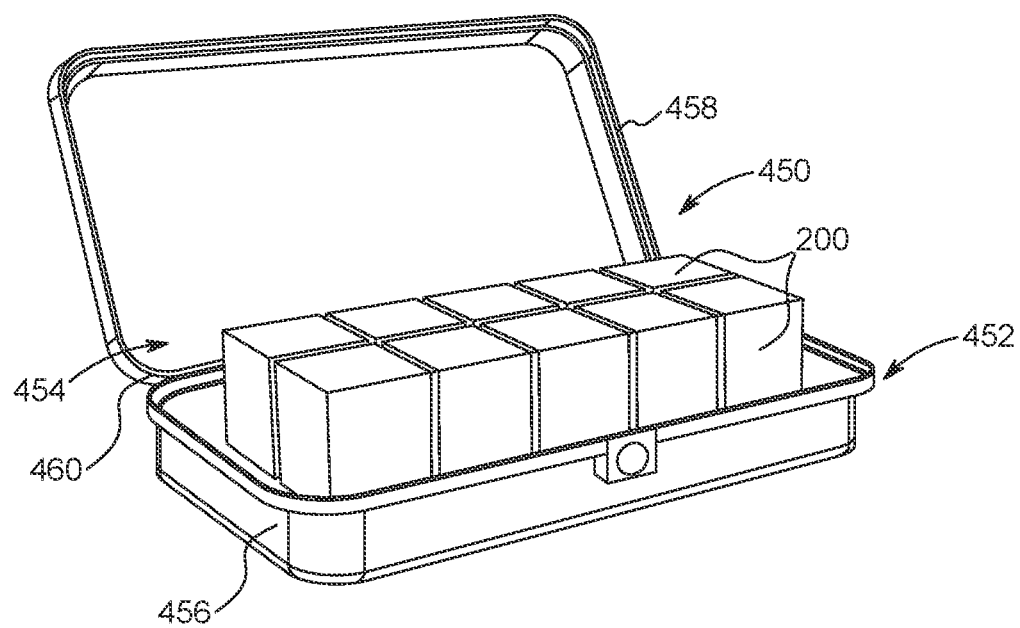
FIG. 35 is a perspective view of a carrier tray for transporting a plurality of storage devices in accordance with some embodiments or aspects of the present disclosure.

With reference to FIG. 35, a storage container 450 for containing a plurality of storage devices 200 is shown in accordance with one embodiment or aspect. In some embodiments or aspects, the storage container 450 may be configured to contain the storage devices 200 during shipping and storage prior to use. The storage container 450 has a housing 452 defining an interior 454 that is configured to receive a plurality of storage devices 200 therein. The housing 452 may have a receiving portion 456 and a lid portion 458 connected to the receiving portion 456 by a hinge 460. In some embodiments or aspects, the housing 454 of the storage container 450, such as at least one of the receiving portion 456 and the lid portion 458, may provide additional shielding properties to provide increased radiation shielding capabilities. In this manner, radiation emitted by the therapeutic or diagnostic agent contained within the storage devices 200 can be contained during shipment and storage.

Figure 36:
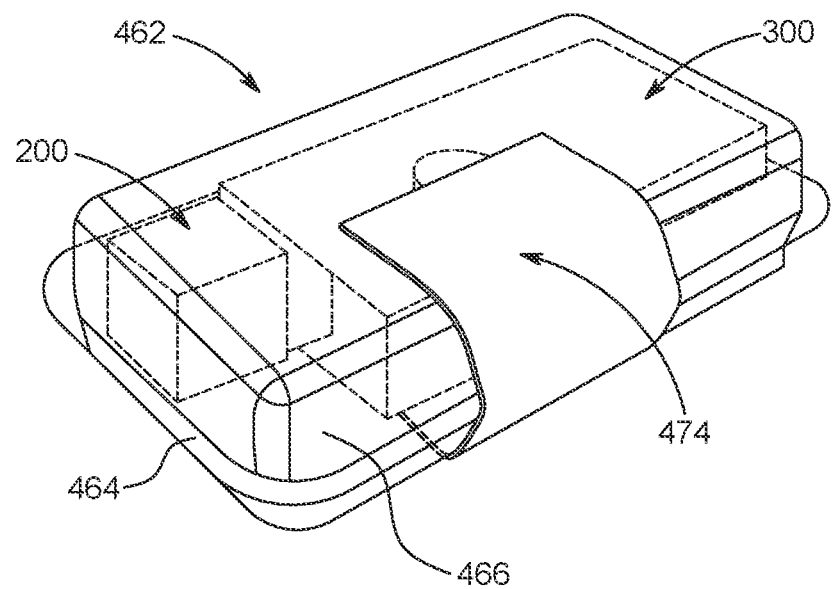
FIG. 36 is a perspective view of a disposal container for disposing a storage device and a cassette in accordance with some embodiments or aspects of the present disclosure.

After the therapeutic or diagnostic agent is output from the storage device 200 and injected into a patient, materials used to inject the therapeutic or diagnostic agent into the patient are collected for storage and disposal. With reference to FIG. 36, a disposal container 462 is provided for containing such materials. In some embodiments or aspects, the disposal container 462 is configured to contain the storage container 200, the fluid cassette 300, and infusion tubing 406 used during an injection procedure. The disposal container 462 has a housing 464 defining an interior 466 that is configured to receive the used storage container 200, fluid cassette 300, and infusion tubing 406. In some embodiments or aspects, the housing 466 of the disposal container 462, may provide shielding properties to provide radiation shielding capabilities. In this manner, radiation emitted by the used storage container 200, fluid cassette 300, and infusion tubing 406 can be contained for safe disposal. In some embodiments or aspects, the disposal container 462 may be configured to seal any remaining fluid in the used storage container 200, fluid cassette 300, and infusion tubing 406.

With continued reference to FIG. 36, a label 474, optionally printed by the delivery system 100, can be applied onto the disposal container 462 to prevent the disposal container 462 from being opened after the used materials are placed into the interior thereof. The label 474 may also provide information about when the materials were used and when the disposal container 462 has been stored long enough for subsequent disposal. The label 474 can have a bar code or RFID tag so that disposal information can be provided to a computer in response to a bar code scanner or RFID reader reading the label 474.

Figure 37:
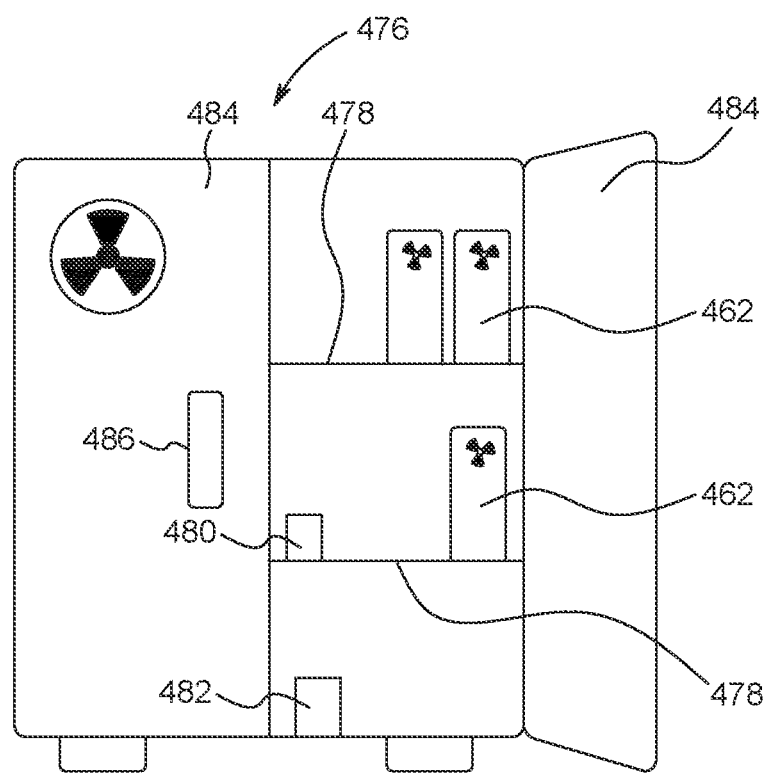
FIG. 37 is a schematic view of a storage enclosure for storing a plurality of disposal containers in accordance with some embodiments or aspects of the present disclosure.

Once the used materials have been placed within a labeled disposal container 462, the disposal container 462 can be temporarily stored in the cart of the delivery system 100. In some embodiments or aspects, the labeled disposal container 462 may be stored in a disposal locker 476, shown in FIG. 37. In some embodiments or aspects, the disposal locker 476 may have a plurality of drawers or shelves 478 each configured to retain a plurality of disposal containers 462. The label 472 on the disposal container 462 can be scanned by a user having a mobile bar code reader. If the read bar code indicates that the materials within the disposal container 462 are sufficiently decayed that they are safe for disposal, an alert, such as a message, sound and/or color can indicate that the scanned disposal container 462 can be removed from the disposal locker 476 and disposed of using an approved disposal process.

In some embodiments or aspects, drawers or shelves 478 of the disposal locker 476 can have at least one indicator 480 (e.g. red and green LEDs) configured to indicate whether a particular disposal container 462 on the drawer or shelf 478 is safe for disposal. For example, a user can scan a bar code of an individual disposal container 462 and provide other input to an inventory management computer 482 to indicate that the individual disposal container 462 has been added to the drawer or shelf 478. The inventory management computer 482 can then determine whether the stored materials within each specific disposal container 462 have decayed sufficiently based on the scanned information related to the used materials (e.g. date of use, etc.) to control the state of the at least one indicator 480. For example, the inventory management computer 482 can control the state of the at least one indicator 480 such that an LED or other indicator means of the at least one indicator 480 indicates the material in the disposal container 462 is too radioactive to throw away (such as by displaying a red color or other message) or such that an LED or other indicator means of the at least one indicator 480 indicates the material in the disposal container 462 can be thrown away (such as by displaying a green color or other message). Such indicia can permit a user to quickly determine whether the disposal container 462 can be thrown away. This can avoid a user having to periodically scan containers or check use dates on the label 474 of each disposal container 462 to determine the disposal status of the disposal container 462.

The disposal locker 476 can have doors 484 to enclose an interior thereof and a locking mechanism 486 for locking the doors 484. In some embodiments or aspects, the locking mechanism 486 may be configured such that only a user with a sufficient credentials can open the doors 484 to access the disposal locker 476. For example, the locking mechanism 486 may be such that the user must have a key to unlock the doors 484 or must have a user badge or access associated with a user log-in to provide input to a controller for unlocking the doors 484.

Among the functions, capabilities and benefits provided by the systems and methods described herein is the minimization of connections that must be made, the minimization of connections that must be separated or broken, and the containment as much as possible of each connection. In some embodiments, methods, or uses of the system, the only connection that is separated is the connection to the patient, and this is preferable only done once all the drug has been delivered and the delivery connection flushed of drug. Thus, there is a much-reduced chance of any drips, spills, or leakage of liquid drug, aerosols, vapors, or gasses being released which may pose a danger to operators or others in the vicinity. Some radioactive daughter products are gasses. Chemotherapeutic aerosols can be a hazard to those in the vicinity.

Figure 38:
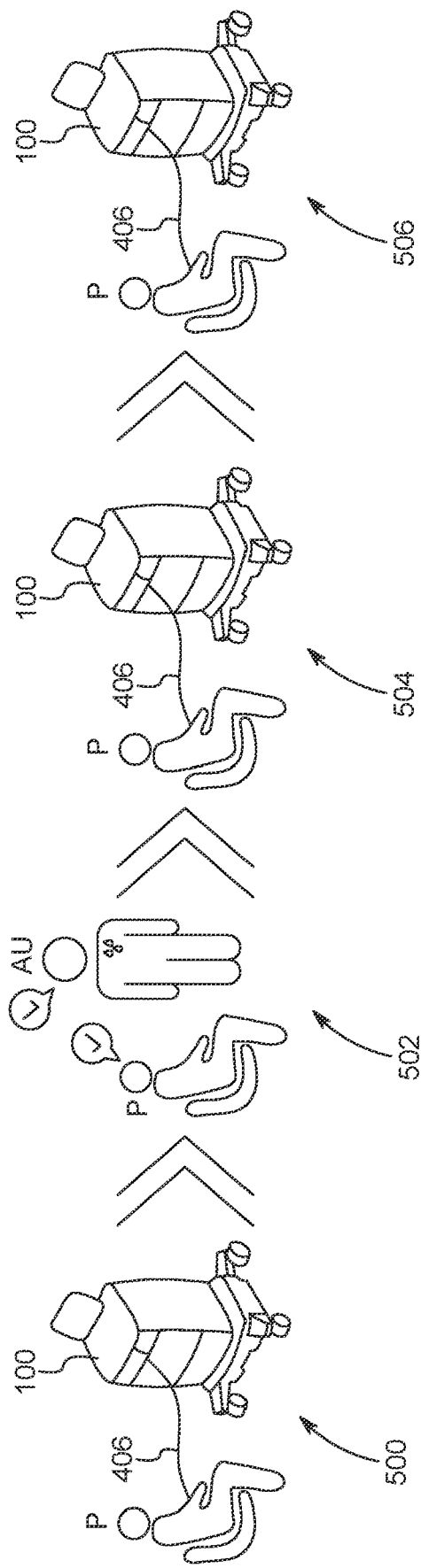
FIG. 38 is a flow diagram for a patency check procedure in accordance with some embodiments or aspects of the present disclosure.

With reference to FIG. 38, an exemplary process for a test infusion prior to delivery of the therapeutic or diagnostic agent is shown. At 500, the patient P is connected to the delivery system 100 via the infusion set 406 and the patient P is administered a test injection of saline or other fluid. For example, the injector 170 can be operated to fill the syringe 312 with saline or other fluid from the auxiliary fluid source 394 and deliver a test injection of saline or other fluid to the patient via the infusion set 406. Volume of saline or other fluid delivered to the patient can be sufficient to confirm whether saline or other fluid is delivered to the patient's vasculature or is extravasated or leaks into tissue. At 502, the patient P and the authorized user AU administering treatment to the patient P confer whether the test injection of saline or other fluid was successful. For example, the authorized user AU may visually check the injection site for signs of extravasation and/or palpate the injection site. The patient P can report any discomfort associated with the test injection of saline or other fluid.

With continued reference to FIG. 38, at 504, the patient P is administered a pre-infusion of saline or other fluid. For example, the injector 170 can be operated to fill the syringe 312 with saline or other fluid from the auxiliary fluid source 394 and deliver the test infusion of saline or other fluid to the patient via the infusion set 406 at a higher volume than during the test injection at 500 and for a longer duration than during the test injection at 500. In some embodiments or aspects, the infusion volume, infusion duration, and/or infusion rate are selected to correspond to the infusion volume, infusion duration, and/or infusion rate for delivery of the therapeutic or diagnostic agent. Research as demonstrated that starting infusions with saline at the full infusion rate reduces the likelihood of extravasation and gives time for an extravasation to be sensed if one is going to happen. At 506, the patient P is administered an injection of the therapeutic or diagnostic agent using a pre-determined injection protocol. This process may be continuous with the pre-infusion of the previous process unless the operator intervenes.

Figure 39:
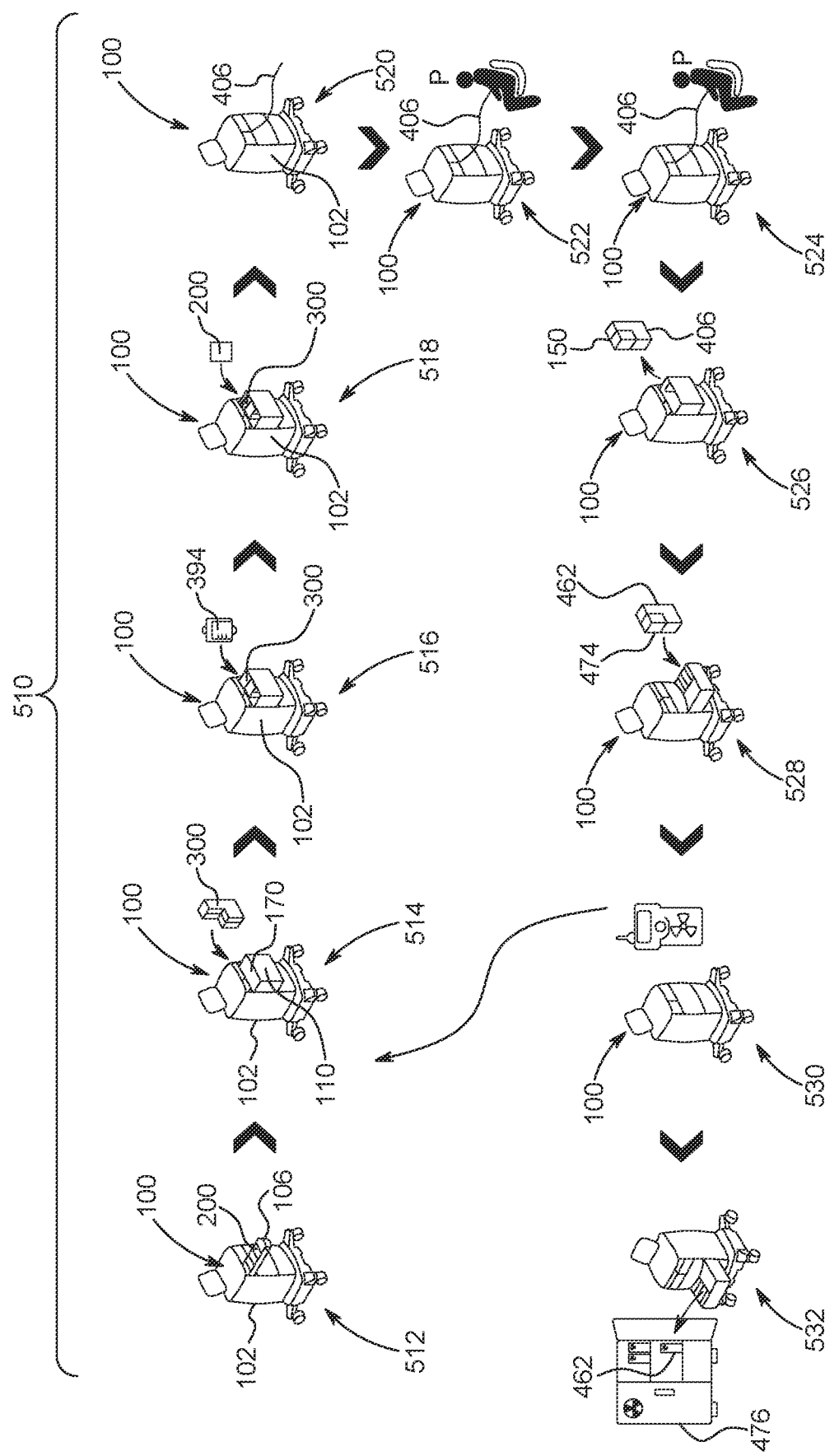
FIG. 39 is a flow diagram for an administration procedure using a system described in accordance with some embodiments or aspects of the present disclosure.

With reference to FIG. 39, an exemplary process for administering a therapeutic or diagnostic agent using the delivery system 100 is shown. At 510, the delivery system 100 is prepared for an administration procedure. For example, at 512, one or more storage devices 200 are loaded into the one or more storage compartments 106 of the cart 102. At 514, a fluid cassette 300 is loaded into the injector 170. For example, the fluid cassette 300 is positioned within the second drawer or shelf 110 of the cart 102 such that the fluid cassette 300 engages the injector 170. In some embodiments or aspects, the alignment elements 370 on the fluid cassette 300 are configured to engage with the alignment pins 176 of the fluid injector (shown in FIG. 26) to locate the fluid cassette 300 relative to the injector 170 such that various components of the injector 170 can interface with the corresponding components of the fluid cassette 300.

With continued reference to FIG. 39, at 516, an auxiliary fluid source 394 is connected to the fluid cassette 300. For example, the auxiliary fluid source 394 may be spiked and fluidly connected to the fluid path set 314 of the fluid cassette 300 via the auxiliary line 396 (shown in FIG. 31). At 518, a storage device 200 is connected to the fluid cassette 300. In some embodiments or aspects, the label, tag, or other indicia 270 on the storage device 200 (shown in FIG. 16) may be scanned prior to or at the time of connecting with the fluid cassette 300 in order to load information about the contents of the storage device 200 into the controller 114.

At 520, the infusion set 406 is fluidly connected to the fluid path set 314 of the fluid cassette 300 (shown in FIG. 31), and the fluid path set 314 and the infusion set 406 are primed. In some embodiments or aspects, the controller 114 of the delivery system 100 (shown in FIG. 5) may be configured to initiate a priming procedure wherein the syringe 312 is operated to draw fluid from the auxiliary fluid source 394 into the fluid path set 314 and deliver the fluid into the infusion set 406 to prime the fluid path set 314 and the infusion set 406 with fluid.

With continued reference to FIG. 39, a test injection procedure is performed at 522. In some embodiments or aspects, the test injection procedure may include 500-504 described herein with reference to FIG. 38.

At 524, the delivery system 100 is configured to administer the therapeutic or diagnostic agent to the patient. For example, the syringe 312 may be operated to be filled with the therapeutic or diagnostic agent from the vessel 226 of the storage device 200, and to deliver the therapeutic or diagnostic agent to the patient P via the infusion set 406 based on a pre-determined administration protocol. In some embodiments or aspects, the delivery system 100 can be configured to administer a unit dose to the patient, wherein a unit dose requires a delivery of the entire contents of the vessel 226. In other embodiments or aspects, the delivery system 100 can be configured to administer a non-unit dose to the patient, wherein a non-unit dose requires a delivery of a portion of the entire contents of the vessel 226.

With continued reference to FIG. 39, at 526, upon completion of the administration procedure, the infusion set 406 is disconnected from the patient P and the assembly 150 of the storage device 200 and the fluid cassette 300 is removed from the injector 170. At 528, the used storage device 200, fluid cassette 300, and infusion set 406 are placed in the disposal container 462, and a label 474 is applied to the disposal container 474 before placing it in temporary storage on the cart 102. For example, the disposal container 462 can be loaded into the third drawer or shelf 112 of the cart 102.

At 530, the treatment room is cleaned and the delivery system 100 can be readied for another administration procedure. At 532, the disposal container 462 is moved to the disposal locker 476 for further decay-in-place of the radioactive material.

The use of label, tag, or other indicia 270 on storage device 200 for administration of new doses and storage of used material for disposal can also provide sufficient information to prompt the ordering of new doses. For example, an inventory system can include a computer that receives information on the storage devices 200 that have been used, such as based on information contained on the label, tag, or other indicia 270 (shown in FIG. 16), and determine whether the number of available doses, such as based on the number of available storage devices 200, is below a pre-selected threshold for triggering the ordering of additional doses. Optionally, the inventory system may compare the number of available doses to the patient scheduling load. In some situations, the inventory system can communicate this condition to a distribution system so that an automated message is sent to the customer to help flag the low inventory and prompt the submission of a new purchase order for additional doses. The inventory system can include software configured to facilitate use of the inventory system. For example, the software can be configured to facilitate inventory management and ordering, written directive generation/acceptance, and compliance report generation. In addition, the use of label, tag, or other indicia 270 on storage device 200 for administration of new doses and storage of used material for disposal can also provide sufficient information to prompt the billing for the use of the drug and system if that is the business arrangement.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

The invention claimed is:

1. A storage device configured to connect to a delivery system for delivering a therapeutic or diagnostic agent, the storage device comprising:
   a housing having a chamber defined therein;
   a vessel positioned within the chamber, the vessel having
      a distal end opposite a proximal end with an interior defined therebetween and configured for receiving the therapeutic or diagnostic agent, the proximal end having an access port for accessing the interior;
   a door associated with the housing, the door movable relative to the housing between a closed position and an open position, wherein, in the closed position, the door covers an opening in the housing to enclose the chamber of the housing, and wherein, in the open position, the door reveals the opening in the housing for accessing the access port of the vessel; and
a holder within the chamber of the housing and in contact with the vessel to fix the vessel relative to the housing such that the access port of the vessel is positioned at the opening in the housing;
wherein the door is moveable between the closed position and the open position in response to actuation by an access mechanism of the delivery system.

2. The storage device according to claim 1, wherein the holder comprises a contact element for contacting the distal end of the vessel and a plurality of tabs connected to the contact element and configured to engage an inner surface of the housing to fix the distal end of the vessel relative to the housing.

3. The storage device according to claim 1, further comprising a plurality of ribs within the chamber of the housing and surrounding the opening, wherein the plurality of ribs are configured for fixing the proximal end of the vessel relative to the housing.

4. The storage device according to claim 1, further comprising a lock for locking the door in one of the open position and the closed position.

5. The storage device according to claim 1, further comprising a door cover connected to the housing, wherein the door cover encloses the door within a door chamber.

6. The storage device according to claim 5, wherein the door cover comprises a door access opening having a seal, and a vessel access opening positioned opposite the opening in the housing.

7. The storage device according to claim 6, wherein the seal is pierceable by the access mechanism of the delivery system.

8. The storage device according to claim 1, further comprising a label or a tag on the housing that contains machine readable authenticatable data that includes at least one of product information, production information, prescription information, and shipping conditions information.

9. The storage device according to claim 1, wherein the opening in the housing is configured to receive a vessel access member extending into the access port for accessing the therapeutic or diagnostic agent contained in the vessel when the door is in the open position.

10. The storage device according to claim 1, wherein the therapeutic or diagnostic agent is a radiopharmaceutical, and wherein the housing comprises shielding configured to prevent radiation from the radiopharmaceutical from being emitted out of the housing.

11. An assembly configured to connect to a delivery system for delivering a therapeutic or diagnostic agent, the assembly comprising:
a storage device containing the therapeutic or diagnostic agent; and
a fluid cassette fluidly connectable to the storage device for accessing the therapeutic or diagnostic agent,
wherein the storage device comprises:
a housing having a chamber defined therein;
a vessel positioned within the chamber, the vessel having an interior configured for receiving the therapeutic or diagnostic agent and an access port for accessing the interior; and
a door associated with the housing, the door movable relative to the housing between a closed position and an open position, wherein, in the closed position, the door covers an opening in the housing to enclose the chamber of the housing, and wherein, in the open position, the door reveals the opening in the housing for accessing the access port of the vessel,
wherein the fluid cassette comprises:
a vessel access member, a metering device, and a fluid path set fluidly connecting the vessel access member to the metering device; and
an enclosure enclosing the vessel access member, the metering device, and the fluid path set, and
wherein the storage device and the fluid cassette are configured to connect to the delivery system such that the door of the storage device is accessible by an access mechanism of the delivery system and such that the vessel access member and the metering device of the fluid cassette are accessible by a delivery mechanism of the delivery system.

12. The assembly according to claim 11, wherein the vessel access member of the fluid cassette is insertable into the access port of the vessel when the door is moved to the open position to fluidly connect the metering device to the vessel via the fluid path set.

13. The assembly according to claim 11, wherein the fluid path set comprises one or more valves operable by the delivery mechanism of the delivery system for regulating fluid flow through the fluid path set.

14. The assembly according to claim 11, wherein the fluid cassette is connectable to a saline source.

15. The assembly according to claim 11, wherein the storage device comprises a guide mechanism configured for positioning the storage device in a desired orientation relative to the fluid cassette.

16. The assembly according to claim 15, wherein the guide mechanism comprises one or more geometric features on the storage device, and wherein the one or more geometric features are configured to mate with corresponding one or more geometric features on the fluid cassette.

17. The assembly according to claim 11, wherein an outlet of the metering device of the fluid cassette is configured to connect to an infusion set for delivering a dose of the therapeutic or diagnostic agent from the vessel to the infusion set.

18. The assembly according to claim 11, further comprising a label or a tag on the housing that contains machine readable authenticatable data that includes at least one of product information, production information, prescription information, and shipping conditions information.

19. The assembly according to claim 11, wherein the therapeutic or diagnostic agent is a radiopharmaceutical, and wherein the housing comprises shielding configured to prevent radiation from the radiopharmaceutical from being emitted out of the housing.

20. A delivery system for delivering a therapeutic or diagnostic agent, the delivery system comprising:
an injector having a delivery mechanism and an access mechanism; and
a fluid delivery assembly removably connectable to the injector, the fluid delivery assembly comprising:
a storage device containing the therapeutic or diagnostic agent; and
a fluid cassette fluidly connectable to the storage device for accessing the therapeutic or diagnostic agent,
wherein the storage device comprises:
a housing having a chamber defined therein;
a vessel positioned within the chamber, the vessel having an interior configured for receiving the therapeutic or diagnostic agent and an access port for accessing the interior; and a door associated with the housing, the door movable relative to the housing via the access mechanism of the injector between a closed position and an open position, wherein, in the closed position, the door covers an opening in the housing to enclose the chamber of the housing, and wherein, in the open position, the door reveals the opening in the housing for accessing the access port of the vessel, wherein the fluid cassette comprises:
a vessel access member, a metering device, and a fluid path set fluidly connecting the vessel access member to the metering device; and
an enclosure enclosing the vessel access member, the metering device, and the fluid path set, and
wherein the vessel access member and the metering device of the fluid cassette are accessible by the delivery mechanism of the injector for fluidly connecting the interior of the vessel with the metering device via the fluid path set.

21. The delivery system according to claim 20, further comprising an injector controller configured to determine a dose of the therapeutic or diagnostic agent to be drawn from the vessel into the metering device based on machine readable authenticatable data on the storage device.

22. The delivery system according to claim 21, wherein the injector controller is further configured to determine the dose of the therapeutic or diagnostic agent to be drawn from the vessel into the metering device based on at least one patient parameter.

23. The delivery system according to claim 22, wherein the injector controller is configured to be connected to a hospital network system.

24. The delivery system according to claim 22, wherein the injector controller comprises a plurality of dosing algorithms for different pre-defined therapies or diagnostic procedures.

25. The delivery system according to claim 20, wherein the fluid path set comprises one or more valves operable by the delivery mechanism of the delivery system for regulating fluid flow through the fluid path set.

26. The delivery system according to claim 20, wherein the fluid cassette is connectable to a saline source.

27. The delivery system according to claim 20, wherein an outlet of the metering device of the fluid cassette is configured to connect to an infusion set for delivering a dose of the therapeutic or diagnostic agent from the vessel to the infusion set.

28. The delivery system according to claim 20, wherein the storage device is configured to be removably or non-removably connectable to the fluid cassette.

29. The delivery system according to claim 20, further comprising a label or a tag on the housing that contains machine readable authenticatable data that includes at least one of product information, production information, prescription information, and shipping conditions information.

30. The delivery system according to claim 20, wherein the therapeutic or diagnostic agent is a radiopharmaceutical, and wherein the housing comprises shielding configured to prevent radiation from the radiopharmaceutical from being emitted out of the housing.

* * * * *

UNITED STATES PATENT AND TRADEMARK OFFICE
CERTIFICATE OF CORRECTION

PATENT NO. : 12,233,027 B2  
APPLICATION NO. : 18/436633  
DATED : February 25, 2025  
INVENTOR(S) : Volkar et al.

Page 1 of 1

It is certified that error appears in the above-identified patent and that said Letters Patent is hereby corrected as shown below:

In the Specification

In Column 7, Line 67, delete "positon" and insert -- position --, therefor.
In Column 15, Line 15, delete "7;" and insert the same at Line 14, after "device shown in FIG.", as a continuation sub-point.
In Column 15, Line 43, delete "view the" and insert -- view of the --, therefor.
In Column 16, Line 1, delete "view the" and insert -- view of the --, therefor.
In Column 19, Line 42, delete "contacted that" and insert -- contacted the --, therefor.
In Column 22, Line 9, delete "flourine-18," and insert -- fluorine-18, --, therefor.
In Column 32, Line 64, delete "is a" and insert -- in a --, therefor.
In Column 40, Line 62, delete "as" and insert -- has --, therefor.

Signed and Sealed this  
Sixth Day of May, 2025

Coke Morgan Stewart  
*Acting Director of the United States Patent and Trademark Office*